US009363959B2

(12) United States Patent
Skadhauge et al.

(10) Patent No.: US 9,363,959 B2
(45) Date of Patent: Jun. 14, 2016

(54) BARLEY WITH REDUCED LIPOXYGENASE ACTIVITY AND BEVERAGE PREPARED THEREFROM

(75) Inventors: Birgitte Skadhauge, Bikerød (DK); Finn Lok, Valby (DK); Klaus Breddam, Osted (DK); Ole Olsen, Copenhagen S. (DK); Lette Mølskov Bech, Smørum (DK); Søren Knudsen, Måløv (DK)

(73) Assignees: CARLSBERG BREWERIES A/S, Copenhagen (DK); HEINEKEN SUPPLY CHAIN B.V., Amsterdam (NL)

( * ) Notice: Subject to any disclaimer, the term of this patent is extended or adjusted under 35 U.S.C. 154(b) by 1294 days.

(21) Appl. No.: 13/141,579

(22) PCT Filed: Dec. 28, 2009

(86) PCT No.: PCT/DK2009/050355
§ 371 (c)(1),
(2), (4) Date: Sep. 14, 2011

(87) PCT Pub. No.: WO2010/075860
PCT Pub. Date: Jul. 8, 2010

(65) Prior Publication Data
US 2011/0318469 A1 Dec. 29, 2011

(30) Foreign Application Priority Data
Dec. 30, 2008 (DK) .................................. 2008 01851

(51) Int. Cl.
*A01H 5/10* (2006.01)
*C12C 1/18* (2006.01)
*C12C 12/00* (2006.01)

(52) U.S. Cl.
CPC .. *A01H 5/10* (2013.01); *C12C 1/18* (2013.01); *C12C 12/00* (2013.01); *C12C 2200/01* (2013.01)

(58) Field of Classification Search
None
See application file for complete search history.

(56) References Cited

U.S. PATENT DOCUMENTS

| 6,696,294 B1 | 2/2004 | Konzak | |
| 7,420,105 B2 * | 9/2008 | Breddam et al. | 800/320 |
| 2003/0167544 A1 | 9/2003 | Douma et al. | |
| 2005/0204437 A1 | 9/2005 | Breddam et al. | |
| 2006/0005276 A1 | 1/2006 | Falco et al. | |
| 2007/0067871 A1 | 3/2007 | Wu et al. | |

FOREIGN PATENT DOCUMENTS

| DE | 44 28 978 | 3/1995 | |
| EP | 1 609 866 | 12/2005 | |
| JP | 2006-034129 | 2/2006 | |
| NL | 1018971 | 3/2003 | |
| WO | WO 02/053721 | * 7/2002 | C12N 9/02 |
| WO | WO 2004/011591 | 2/2004 | |
| WO | WO 2005/087934 | 9/2005 | |

OTHER PUBLICATIONS

Hotzel, H. et al. Euro. Food Res Tecnol. (1999) vol. 209:192-196.*
Baur, C. and Grosch. W., "Investigation about the taste of di-, tri- and tetrahydroxy fatty acids" Z. Lebensm. Unters. Forsch. 165: 82-84 (1977).
Baur, C. et al., "Enzymatic oxidation of linoleic acid: Formation of bittertasting fatty acids" Z. Lebensm.Unters.Forsch. 164: 171-176 (1977).
Drost, B.W. et al., "Role of individual compounds in beer staling" Tech. Q. MBAA 11:127-134 (1974).
Drost, et al. "Flavor Stability", American Society of Brewing Chemists, 1990, vol. 48, No. 4.
Durai, S. et al., "Zinc finger nucleases: custom-designed molecular scissors for genome engineering of plant and mammalian cells." Nucleic Acids Res.33:5978-5990, 2005.
Esterbauer et al. "Isomere Trihydroxy-octadecensäuren in Bier: Beweise für ihr Vorkommen und ihre quantitative Bestimmung" Z. Lebensm. Unters-Forsch. 164, 255-259 (1977), p. 255-259.
Esterbauer et al. "Zur Bildung isomerer Trihydroxy-octadecensäuren bei der enzymatischen Oxydation von Linolsäure durch Gerstenmehl", Monatshefte für Chemie, vol. 108/5, 963-972 (1977).
Groenqvist, A. et al., "Carbonyl compounds during beer production in beer" Proceedings of the 24th EBC Congress, Oslo, pp. 421-428 (1993).
Hamberg, "Trihydroxyoctadecenoic Acids in Beer: Qualitative and Quantitative Analysis", J. Agric. Food Chem., 1991, 39, p. 1568-1572.
Hansen, M. et al., "Antisense-mediated suppression of C-hordein biosynthesis in the barley grain results in correlated changes in the transcriptome, protein profile, and amino acid composition" J. Exp. Bot. 58:3987-3995 (2007).
Hirota et al. "Development of Novel Barley with Improved Beer Foam and Flavor Stability—The Impact of Lipoxygenase-1-Less Barley in the Brewing Industry", MBAA TQ, vol. 43, No. 2, 2006, pp. 131-135.
Hirota et al. "Mapping a factor controlling the thermostability of seed lipoxygenase-1 in barley", Plant Breeding 125, p. 231-235, 2006.
Hirota N et al "Brewing performance of malted lipoxygenase-1 null barley and effect on . . . "

(Continued)

*Primary Examiner* — Russell Kallis
(74) *Attorney, Agent, or Firm* — McNeill Baur PLLC

(57) ABSTRACT

According to the invention, there is provided barley with total loss of functional lipoxygenase (LOX)-1 and LOX-2 enzymes, and plant products produced thereof, such as malt manufactured by using barley kernels defective in the synthesis of the fatty acid-dioxygenating enzymes LOX-1 and LOX-2. Said enzymes account for the principal activities related to dioxygenation of linoleic acid into 9- and 13-hydroperoxy octadecadienoic acid, respectively. 9-Hydroperoxy octadecadienoic acid represents a LOX pathway metabolite, which—through further enzymatic or spontaneous reactions—may lead to the appearance of trans-2-nonenal (T2N). The invention enables brewers to produce a beer having insignificant levels of stale, T2N-specific off-flavors, even after prolonged storage of the beverage.

17 Claims, 24 Drawing Sheets

(56) References Cited

OTHER PUBLICATIONS

Hirota N et al "Characterization of lipoxygenase-1 null mutants in barley".

Hotzel Helmut et al. "Recovery and characterization of residual DNA from beer as a prerequisite for the detection of genetically modified ingredients", European Food Research and Technology, vol. 209, No. 3-4, 1999, p. 192-196.

Hugues Mireille et al "Two Lipoxygenases from Germinated Barley—Heat and Kilning Stability".

Iida, S. and Therada, R., "Modification of endogenous natural genes by gene targeting in rice and other higher plants." Plant Mol. Biol. 59:205-219, 2005.

Jamieson, A.M. and van Gheluwe, J.E.A., "Identification of a compound responsible for cardboard flavor in beer" Proc. Am. Soc. Brew. Chem. 29:192-197 (1970).

Kleinhofs, A. et al., "Induction and selection of specific gene mutations in Hordeum and Pisum." Mutat. Res. 51:29-35, 1978.

Kobayashi et al. "Behavior of Mono-, Di-, and Trihydroxyoctadecenoic Acids during Mashing and Methods of Controlling Their Production", Journal of Bioscience and Bioengineering, vol. 90, No. 1, p. 69-73, 2000.

Kobayashi et al. "The Production of Linoleic and Linolenic Acid Hydroperoxides during Mashing", J. of Fermentation and Bioengineering, vol. 76, No. 5, 371-375. 1993.

Kowaka et al. "Malting barly improvement for brewing", Nippon Jozo Kyokaishi (1993), 88(8), 574-81.

Kumar, S. et al., "Gene targeting in plants: fingers on the move." Trends Plant Sci. 11:159-161, 2006.

Kuroda et al. Characterization of 9-fatty acid hydroperoxide lyase-like activity in germaniting barley seeds that transforms 9(s)-hydroperoxy-10 . . . .

Kuroda et al. "Characterization of factors involved in the production of 2(E)-nonenal during mashing".

Kuroda et al. "Trihydroxyoctadecenoic acids having negative effects on beer foam are produced by enzymatic factors present in malt", Sapporo Breweries Ltd., Brewing Research Laboratories.

Kuroda H et al. "Characterization of factors that transform linoleic acid into di- and trihydroxyoctadecenoic acids in mash".

Lermusieau et al. "Nonoxidative Mechanism for Development of trans-2-Nonenal in Beer", American Society of Brewing Chemists, publ. No. J-1999-0204-05R.

Liégeois, C. et al., "Release of deuterated (E)-2-nonenal during beer aging from labeled precursors synthesized before boiling" J. Agric. Food Chem. 50:7634-7638 (2002).

Martins et al. "Resistance to stem canker, frogeye leaf spot and powdery mildew of soybean lines lacking lipoxygenases in the seeds", Scientia Agricola, v.59, n.4, p. 701-705, out./dez. 2002.

Mats Hamberg "An Epoxy Alcohol Synthase Pathway in Higher Plants: Biosynthesis of Antifungal Trihydroxy Oxylipins in Leaves of Potato", Lipids, vol. 34, No. 11 (1999).

Mechelen van J. R. et al "Molecular characterization of two lipoxygenases from barley".

Meilgaard, M.C., "Flavor chemistry of beer: Part II: Flavor and threshold of 239 aroma volatiles" Tech. Q. MBAA 12:151-167 (1975).

Noordermeer, M.A. et al., "Fatty acid hydroperoxide lyase: A plant cytochrome P450 enzyme involved in wound healing and pest resistance" ChemBioChem 2:494-504 (2001).

Nyborg, M. et al., "Investigations of the protective mechanism of sulfite against beer staling and formation of adducts with trans-2-nonenal" J. Am. Soc. Brew. Chem. 57:24-28 (1999).

Robbins, M.P. et al., "Genetic manipulation of condensed tannins in higher plants" Plant Physiol. 116: 1133-1144 (1998).

Rutgersson A. et al "Optimization of temperature, time, and lactic acid concentration to inactivate lipoxygenase and lipase and preserve phytase activity in barley (CV. Blenheim) during soaking".

Schmitt, N. F. and van Mechelen, J.R., "Expression of lipoxygenase isoenzyme in developing barley grains" Plant Sci. 128: 141-150 (1997).

Sovrano et al, Food Chemistry; 99: 711-717: 2006.

Stahl, Y. et al., "Antisense downregulation of the barley limit dextrinase inhibitor modulates starch granule sizes distribution. Starch compositions and amylopectin structure" Plant J. 39: 599-611 (2004).

Stenroos et al. "Origin and Formation of 2-Nonenal in Heated Beer", MBAA Tech. Quarterly, vol. 13, No. 4, 1976, p. 227-232.

Suda et al. "Simple and Rapid Method for the Selective Detection of Individual Lipoxygenase Isozymes in Soybean Seeds", American Chemical Society, 1995.

Tzfira, T. and White, C., "Towards targeted mutagenesis and gene replacement in plants." Trends Biotechnol. 23:567-569, 2005.

Wackerbauer, K. and Meyna, S., "Freie und triglyceride-gebundene Hydroxyfettsäuren in Gerste und Malz", Monatsschrift für Brauwissenschaft, heft 3/4: 52-57 (2002).

Wan Heng Wang et al "Molecular basis of a null mutation in soybean lipoxygenase 2: substitution of glutamine for an iron-ligand histidine".

Wu et al. "Rapid Separation and Genotypic Variability of Barley (Hordeum vulgare L.) Lipoxygenase Isoenzymes", Journ. of Cereal Science, 25 (1997), p. 49-56.

International Search Report and Written Opinion for Application No. PCT/DK2009/050355 mailed May 25, 2011.

G Yang & PB Schwarz, J. Am. Brew. Chem. 53(2): 45-49 (1995).

R. Willaert, Chapter 20 (pp. 441-503) in The Handbook of Food Products Manufacturing, Y.H. Hui, Ed., John Wiley & Sons, Inc. (2007).

* cited by examiner

BARLEY WITH REDUCED LIPOXYGENASE ACTIVITY AND BEVERAGE PREPARED THEREFROM

All patent and non-patent references cited in the application are hereby incorporated by reference in their entirety.

This application contains a sequence listing submitted in electronic format. The file name is "2015-06-25-01130-0003-00US-Seq.Listing.txt," it was created on Jun. 25, 2015, and is 36,864 bytes in size.

FIELD OF INVENTION

The present invention relates to advances in plant biotechnology, enabling the disclosure of barley plants, and products thereof, which are defective in synthesis of two lipoxygenase (LOX) enzymes, LOX-1 and LOX-2—thus offering new raw materials for a variety of usages. Said raw materials, when for example exploited in beverage production, facilitate the fielding of new manufacture capabilities for more distinctive, flavor-stable beers that accumulate remarkably low levels of the off-flavor compound trans-2-nonenal (T2N)—with an additional benefit of only containing low levels of T2N potential.

BACKGROUND OF INVENTION

A large fraction of beer is produced on the basis of barley (*Hordeum vulgare*, L.), which is a monocotyledonous crop plant grown in many parts of the world. It is propagated not only due to its economic importance as a source of industrial products, such as beer, but also as a source of animal feed.

Methods are unfortunately not available for preparing transgenic barley plants that completely lack expression of a given gene and corresponding protein. In general for barley, application of antisense techniques may be utilized to generate transgenic plants that still express some of the protein (see, for example, Robbins et al., 1998; Stahl et al., 2004; Hansen et al., 2007). Also, effective methods have not been developed for preparing specific mutations using chimeric RNA/DNA or site-directed mutagenesis in barley plants. In fact, not a single example of successful oligonucleotide-directed gene targeting in barley has been published. Iida and Terada (2005) noted that oligonucleotide-directed gene targeting has been pursued in maize, tobacco and rice, but not in barley—and in all cases with the ALS gene as a target. Part of the research conclusion was that it remains to be seen whether the strategy with appropriate modifications can be applicable to genes other than those directly selectable, such as the ALS genes. Targeted mutagenesis using zinc-finger nucleases represents another tool that could be used in the future to investigate basic plant biology or to modify crop plants (Durai et al., 2005; Tzfira and White, 2005; Kumar et al., 2006). Also in this case, mutagenesis has not been pursued or successfully applied in barley.

Barley mutants, however, may be prepared by random mutagenesis using chemical treatment or irradiation, such as by treatment with sodium azide ($NaN_3$; FIG. 1). An example is barley kernels mutagenized with $NaN_3$, and screened for high levels of free phosphate, with the aim to identify low-phytate mutants (Rasmussen and Hatzack, 1998); a total of 10 mutants out of 2,000 screened kernels were identified. However, identification of a particular mutant after $NaN_3$ treatment requires an effective screening method and is far from always successful.

In 1970, the molecule conferring the cardboard-like flavor in beer was isolated and identified as T2N, a volatile $C_9$ alkenal (Jamieson and Gheluwe, 1970). Since the taste-threshold level for T2N in humans is extremely low, previously determined to be around 0.7 nM or 0.1 ppb (Meilgaard, 1975), products with even minute levels of the aldehyde are regarded as being aged due to the off-flavor taste of the product. However, the T2N level is generally very low in fresh beer (Lermusieau et al., 1999), so it has been speculated that during storage, free T2N may be liberated from T2N adducts (Nyborg et al., 1999). This notion was supported by a subsequent observation that the T2N potential in wort correlates with formation of T2N after product storage (Kuroda et al., 2005).

The barley kernel contains three LOX enzymes known as LOX-1, LOX-2, and LOX-3 (van Mechelen et al., 1999). LOX-1 catalyzes the formation of 9-hydroperoxy octadecadienoic acid (9-HPODE; see FIG. 2 for a partial overview of LOX pathway)—a precursor of both T2N and trihydroxy octadecenoic acids (abbreviated THAs)—from linoleic acid. LOX-2 mainly catalyzes the conversion of linoleic acid to 13-HPODE, which is further metabolized to hexanal, a $C_6$ aldehyde with a ~0.4-ppm-high taste threshold (Meilgaard, supra). LOX-3 action is probably not of relevance with respect to the instant application for two reasons: the expression level of the corresponding gene in barley kernels is very low, and the product specificity of LOX-3 remains elusive.

In support of the aforementioned data, several reports have noted that T2N is produced via a biochemical pathway involving conversion of linoleic acid to 9-HPODE, initially catalyzed by LOX-1, and then cleavage of 9-HPODE through 9-hydroperoxide lyase action (see, for example, Kuroda et al., 2003, 2005; Noodermeer et al., 2001).

There appears to be no correlation between the overall LOX activity in malt and the wort nonenal potential. However, there have been speculations about a significant correlation between LOX-1 activity and wort T2N potential, primarily because LOX-2 activity was considered inferior with respect to formation of the T2N potential in wort (Kuroda et al., 2005).

In FIG. 2 is, as mentioned above, shown a part of the LOX pathway, here focusing on biochemical reactions from linoleic acid to T2N. The major activity of the LOX-1 enzyme concerns the conversion of linoleic acid to 9-HPODE, which is an upstream metabolite of the biochemical pathway leading to formation of T2N. In contrast, the major activity of LOX-2 relates to the conversion of linoleic acid into 13-HPODE, which is separate from the aforementioned biochemical pathway to T2N. It is notable that LOX-1 and LOX-2 enzymes may utilize linolenic acid as substrate, but this activity is outside the scope of the instant application as the corresponding pathways do not lead to T2N formation.

LOX-1 has been thought to contribute with the major LOX activity in malt (see, for example, Kuroda et al., 2003).

Several different barley plants have been developed, which are characterized by reductions in, or lack of, LOX-1 activity. For example, barley kernels and barley plants having a low LOX-1 activity were disclosed in PCT application WO 02/053721 to Douma, A. C. et al. And in WO 2005/087934 to Breddam, K. et al., attention was on two different barley mutants deficient in LOX-1 activity—a splice mutant and a mutant with a premature translational stop codon. These were identified following propagation and screening of mutated plants, as illustrated in FIG. 1. While the above-mentioned mutants were identified by screening $NaN_3$-mutagenized barley, Hirota, N. et al. described in EP 1609866 a barley plant with no LOX-1 activity, which was identified by screening a collection of barley landraces.

Several examples on mutated plants that synthesize low levels of LOX are known. However, no barley plant deficient in several lipoxygenase activities, for example no barley plant deficient in activities of both LOX-1 and LOX-2 has been described. Methods to enable genetic manipulation of plants are frequently specific to a specific kind of plant, and thus—despite that few rice plants, soy plants, or *Arabidopsis* plants are known to comprise low levels of LOX—the methods for preparing such plants cannot be used in the generation of barley plants with low, or no, LOX activity. In addition, LOX mutants of one plant species may have different properties in comparison with LOX mutants of another plant species.

SUMMARY OF INVENTION

Wort is a complex key liquid in the production of malt based beverages such as beer (cf. FIG. 3 that provides an overview on the entire process of making beer). Wort made from barley plants deficient in LOX-1 activity is actually characterized by comprising significant levels of T2N potential, although said level is lower than that in wort prepared from wild-type barley. Since said potential in wort correlates with T2N formed in beer after storage (Kuroda et al., 2005), there is accordingly a need for barley plants useful in the production of wort with a substantially reduced level of T2N potential.

Methods for reducing LOX activity by heat treatment have been described. However, the heat treatment was generally undertaken during malting and/or preparation of wort, and products of LOX activity were thus allowed to accumulate in the barley until undertaking of the heat treatment. Analysis of barley revealed that significant amounts of products of LOX activity were present in barley, even prior to malting (Wackerbauer and Meyna, 2002).

The present invention provides barley plants deficient in LOX-1 and LOX-2 activities and discloses that said barley plants have several profound, surprising advantages. As mentioned herein above, Kuroda et al. (supra) described a lack in correlation between the LOX activity in malt and the T2N potential in wort, and attributed this to the presence of LOX-2 activity. Kuroda et al. (2005) accordingly proposed an insignificant role of LOX-2 with respect to the formation of T2N potential.

Brewing researchers have wrestled with understanding what dictates the formation of free T2N and T2N potential. It is therefore unexpected, perhaps perplexing, when the present invention provides experimental evidence to disclose the beneficial effect of using barley plants deficient in both LOX-1 and LOX-2 activities for production of wort that exhibits very low levels of T2N potential. And also the level of free T2N in wort prepared from barley plants deficient in both LOX-1 and LOX-2 activities was found to be lower than that prepared from null-LOX-1 barley.

It is one objective of the present invention to provide beverages prepared from a barley plant, or a part thereof, wherein said beverage comprises very low levels of T2N potential—and wherein said barley plant, or part thereof, comprises a first mutation that results in a total loss of function of LOX-1 activity, such as total loss of functional LOX-1 enzyme, and a second mutation resulting in a total loss of function of LOX-2 activity, such as total loss of active LOX-2 enzyme.

The invention also is aimed at providing barley plants useful in the preparation of the beverages of the invention. Thus, the invention describes the generation of barley plants, or parts thereof, comprising a first mutation resulting in a total loss of function of LOX-1 activity, such as total loss of functional LOX-1 enzyme, and a second mutation resulting in a total loss of function of LOX-2 activity, such as total loss of functional LOX-2 enzyme.

In addition, the invention provides plant products comprising a processed barley plant, or part thereof, wherein said plant comprises a first mutation that results in a total loss of function of LOX-1 activity, such as total loss of functional LOX-1 enzyme, and a second mutation resulting in a total loss of function of LOX-2 activity, such as a total loss of functional LOX-2 enzyme. Without limitations, the aforementioned plant products may, for example, be a malt composition, or a wort composition, or a beverage (such as a malt-based beverage, e.g. beer or non-alcoholic malt based beverages), or a barley-based beverage, or a beverage based on a mixture of malt and barley and optionally other ingredients. The plant products may also be barley syrups, malt syrups, barley extracts, and malt extracts.

Moreover, the invention also relates to methods to produce a beverage characterized by a very low level of T2N potential, said methods comprising the steps of:

(i) preparing a composition comprising a barley plant, or parts thereof, comprising a first mutation that results in a total loss of function of LOX-1 activity, such as total loss of functional LOX-1 enzyme, and a second mutation resulting in a total loss of functional LOX-2, such as total loss of active LOX-2 enzyme;

(ii) processing the composition of (i) into a beverage; thereby obtaining a beverage characterized by a very low level of T2N potential.

The invention also concerns barley plants, which—in addition to comprising a first mutation resulting in a total loss of function of LOX-1 activity, and a second mutation resulting in a total loss of function of LOX-2 activity—comprise one or more additional, useful mutations.

DESCRIPTION OF DRAWINGS

FIG. 11), either produced by barley brewing or using normal malting and mashing. Shown are also the LOX-1 and LOX-2 genotypes of the raw materials used (wt: wild-type).

DETAILED DESCRIPTION OF THE INVENTION

Definitions

Figure 1:
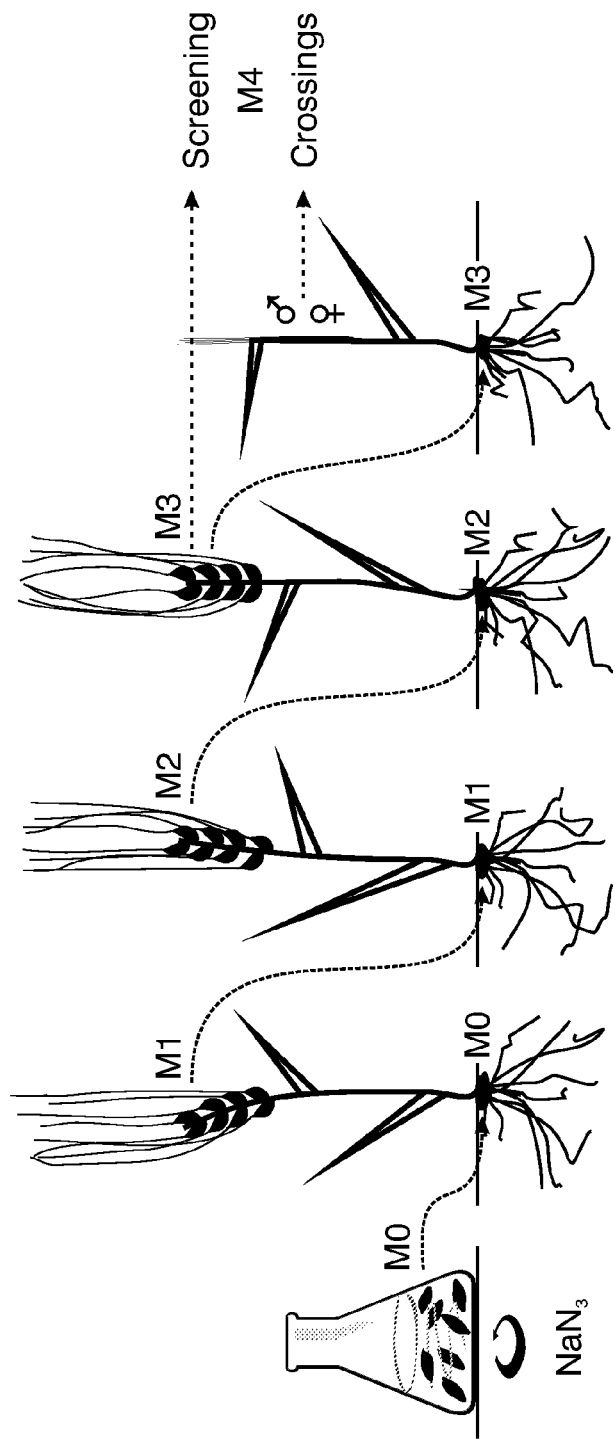
FIG. 1 shows one example on how $NaN_3$-mutagenized barley kernels may be propagated. Kernels of generation M0 grow into plants that develop kernels of generation M1. These may be sown for development into M1 plants, which produce new kernels of generation M2. Next, M2 plants grow and set kernels of generation M3. Kernels of generation M3 may be allowed to germinate, for example for analysis of coleoptiles of the germinated M3 plants. Additionally, flowers derived from kernels of M3 plants may be used in crossings with barley lines or cultivars to obtain plants of generation M4. A similar figure is presented as FIG. 1A in PCT patent application WO 2005/087934 to Breddam, K. et al.

In the description, figures, and tables that follow, a number of terms are used. In order to provide the specifications and claims, including the scope to be given such terms, the following definitions are provided:

As used herein, "a" can mean one or more, depending on the context in which it is used.

The term "agronomic trait" describes a phenotypic or genetic trait of a plant that contributes to the performance or economic value of said plant. Such traits include disease resistance, insect resistance, virus resistance, nematode resistance, drought tolerance, high salinity tolerance, yield, plant height, days to maturity, kernel grading (i.e. kernel size fractionation), kernel nitrogen content and the like.

By "antisense nucleotide sequence" is intended a sequence that is in inverse orientation to the normal coding 5'-to-3' orientation of that nucleotide sequence. When present in a plant cell, the antisense DNA sequence preferably reduces normal expression of the nucleotide sequence for the endogenous gene, and may disrupt production of the corresponding, native protein. In barley plants expression of antisense nucleotides in general only reduces expression but does not prevent expression of said native protein.

The term "barley" in reference to the process of making beer and barley-based beverages, particularly when used to describe the malting process, means barley kernels. In all other cases, unless otherwise specified, "barley" means the barley plant (Hordeum vulgare, L.), including any breeding line or cultivar or variety, whereas part of a barley plant may be any part of a barley plant, for example any tissue or cells.

By "disease resistance" is intended that the plants avoid disease symptoms, which are the outcome of plant-pathogen interactions. In this way, pathogens are prevented from causing plant diseases and the associated disease symptoms. Alternatively, the disease symptoms caused by the pathogen are minimized or reduced, or even prevented.

As used herein the term "double null-LOX" refers to a total loss of function of LOX-1 activityand a total loss of function of LOX-2 activity. Thus, "double null-LOX" may be characterized by a total loss of functional LOX-1 enzyme and a total loss of functional LOX-2 enzyme. Thus, a "double null-LOX barley plant", is a barley plant comprising a first mutation resulting in a total loss of function of LOX-1 activity and a second mutation resulting in a total loss of function LOX-2 activity. A "double null-LOX barley plant" may thus be characterized by a total loss of functional LOX-1 enzyme and a total loss of functional LOX-2 enzyme. Similarly, "double null-LOX kernels", are kernels comprising a first mutation resulting in a total loss-of-function of LOX-1 activity and a second mutation resulting in a total loss of function of LOX-2 activity, and so forth. "Double null-LOX kernels" may thus be characterized by a total loss of functional LOX-1 enzyme and a total loss of functional LOX-2 enzyme.

A "cereal" plant, as defined herein, is a member of the Graminae plant family, cultivated primarily for their starch-containing seeds or kernels. Cereal plants include, but are not limited to barley (Hordeum), wheat (Triticum), rice (Oryza), maize (Zea), rye (Secale), oat (Avena), sorghum (Sorghum), and Triticale, a rye-wheat hybrid.

By "encoding" or "encoded", in the context of a specified nucleic acid, is meant comprising the information for translation into the specified protein. A nucleic acid or polynucleotide encoding a protein may comprise non-translated sequences, e.g. introns, within translated regions of the nucleic acid, or may lack such intervening non-translated sequences, e.g. in cDNA. The information by which a protein is encoded is specified by the use of codons.

As used herein, "expression" in the context of nucleic acids is to be understood as the transcription and accumulation of sense mRNA or antisense RNA derived from a nucleic acid fragment. "Expression" used in the context of proteins refers to translation of mRNA into a polypeptide.

The term "gene" means the segment of DNA involved in producing a polypeptide chain; it includes regions preceding and following the coding region (promoter and terminator). Furthermore, plant genes generally consist of exons interrupted by introns. After transcription into RNA, the introns are removed by splicing to generate a mature messenger RNA (mRNA). The "splice sites" between exons and introns are typically determined by consensus sequences acting as splice signals for the splicing process, consisting of a deletion of the intron from the primary RNA transcript and a joining or fusion of the ends of the remaining RNA on either side of the excised intron. In some cases, alternate or different patterns of splicing can generate different proteins from the same single stretch of DNA. A native gene may be referred to as an "endogenous gene".

As used herein, "heterologous" in reference to a nucleic acid is a nucleic acid that originates from a foreign species, or, if from the same species, is substantially modified from its native form in composition and/or genomic locus by deliberate human intervention.

The term "germination" as used herein means the beginning or resumption of growth by a barley kernel in various compositions, such as normal soil as found in nature. Thus, a germinating embryo is an embryo undergoing germination. Germination can also take place in the soil of pots placed in growth chambers an the like, or for example take place on wet filter paper placed in standard laboratory Petri dishes or during malting (for example, in steep tanks or germination boxes of the malting factory). Germination is generally understood to include hydration of the kernels, swelling of the kernels and inducing growth of the embryo. Environmental factors affecting germination include moisture, temperature and oxygen level. Root and shoot development is observed.

As used herein, the term "isolated" means that the material is removed from its original environment. For example, a naturally occurring polynucleotide or polypeptide present in a living organism is not isolated, but the same polynucleotide or polypeptide, separated from some or all of the coexisting materials in the natural system, is isolated.

Such polynucleotides could be part of a vector and/or such polynucleotides or polypeptides could be part of a composition, and still be isolated because such vector or composition is not part of its natural environment.

The term "kernel" is defined to comprise the cereal caryopsis, also denoted internal seed, the lemma and palea. In most barley varieties, the lemma and palea adhere to the caryopsis and are a part of the kernel following threshing. However, naked barley varieties also occur. In these, the caryopsis is free of the lemma and palea and threshes out free as in wheat. The terms "kernel" and "grain" are used interchangeably herein.

"Grain development" refers to the period starting with fertilization of the egg cell by a pollen cell. During fertilization metabolic reserves—e.g. sugars, oligosaccharides, starch, phenolics, amino acids, and proteins—are deposited, with and without vacuole targeting, to various tissues in the kernel (grain) endosperm, testa, aleurone, and scutellum, thus leading to kernel (grain) enlargement, kernel (grain) filling, and ending with kernel (grain) desiccation.

The term "total loss of function" refers to the lack of the given enzymatic activity. Thus a barley plant with a "total loss of function" of LOX-1 and LOX-2 activity is a barley plant with no detectable LOX-1 and LOX-2 activities. In the context of the present invention, LOX-1 and LOX-2 activities are determined by an assay procedure determining the formation of 9-HPODE and 13-HPODE from linoleic acid, even though LOX-1 and LOX-2 may have other activities. Preferably, formation of 9-HPODE and 13-HPODE from linoleic acid is determined as described in Example 4 herein below. The activity should be determined using protein extracts of germinated embryos. In the context of the present invention, generation of a chromatogram peak corresponding to less than 5%, preferably less than 3% of the 9-HPODE peak of the standard shown in FIG. 5A, and/or a peak corresponding to less than 5%, preferably less than 3% of the 13-HPODE peak of the standard shown in FIG. 5A, when using linoleic acid as substrate, is considered as no detectable LOX-1 and LOX-2 activity, when using the assay described in Example 4. Molecular approaches to obtain a total loss of function of LOX activity comprise generation of mutations that either cause a total absence of transcripts for said enzyme, total absence of the corresponding encoded enzyme, or mutations that totally inactivate the encoded enzyme.

Figure 2:
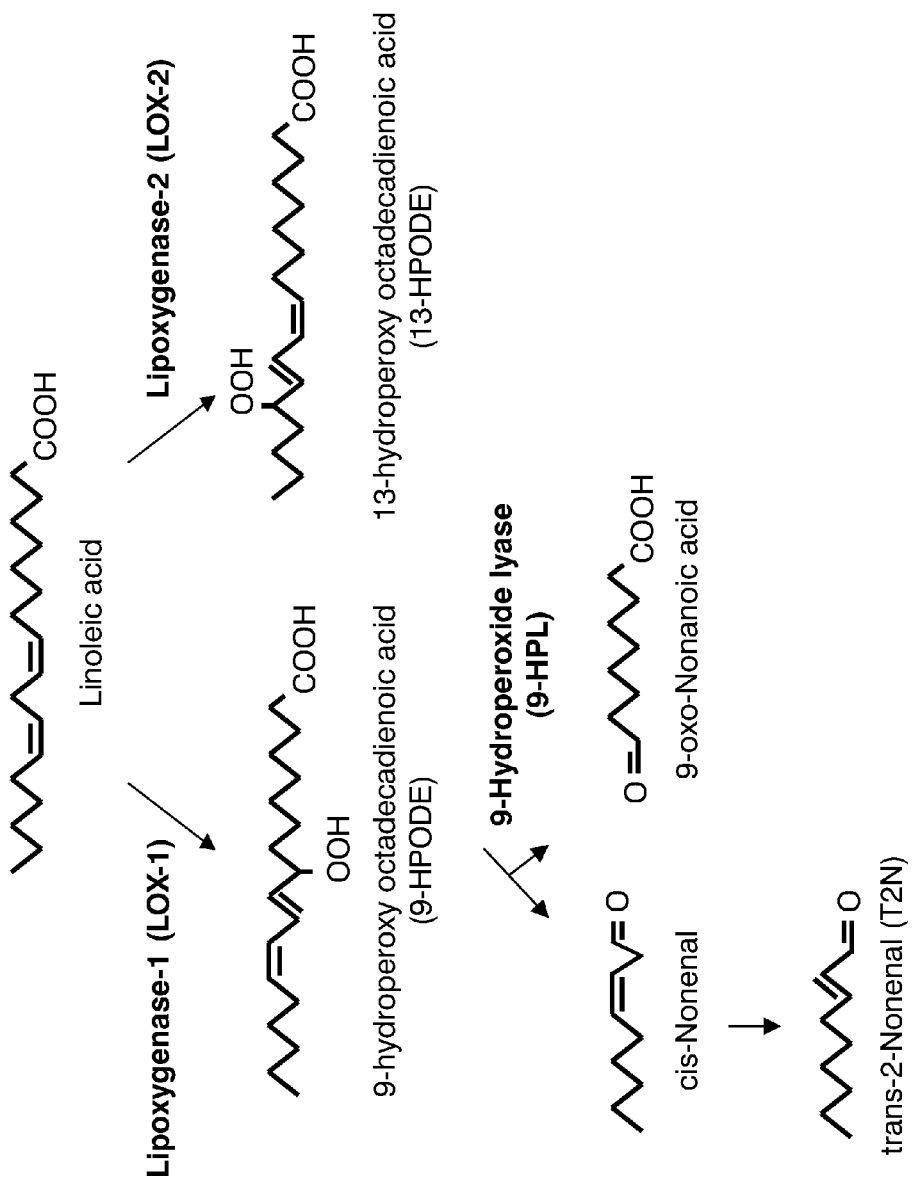
FIG. 2 shows a schematic illustration of a biochemical pathway for conversion and degradation of linoleic acid to T2N. LOX-1 primarily catalyzes the conversion of linoleic acid to 9-HPODE, which is enzymatically degraded to cis-nonenal. This compound undergoes a spontaneous, chemical isomerization to T2N. LOX-2 primarily catalyzes the conversion of linoleic acid into 13-HPODE, which may be converted into 2-E-hexanal (not shown).

The term "LOX-1 activity" refers to the enzymatic activity of the barley LOX-1 enzyme. Particularly, in the context of the present invention, "LOX-1 activity" is the enzyme-catalyzed dioxygenation of linoleic acid to 9-HPODE, and to a much lesser extent 13-HPODE. Even though the LOX-1 enzyme is capable of catalyzing other reactions, for the purpose of determining the activity of LOX-1 according to the present invention, only the 9- and 13-HPODE forming activities should be considered. FIG. 2 outlines the biochemical pathway wherein linoleic acid is converted to 9-HPODE.

The term "LOX-2 activity" refers to the enzymatic activity of the barley LOX-2 enzyme. Particularly, in the context of the present invention, "LOX-2 activity" is the enzyme-catalyzed dioxygenation of linoleic acid to 13-HPODE, and to a much lesser extent 9-HPODE. Even though the LOX-2 enzyme is capable of catalyzing other reactions, for the purpose of determining the activity of LOX-2 according to the present invention, only the 13- and 9-HPODE forming activities should be considered. FIG. 2 outlines the biochemical pathway wherein linoleic acid is converted to 13-HPODE.

The term "malt beverage" or the term "malt based beverage" refer to beverages prepared using malt, preferably beverages prepared by a method including a step of incubating malt with hot water. Malt beverage may, for example, be beer or maltinas.

The term "fermented malt beverage" refers to malt beverages, which have been fermented, i.e. incubated with yeast.

"Malting" is a special form of germination of barley kernels taking place under controlled environmental conditions—including, but not limited to steep tanks and germination boxes of the malting factory. In accordance with the process of the present invention, malting begins to occur during and/or after the barley kernels have been steeped. The malting process may be stopped by drying of the barley kernels, for example, in a kiln drying process. In case that the malt has not been kiln dried, it is denoted "green malt". A malt composition prepared from double null-LOX barley is understood to comprise double null-LOX malt, such as pure double null-LOX malt, or any blend of malt comprising double null-LOX malt. Malt may be processed, for example, by milling and thus referred to as "milled malt" or "flour".

"Mashing" is the incubation of milled malt in water. Mashing is preferably performed at a specific temperature, and in a specific volume of water. The temperature and volume of water are of importance, as these affect the rate of decrease of enzyme activity derived from the malt, and hence especially the amount of starch hydrolysis that can occur; protease action may also be of importance. Mashing can occur in the presence of adjuncts, which is understood to comprise any carbohydrate source other than malt, such as, but not limited to, barley (including double null-LOX barley), barley syrups, or maize, or rice—either as whole kernels or processed products like grits or starch. All of the aforementioned adjuncts may be used principally as an additional source of extract (syrups are typically dosed during wort boiling). The requirements for processing of the adjunct in the brewery depend on the state and type of adjunct used, and in particular on the starch gelatinization or liquefaction temperatures. If the gelatinization temperature is above that for normal malt saccharification, then starch is gelatinized and liquefied before added to the mash.

"Mutations" include deletions, insertions, substitutions, transversions, and point mutations in the coding and noncoding regions of a gene. Deletions may be of the entire gene, or of only a portion of the gene, wherein the noncoding region preferably is either the promoter region, or the terminator region, or introns. Point mutations may concern changes of one base or one base pair, and may result in stop codons, frameshift mutations or amino acid substitutions. Somatic mutations are those which occur only in certain cells or tissues of the plant and are not inherited to the next generation. Germline mutations can be found in any cell of the plant and are inherited. With reference to FIG. 1 herein—which presents an overview on how grains of mutated barley may be propagated in a breeding program—grains of generation M3, and directly propagated grains thereof, or of any subsequent generation, including the plants thereof, may be termed "raw mutants". Further, still with reference to FIG. 1 herein, the term "breeding line" refers to grains of generation M4, and any subsequent generation, including the plants thereof, which may be the result of a cross to a cultivar plant, or the result of a cross to another breeding line with a separate, specific trait.

The term "null-LOX" refers to the presence of a mutation in a LOX-encoding gene, causing a total loss of function of the encoded LOX enzyme (either LOX-1 or LOX-2). Mutations that generate premature termination (nonsense) codons in a gene encoding LOX represent only one mechanism by which total loss of function of LOX activity can be obtained. Molecular approaches to obtain total loss of function of a LOX enzyme comprise the generation of mutations that cause a total absence of transcripts for said enzyme, or mutations that cause total inactivation of the encoded enzyme. "null-LOX" with reference to a plant refers to a plant having a total loss of function of the specified LOX enzyme.

"Operably linked" is a term used to refer to the association of two or more nucleic acid fragments on a single polynucleotide, so that the function of one is affected by the other. For example, a promoter is operably linked with a coding sequence when it is capable of affecting the expression of that coding sequence, i.e. that the coding sequence is under the transcriptional control of the promoter. Coding sequences can be operably linked to regulatory sequences in sense or antisense orientation.

"PCR" or "polymerase chain reaction" is well known by those skilled in the art as a technique used for the amplification of specific DNA segments (U.S. Pat. Nos. 4,683,195 and 4,800,159 to Mullis, K. B. et al.).

"Plant" or "plant material" includes plant cells, plant protoplasts, and plant cell tissue cultures from which barley plants can be regenerated—including plant calli, and plant cells that are intact in plants, or parts of plants, such as embryos, pollen, ovules, flowers, kernels, leaves, roots, root tips, anthers, or any part or product of a plant.

By the term "plant product" is meant a product resulting from the processing of a plant or plant portion. Said plant product may thus, for example, be malt, wort, a fermented or non-fermented beverage, a food, or a feed product.

As used herein, "recombinant" in reference to a protein is a protein that originates from a foreign species, or, if from the same species, is substantially modified from its native form in composition by deliberate human intervention.

A "specialist beer taste panel" within the meaning of the present application is a panel of specialists extensively trained in tasting and describing beer flavors, with special focus on aldehydes, papery taste, and old taste. Although a number of analytical tools exist for evaluating flavor components, the relative significance of flavor-active components are difficult to assess analytically. However, such complex properties can be evaluated by taste specialists. Their continuous training includes tasting and evaluation of standard beer samples.

By the term "splice site" is meant the boundaries between exons and introns of a gene. Thus, a splice site may be the border going from exon to intron (called a "donor site"), or the border separating intron from exon (denoted "acceptor site"). A splice site in plants typically comprises consensus sequences. The 5' end of an intron, in general, consists of a conserved GT dinucleotide (GU in the mRNA), and the 3' end of an intron usually consists of a conserved dinucleotide AG. The 5' splice site of an intron thus comprises the 5' end of an intron, and the 3' splice site comprises the 3' end of an intron. Preferably, within the context of the present invention, the splice site of an intron is either the 5' splice site consisting of the most 5' dinucleotides of the intron (which in general is GT), or the 3' splice site consisting of the most 3' dinucleotides of the intron (which in general is AG).

Unless otherwise noted, "T2N" means trans-2-nonenal (T2N) in the free form. T2N is sometimes also referred to as 2-E-nonenal.

By the term "T2N potential" is described the chemical substances which have the capacity to release T2N, or be converted into T2N, in one or more reactions. In the present context, the T2N potential is defined as the concentration of T2N released into a solution, e.g. wort or beer, during incubation for 2 h at 100° C., pH 4.0. In practical terms, the starting T2N concentration is determined, after which the solution is incubated for 2 h at 100° C., pH 4.0, followed by determination of the T2N concentration. The difference between the starting and the end T2N concentration is denoted the T2N potential. The thermal, acidic treatment causes liberation of T2N from the T2N potential, e.g. from "T2N adducts", the latter term used to describe T2N conjugated to one or more substances, including, but not limited to protein(s), sulfite, cellular debris, cell walls, or the like. In general, T2N adducts per se are not sensed by humans as off-flavors. However, T2N released from said T2N adducts may give rise to an off-flavor.

"Tissue culture" indicates a composition comprising isolated cells of the same or different types, or a collection of such cells organized into parts of a plant—including, for example, protoplasts, calli, embryos, pollen, anthers, and the like.

"Transformation" means introducing DNA into an organism so that the DNA is maintained, either as an extrachromosomal element (without integration and stable inheritance), or as a chromosomal integrant (genetically stable inheritance). Unless otherwise stated, the method used herein for transformation of *E. coli* was the $CaCl_2$-based method (Sambrook and Russel, supra). For transformation of barley, *Agrobacterium*-mediated transformation may be performed—preferentially as described by either Tingay et al. (1997), or Wang et al. (2001), except that alternative cultivars may be used as host.

A "transgene" is a gene that has been introduced into the genome by a transformation procedure.

As used herein, "transgenic" includes reference to a cell that has been modified by the introduction of a heterologous nucleic acid, or that the cell is derived from a cell so modified. Thus, for example, transgenic cells express genes that are not found in an identical form within the native form of the cell, or express native genes that are otherwise abnormally expressed, under-expressed, or not expressed at all as a result of deliberate human intervention. The term "transgenic" as used herein in reference to plants, particularly barley plants, does not encompass the alteration of the cell by methods of traditional plant breeding—e.g. $NaN_3$-based mutagenesis, or by naturally occurring events without deliberate human invention.

"Wild barley", *Hordeum vulgare* ssp. spontaneum, is considered the progenitor of contemporary cultivated forms of barley. The transition of barley from a wild to a cultivated state is thought to have coincided with domestication of the plant into "barley landraces". These are genetically more closely related to modern cultivars than wild barley.

The term "wild-type" barley refers to a conventionally generated barley plant. Preferably, the term refers to the barley plant from which the barley plants of the instant invention have been derived, i.e the parental plants. Wild-type barley kernels are generally available from, for example, seed companies as "cultivars" or "varieties"—i.e. those genetically similar kernels that are listed by national plant breeding organizations. Despite the availability of several null-LOX-1 barley cultivars (e.g. cvs. Chamonix and Charmay), but for the purpose of a better understanding of the instant invention, all null-LOX-1, null-LOX-2, and double null-LOX plants are herein considered mutant plants, and not wild-type plants. The notations "cultivar" and "variety" are used interchangeably herein.

By the term "wort" is meant a liquid extract of malt, such as milled malt, or green malt, or milled green malt. In barley brewing, wort may also be prepared by incubating an extract of un-malted barley with an enzyme mixture that hydrolyzes the barley components. In addition to said malt or barley-derived extracts, the liquid extract may be prepared from malt and additional components, such as additional starch-containing material partly converted into fermentable sugars. The wort is in general obtained by mashing, optionally followed by "sparging", in a process of extracting residual sugars and other compounds from spent grains after mashing with hot water. Sparging is typically conducted in a lauter tun, a mash filter, or another apparatus to allow separation of the extracted water from spent grains. The wort obtained after mashing is generally referred to as "first wort", while the wort obtained after sparging is generally referred to as the "second wort". If not specified, the term wort may be first wort, second wort, or a combination of both. During beer production, wort is generally boiled together with hops. Wort, which has not been boiled with hops, may also be referred to as "sweet wort", whereas wort boiled with hops may be referred to as "boiled wort".

Barley Plant

Barley is a family of plants. "Wild barley", *Hordeum vulgare* ssp. spontaneum, is considered the progenitor of today's cultivated forms of barley. The transition of barley from a wild to a cultivated state is thought to have coincided with a radical change of allele frequencies at numerous loci. Rare alleles and new mutational events were positively selected for by the farmers who quickly established the new traits in the domesticated plant populations, denoted "barley landraces". These are genetically more closely related to modern cultivars than wild barley. Until the late nineteenth century, barley landraces existed as highly heterogeneous mixtures of inbred lines and hybrid segregates, including few plants derived from random crossings in earlier generations. Most of the landraces have been displaced in advanced agricultures by pure line cultivars. Intermediate or high levels of genetic diversity characterize the remaining landraces. Initially, "modern barley" cultivars represented selections from landraces. These were later derived from successive cycles of crosses between established pure lines, such as those of diverse geographical origins. Eventually, the result was a marked narrowing of the genetic base in many, probably all, advanced agricultures. Compared with landraces, modern barley cultivars have numerous improved properties (Nevo, 1992; von Bothmer et al., 1992), for example one or more, but not limited to the following:

(i) Covered and naked kernels;
(ii) Seed dormancy;
(iii) Disease resistance;
(iv) Environmental tolerance (for example to drought or soil pH);
(v) Proportions of lysine and other amino acids;
(vi) Protein content;
(vii) Nitrogen content;
(viii) Carbohydrate composition;
(ix) Hordein content and composition;
(x) (1-3, 1-4)-β-Glucan and arabinoxylan content;
(xi) Yield
(xii) Straw stiffness;
(xiii) Plant height.

Within the present invention, the term "barley plant" comprises any barley plant. Thus, the invention relates to any barley plant comprising a first mutation resulting in a total loss of function of LOX-1 activity, and a second mutation resulting in a total loss of function of LOX-2 activity. Thus the invention relates to any barley plant comprising a first mutation that results in a total loss of functional LOX-1 enzyme and a second mutation resulting in a total loss of functional LOX-2 enzyme.

However, preferred barley plants for use with the present invention are modern barley cultivars or pure lines. The barley cultivar to be used with the present invention may, for example, be selected from the group consisting of Sebastian, Celeste, Lux, Prestige, Saloon, Neruda, Harrington, Klages, Manley, Schooner, Stirling, Clipper, Franklin, Alexis, Blenheim, Ariel, Lenka, Maresi, Steffi, Gimpel, Chem, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett and Jersey preferably from the group consisting of Haruna Nijo, Sebastian, Celeste, Lux, Prestige, Saloon, Neruda and Power, preferably from the group consisting of Harrington, Klages, Manley, Schooner, Stirling, Clipper, Franklin, Alexis, Blenheim, Ariel, Lenka, Maresi, Steffi, Gimbel, Chem, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett and Jersey preferably from the group consisting of Haruna Nijo, Sebastian, Tangent, Lux, Prestige, Saloon, Neruda, Power, Quench, NFC Tipple, Barke, Class and Vintage.

In one embodiment of the invention, the barley plant is accordingly a modern barley cultivar (preferably a cultivar selected from the group of barley cultivars described herein above) comprising a first mutation resulting in a total loss of function of LOX-1 asctivity, such as total loss of functional LOX-1 enzyme, and a second mutation resulting in a total loss of function of LOX-2 activity, such as total loss of functional LOX-2 enzyme. In this embodiment, it is thus preferred that the barley plant is not a barley landrace.

The barley plant may be in any suitable form. For example, the barley plant according to the invention may be a viable barley plant, a dried plant, a homogenized plant, or a milled barley kernel. The plant may be a mature plant, an embryo, a germinated kernel, a malted kernel, a milled malted kernel, or the like.

Parts of barley plants may be any suitable part of the plant, such as kernels, embryos, leaves, stems, roots, flowers, or fractions thereof. A fraction may, for example, be a section of a kernel, embryo, leaf, stem, root, or flower. Parts of barley plants may also be a fraction of a homogenate, or a fraction of a milled barley plant or kernel.

In one embodiment of the invention, parts of barley plants may be cells of said barley plant, preferably viable cells that may be propagated in vitro in tissue cultures. In particular, said cells in one embodiment may be cells that are not capable of maturing into an entire barley plant, i.e. cells that are not a reproductive material.

Loss of Function of LOX Activity

The present invention relates to barley plants—or part thereof, or plant products thereof—having a first and a second mutation, wherein the first mutation leads to a total loss of function of LOX-1 activity, and the second mutation leads to a total loss of function of LOX-2 activity. Thus, for example, the first mutation leads to a total loss of functional LOX-1 enzyme, and the second mutation leads to a total loss of functional LOX-2 enzyme.

The total loss of function of LOX-1 activity (such as the total loss of functional LOX-1 enzyme, and the total loss of function of LOX-2 activity (such as the total loss of functional LOX-2 enzyme), may independently be based on different mechanisms. For example, the total loss of function of one or both of LOX-1 activity and LOX-2 activity may be caused by malfunctioning proteins in the barley plant, i.e. a malfunctioning LOX-1 and/or LOX-2 protein, such as a mutated LOX-1 protein with no detectable 9-HPODE—forming activity (for example determined as described in Example 4), and/or a mutated LOX-2 protein with no detectable 13-HPODE forming activity (for example determined as described in Example 4).

The total loss of function of one or both of LOX-1 activity and LOX-2 activity may be caused by the lack of LOX-1 and/or LOX-2 protein. It is apparent that lack of LOX-1 protein will lead to loss of functional LOX-1 enzyme, and that lack of LOX-2 protein will lead to total loss of functional LOX-2 enzyme. Thus, the barley plant may preferably comprise no—or only very little, more preferably no detectable—LOX-1 and/or LOX-2 protein. The LOX-1 and/or LOX-2 protein may be detected by any suitable means known to the person skilled in the art. Preferably, however, the protein(s) is detected by techniques wherein LOX-1 protein is detected by specific antibodies to LOX-1 and LOX-2, such as polyclonal antibodies to LOX-1 and LOX-2. Said techniques may, for example, be Western blotting or ELISA. Said antibodies may be monoclonal or polyclonal. Preferably, however, said antibodies are of a polyclonal nature, recognizing several different epitopes within the LOX-1 and LOX-2 protein, respectively. LOX-1 and/or LOX-2 protein may also be detected indirectly, for example, by methods determining LOX-1 activity, or by methods determining LOX-2 activity. In one preferred embodiment of the invention, LOX-1 protein is detected using the methods outlined in Example 4 of the international patent application WO 2005/087934. LOX-2 protein may be detected in a similar manner, using antibodies binding to LOX-2.

The total loss of function of one or both of LOX-1 activity and LOX-2 activity may also be a result of no, or very little, preferably no expression of a LOX-1 transcript and/or a LOX-2 transcript. The skilled person will acknowledge that the absence of a LOX-1 or a LOX-2 transcript also will result in the absence of translated LOX-1 or LOX-2 protein, respectively. Alternatively, the total loss of function of one or both of LOX-1 activity and LOX-2 activity (e.g. the total loss of functional LOX-1 and LOX-2 enzymes), may also be a result expression of an aberrant LOX-1 transcript and/or an aberrant LOX-2 transcript. An aberrant LOX-1 and/or LOX-2 transcript may be caused by aberrant splicing of the transcript, for example, due to a mutation in a splice site. Thus, the barley plants of the invention may carry a mutation in the a splice site, such as a 5' splice site or a 3' splice site, for example in one or the two most 5' nucleotides of an intron, or in one of the most 3' nucleotides of an intron. An example of a mutant with an aberrant splicing of the LOX-1 transcript is described as mutant A618 in WO 2005/087934. Expression of transcripts encoding LOX-1 or LOX-2 may, for example, be detected by Northern blotting or RT-PCR experiments.

The total loss of functional LOX-1 and LOX-2 enzymes of the barley plants of the present invention is caused by mutations. Thus, the barley plants of the present invention in general carry a mutation in the LOX-1 gene. Said mutation may be in the regulatory regions, for example within the promoter or introns, or said mutation may be in the coding region. Similarly, the barley plants of the present invention in general carry a mutation in the LOX-2 gene. Said mutation may be in the regulatory regions, for example within the promoter or introns, or said mutation may be in the coding region. Thus, the cause of the total loss of functional LOX-1 and/or LOX-2 enzymes may also be detected by the identification of mutations in the gene encoding LOX-1, or in the gene encoding LOX-2. Mutations in the gene encoding LOX-1 may, for example, be detected by sequencing said gene. Preferably, after identifying a mutation, the total loss of function is confirmed by testing for LOX-1 and/or LOX-2 activities.

The term "LOX-1 protein" is meant to cover the full-length LOX-1 protein of barley as set forth in SEQ ID NO:3 of WO 2005/087934, or in SEQ ID NO:7 of WO 2005/087934, or a functional homolog thereof. The active site of LOX-1 is situated in the C-terminal part of the enzyme. In particular, it is anticipated that the region spanning amino acid residues 520-862, or parts thereof, are relevant for LOX-1 activity. Accordingly, in one embodiment, null-LOX-1 barley preferably comprises a gene that encodes a mutated form of LOX-1, lacking some or all of amino acids 520-862 of LOX-1. Said mutated LOX-1 may also lack other amino acid residues, which are present in wild-type LOX-1.

Accordingly, double null-LOX barley of the invention may comprise a truncated form of LOX-1, which is not functional—such as an N- or a C-terminal truncated form. Preferably, said truncated form comprises no more than 800, more preferably no more than 750, even more preferably no more than 700, yet more preferably no more than 690, even more preferably no more than 680, yet more preferably no more than 670 consecutive amino acids of LOX-1, such as no more than 665, for example no more than 650, such as no more than 600, for example no more than 550, such as no more than 500, for example no more than 450, such as no more than 425, for example no more than 399 consecutive amino acids of LOX-1 of SEQ ID NO:3 of WO 2005/087934. Preferably, said truncated form comprises only an N-terminal fragment of LOX-1, preferably at the most the 800, more preferably at the most the 750, even more preferably at the most the 700, yet more preferably at the most the 690, even more preferably at the most the 680, yet more preferably at the most the 670, even more preferably at the most the 665 N-terminal amino acids of SEQ ID NO:3 of WO 2005/087934, such as no more than 665, for example no more than 650, such as no more than 600, for example at the most the 550, such as at the most the 500, for example at the most the 450, such as at the most the 425, for example at the most the 399 N-terminal amino acids of SEQ ID NO:3 of WO 2005/087934.

In one very preferred embodiment, the truncated form may consist of amino acids 1-665 of SEQ ID NO:3 of WO 2005/087934.

In a preferred embodiment of the invention, the barley plant of the invention comprises a LOX-1-encoding gene that is transcribed into mRNA, which comprises a nonsense codon or a stop codon upstream of the stop codon of wild-type LOX-1 mRNA. Such a nonsense codon is herein denoted a premature nonsense codon. Preferably, all LOX-1-encoding genes transcribed into mRNA of said plant comprise a premature nonsense codon or a stop codon. The nonsense codon or stop codon is preferably situated at the most 800, more preferably at the most the 750, even more preferably at the most the 700, yet more preferably at the most the 690, even more preferably at the most the 680, yet more preferably at the most the 670, even more preferably at the most the 665 codons downstream of the start codon. The sequence of wild-type genomic DNA encoding LOX-1 is given in SEQ ID NO:1 of WO 2005/087934 (re-presented as SEQ ID No:12 herein) or SEQ ID NO:5 of WO 2005/087934.

In one preferred embodiment, the barley plant of the invention comprises a gene encoding LOX-1, wherein the pre-mRNA transcribed from said gene comprises the sequence corresponding to SEQ ID NO:2 of WO 2005/087934 (re-presented as SEQ ID NO:13 herein).

In a very preferred embodiment of the invention, the gene encoding mutant LOX-1 of the double null-LOX barley plant according to the invention comprises a nonsense mutation, said mutation corresponding to a G→A substitution at position 3574 of SEQ ID NO:1 of WO 2005/087934.

The term "LOX-2 protein" is meant to cover the full-length LOX-2 protein of barley as set forth in SEQ ID NO:5 of the instant publication, or a functional homolog thereof. The active site of LOX-2 is situated in the C-terminal part of LOX-2. In particular, it is anticipated that the region spanning amino acid residues 515-717, or parts thereof, are relevant for LOX-2 activity. Based on an examination of the soybean LOX-1 crystal structure, anticipated sequence stretches of the active site cleft of the LOX-2 enzyme of barley are represented by amino acid residues 515-525 and 707-717. A translated, mutated LOX-2 protein, i.e. a C-terminally truncated form of LOX-2 of barley double null-LOX mutant A689 contains max. 684 residues, and will therefore lack the second sequence stretch of the active site cleft—making it inactive. According to one embodiment of the invention, double null-LOX barley of the invention preferably comprises a gene encoding a mutant form of LOX-2 that lacks some, or all, of amino acids 515-717 of LOX-2, preferably lacking some or all of amino acids 707 to 717, even more preferably lacking all of amino acids 707-717. Said mutant LOX-2 may also lack other amino acid residues, which are present in wild-type LOX-2.

Accordingly, double null-LOX barley may comprise a truncated form of LOX-2, which is not functional, such as an N-terminal or a C-terminal truncated form. Preferably, said truncated form comprises no more than 800, more preferably no more than 750, even more preferably no more than 725, yet more preferably no more than 700, even more preferably no more than 690, yet more preferably no more than 684 consecutive amino acids of LOX-2 of SEQ ID NO:5 of the instant publication. Preferably, said truncated form comprises only an N-terminal fragment of LOX-2. Hence, preferably said truncated form comprises at the most the 800, more preferably at the most the 750, even more preferably at the most the 725, yet more preferably at the most the 700, even more preferably at the most the 690, yet more preferably at the most the 684 N-terminal amino acids of SEQ ID NO:5 of the instant publication.

In one very preferred embodiment, the truncated form may consist of amino acids 1-684 of SEQ ID NO:5 of the instant publication.

In a preferred embodiment of the invention, the barley plant comprises a gene transcribed into mRNA for LOX-2, wherein said mRNA comprises a nonsense codon or a stop codon upstream of the stop codon of wild-type LOX-2 mRNA. Such a nonsense codon is herein designated a premature nonsense codon. Preferably all genes transcribed into mRNA encoding LOX-2 of said plant comprise a premature nonsense codon or a stop codon. The nonsense codon or stop codon is preferably situated at the most 800, more preferably at the most the 750, even more preferably at the most the 725, yet more preferably at the most the 700, even more preferably at the most the 690, yet more preferably at the most the 684 codons downstream of the start codon. The sequence of wild-type genomic DNA encoding LOX-2 is given in SEQ ID NO:1 of the instant publication.

In a very preferred embodiment of the invention, the gene encoding mutated LOX-2 of the double null-LOX barley plant comprises a nonsense mutation, said mutation corresponding to a G→A substitution at position 2689 of SEQ ID NO:1.

The barley plant according to the invention may be prepared by any suitable method known to the person skilled in the art, preferably by one of the methods outlined herein below in the section "Preparing double null-LOX barley".

In one embodiment of the invention, it is preferred that the double null-LOX barley plant according to the present invention has plant growth physiology and grain development similar to that of wild-type barley. It is hence preferred that the null-LOX-1 barley plant is similar to wild-type barley with respect to plant height, number of tillers per plant, onset of flowering, and/or number of grains per spike.

Also, it is preferred that the double null-LOX barley plant according to the present invention is similar to wild-type barley, in particular similar to cv. Barke with respect to plant height, heading date, disease resistance, lodging, ear-breakage, maturation time, and yield. In the present context, "similar" is to be understood as the same ±10% in case of numbers. These parameters may be determined as described hereinafter in Example 5.

In a very preferred embodiment of the invention, the barley plant is the barley plant wherein seeds thereof have been deposited 4 Dec. 2008 under the name "Barley, *Hordeum vulgare* L.; Line A689" with American Type Culture Collection (ATCC), Patent Depository, 10801 University Blvd., Manassas, Va. 20110, United States (deposit number PTA-9640). Thus, the barley plant of the invention may be barley Line A689 (ATCC Patent Deposit Designation: PTA-9640), or any progeny barley plant thereof.

Preparing Barley Mutants

The barley plant according to the invention may be prepared by any suitable method known to the person skilled in the art. Preferably, the barley plant of the invention is prepared by a method comprising the steps of mutagenizing barley plants or parts thereof, for example barley kernels, followed by screening and selecting barley plants characterized by a total loss of function of LOX-1 activity, such as total loss of functional LOX-1 enzyme and a total loss of function of LOX-2 activity, such as total loss of functional LOX-2 enzyme. In one preferred embodiment, the barley plant may be prepared by a method involving mutagenizing barley plants, or parts thereof—for example barley kernels, wherein said barley plants already carry a mutation causing a total loss of functional LOX-1 enzyme. Such barley plants are, for example, described in international patent application WO 2005/087934.

In one interesting aspect, the present invention relates to a new and very efficient screening method that allows the identification of a barley plant carrying a mutation, which causes total loss of LOX-2 activity. The new, reproducible screening method allows the identification of barley plants with no or very little LOX-2 activity. This new screening method includes the use of germinated embryos as starting material. Interestingly, the present inventors have found that the use of mature embryos as starting material for a screening for LOX-2 activity is less preferable, based on the screening of as many as 21,000 mature embryos, which did not reveal a single null-LOX-2 barley mutant.

Thus, one important feature of the new screening method concerns the utilization of germinated embryos as starting material for detection of LOX-2 activity.

Accordingly, it is an objective of the present invention to provide methods of preparing a double null-LOX barley plant comprising the steps of:
 (i) Providing a barley plant, or parts thereof, with a total loss of function of LOX-1 activity, such as total loss of functional LOX-1 enzyme; and
 (ii) Mutagenizing said barley plant, and/or barley cells, and/or barley tissue, and/or barley kernels, and/or barley embryos from said barley plant, thereby obtaining generation M0 barley; and
 (iii) Breeding said mutagenized barley plants, kernels, and/ or embryos for at least 2 generations, thereby obtaining generation Mx barley plants, wherein x is an integer ≥2; and
 (iv) Obtaining embryos from said Mx barley plants; and
 (v) Germinating said embryos; and
 (vi) Determining the LOX-1 and LOX-2 activities in said germinated embryos, or parts thereof; and
 (vii) Selecting plants with a total loss of LOX-1 activity and LOX-2 activity in the germinated embryos; and
 (viii) Analyzing for a mutation in the LOX-1 gene and in the LOX-2 gene; and
 (ix) Selecting plants carrying a mutation in the LOX-1 gene and the LOX-2 gene;
thereby obtaining a barley plant carrying mutations in the genes for LOX-1 and LOX-2, causing a total loss of LOX-1 activity and a total loss of LOX-2 activity.

The aforementioned barley plant with a total loss of LOX-1 activity may, for example, be any of the barley plants with a total loss of LOX-1 activity described in WO 2005/087934, preferably mutant D112, or progeny plants thereof.

Step (ii) in the aforementioned list may involve mutagenizing living material selected from the group consisting of barley plants, barley cells, barley tissue, barley kernels, and barley embryos—preferably selected from the group consisting of barley plants, barley kernels, and barley embryos, more preferably barley kernels.

Mutagenesis may be performed by any suitable method. In one embodiment, mutagenesis is performed by incubating a barley plant, or a part thereof—for example barley kernels or individual cells from barley—with a mutagenizing agent. Said agent is known to the person skilled in the art, including, for example, but not limited to, sodium azide ($NaN_3$), ethyl methanesulfonate (EMS), azidoglycerol (AG, 3-azido-1,2-propanediol), methyl nitrosourea (MNU), and maleic hydrazide (MH).

In another embodiment, mutagenesis is performed by irradiating, for example by UV, a barley plant or a part thereof, such as the kernel. In preferred embodiments of the invention, the mutagenesis is performed according to any of the methods outlined herein below in the section "Chemical mutagenesis." A non-limiting example of a suitable mutagenesis protocol is given in Example 2.

It is preferred that the mutagenesis is performed in a manner such that the expected frequency of desired mutants is at least 0.5, such as in the range of 0.5 to 5, for example in the range of 0.9 to 2.3 per 10,000 grains, when screening barley of generation M3. In a preferred embodiment, mutagenesis is performed on barley kernels. The kernels applied to the mutagen are designated as generation M0 (see also FIG. 1).

The LOX activity may be determined in a sample from a germinating barley embryo, preferably in a liquid extract from a germinating barley embryo. Said sample, such as said extract may be prepared from any suitable part of said germinating embryo. In general, the barley sample must be homogenized using any suitable method prior to preparation of an extract of said sample and determination of LOX-2 activity. In particular, it is preferred that a protein extract is prepared from the germinating embryo, or part thereof, and that the LOX activity is determined using said protein extract. Homogenization may, for example, be performed using mechanical forces, for example by shaking or stirring, such as by shaking in the presence of a bead, such as a glass or a sand bead.

In a preferred embodiment, the germinating embryo is of generation Mx, wherein x is an integer ≥2; preferably x is an integer in the range of 2 to 10, more preferably in the range of 3 to 8. In a very preferred embodiment, LOX activity is determined in germinating embryos of generation M3, or a sample derived from such embryos. In that embodiment, it is preferred that mutagenized barley kernels of generation M0 are grown to obtain barley plants, which are crossed to obtain kernels of generation M1. The procedure is repeated until kernels of generation M3 are available (see also FIG. 1).

Determination of LOX activity may be carried out using any suitable assay, preferably by one of the methods outlined hereinafter. In particular, it is preferred that the assay provides data on the dioxygenation of linoleic acid to 9-HPODE and 13-HPODE by LOX-1 and LOX-2. In general, assaying will therefore involve the steps of:
 (i) Providing a protein extract prepared from a germinated barley embryo or part thereof; and
 (ii) Providing linoleic acid; and
 (iii) Incubating said protein extract with said linoleic acid; and
 (iv) Detecting dioxygenation of linoleic acid to 9-HPODE and 13-HPODE.

Step (iv) of the method preferably comprises determining the level of 9-HPODE and 13-HPODE in said germinating embryos, preferably in a protein extract prepared from said germinating embryos. The step may comprise a direct or an indirect determination of the levels of 9-HPODE and 13-HPODE. The total level of all HPODEs may be determined, in which case it is preferred that specific measurements of 9-HPODE and 13-HPODE are performed for confirmation. One method could, for example, be a method wherein protein extracts from germinating embryos are incubated with linoleic acid as substrate for formation of 9-HPODE and 13-HPODE. Said HPODEs can then be detected by various methods. One method may involve generation of a detectable compound, such as a dye. For example the method may be the oxidative coupling of 3-dimethylaminobenzoic acid and 3-methyl-2-benzothiazolinone hydrazone in the presence of hemoglobin, catalyzed by the formed HPODEs to form the indamine dye, which can be measured at $A_{595}$ using a spectrophotometer. An example of such a method is described in Examples 1 and 2 hereinafter. Using this assay, an absorption reading of less than 0.2 $A_{595}$ unit is considered as indicative of the absence of LOX-1 and the absence of LOX-2 activities. However, a more precise method for determining LOX-1 and LOX-2 activities is to incubate a protein extract from germinating embryos with linoleic acid, followed by determination of 9-HPODE and 13-HPODE contents. 9-HPODE and 13-HPODE contents may, for example, be determined using HPLC-based analysis.

Dioxygenation of linoleic acid to 9-HPODE and 13-HPODEs may be measured directly or indirectly. Any suitable detection method may be used with the present invention. In one embodiment of the invention, linoleic acid hydroperoxides are detected. 9-HPODE and 13-HPODE may be detected directly, for example, by chromatographic methods, such as HPLC as described in Example 4.

The present invention discloses that certain aspects of the procedure for extraction of protein from the germinating embryo is of great importance. Thus, it is preferred that the protein is extracted using an acidic buffer, preferably a buffer with a pH in the range of 2 to 6, more preferably in the range of 3 to 5, even more preferably in the range of 3.5 to 5, yet more preferably in the range of 4 to 5, even more preferably a pH of 4.5. The buffer used for extraction is preferably based on an organic acid, more preferably a lactic acid buffer. Most preferably, the protein extract is prepared using a 100-mM lactic acid buffer, pH 4.5.

Certain embodiments of the present invention disclose methods for detection of null-LOX-1 and null-LOX-2 plants that involve reaction of 9-HPODE and 13-HPODE with a dye, e.g. 3-methyl-2-benzothiazolinone hydrazone. Preferably, said dye, e.g. 3-methyl-2-benzothiazolinone hydrazone, is added to the protein extract after addition of linoleic acid. Preferably, the dye is added at least 1 min, more preferably at least 5 min, even more preferably at least 10 min, such as in the range of 1 to 60 min, for example in the range of 5 to 30 min, such as in the range of 10 to 20 min after contacting the protein extract with the linoleic acid.

Preferred methods for selecting barley plants according to the invention are detailed hereinafter in Example 2.

The selection procedure may be adjusted for microtitre plate-based assay procedures, or other known repetitive, high-throughput assay formats to allow rapid screening of many samples. It is preferred that at least 5000, such as at least 7500, for example at least 10,000, such as at least 15,000, for example at least 20,000, such as at least 25,000 mutagenized barley plants are analyzed for LOX-1 and LOX-2 activities.

Determination of a mutation in the gene encoding LOX-1 may be performed by several different methods. For example, the LOX-1 gene may be sequenced completely or partly, and the sequence compared to SEQ ID NO:1 of WO 2005/087934 or SEQ ID NO:5 of WO 2005/087934. If searching for a specific mutation, SNP analysis may be applied. The skilled person will be able to design useful primers for detection of a given specific mutation, such as one leading to a premature stop codon in the coding sequence for LOX-1 (e.g. any of the premature stop codons described hereinabove). One example of how to perform a SNP analysis is described in Example 10 hereinbelow, with primers that are useful for detecting a G→A mutation at nucleotide position 3474 of the LOX-1 gene.

Determination of a mutation in the gene encoding LOX-2 may be performed by several different methods. For example, the LOX-2 gene may be sequenced completely or partly, and the sequence compared to SEQ ID NO:1 of the instant publication. If searching for a specific mutation, SNP analysis may be used. The skilled person will be able to design useful primers for detection of a given specific mutation, such as one leading to a premature stop codon in the LOX-2 coding sequence (e.g. any of the premature stop codons described hereinabove). An example of how to perform a SNP analysis is described in Example 10 herein below, as are primers useful for detecting a G→A mutation at nucleotide position 2689 of the gene for LOX-2.

It is also comprised within the present invention that steps (viii) and (ix) of the method of preparing a double null-LOX barley plant, as detailed in this section hereinabove, may be performed prior to steps (vi) and (vii), in which case the method will comprise the steps (i), (ii), (iii), (iv), (v), (viii), (ix), (vi), and (vii) in that order. In particular, this could be the case when searching for a specific mutation, for example in progeny plants of already identified double null-LOX barley plants.

Once a double null-LOX barley plant has been identified, which contains a particular mutation in a LOX-1 gene and a particular mutation in the LOX-2 gene (such as any of the above-mentioned mutations), additional barley plants with the identical mutations may be generated by conventional breeding methods, such as those well known to the skilled person. For example, said double null-LOX barley plant may be backcrossed with another barley cultivar.

Subsequent to the selection of useful barley plants with total loss of LOX-1 and LOX-2 functions, one or more additional screenings may optionally be performed. For example, selected mutants may be further propagated, and plants of new generations may be tested for the total loss of functional LOX-1 and LOX-2 enzymes.

Subsequent to the selection of useful barley plants, these may be subjected to breeding, such as conventional breeding. Methods of breeding are described herein below in the section "Plant breeding".

Plant Products

The present invention relates to beverages, or other plant products, with low levels of T2N potential, prepared from double null-LOX barley plants, or parts thereof.

The present invention thus relates to plant products, which may be compositions comprising the above-described barley plants, or parts thereof, or compositions prepared from said barley plants, or parts thereof, such as plant products prepared from said barley plants, or parts thereof. Because said barley plants lack LOX-1 and LOX-2 activities, the compositions in general comprise very low levels of T2N potential. Examples of useful compositions comprising, or prepared from, barley plants having a first mutation resulting in a total loss of function of LOX-1 activity, such as a total loss of functional LOX-1 enzyme, and a second mutation resulting in a total loss of function of LOX-2 activity, such as total loss of functional LOX-2 enzyme, are described herein below.

It is preferred that said compositions comprise:
 (i) Less than 60%, even more preferably less than 50%, yet more preferably less than 40%, such as less than 30%, preferably less than 20%, more preferably less than 10%, free T2N; and/or
 (ii) Less than 60%, even more preferably less than 50%, yet more preferably less than 40%, such as less than 30%, preferably less than 25% T2N potential;
compared to a similar composition prepared in the same manner from wild-type barley plants, preferably from cv. Power. The specific reduction in T2N may differ depending on the type of composition. Aforementioned reductions in T2N are particularly relevant for compositions, wherein the composition is selected from the group consisting of malt, wort and aged beverages.

In addition, it is preferred that said compositions comprise:
 (i) less than 80%, preferably less than 70%, even more preferably less than 60%, such as less than 50% free T2N; and/or
 (ii) less than 80%, preferably less than 70%, even more preferably less than 60%, such as less than 50% T2N potential;
compared to a similar composition prepared in the same manner from the barley mutant D112 described in WO 2005/087934.

The present invention relates in one aspect to barley kernels having a first mutation that results in a total loss of function of LOX-1 activity (such as total loss of functional LOX-1 enzyme), and a second mutation resulting in a total loss of function of LOX-2 activity (such as total loss of functional LOX-2 enzyme). The present invention also relates to compositions comprising said kernels, and compositions prepared from said kernels, as well as to plant products prepared from said kernels.

It has been described that lipoxygenase activity in barley kernels may be reduced by a soaking process, wherein barley may be subjected to high temperatures and/or lactic acid treatment. Such treatment may have other adverse effects, such as reducing desirable enzymatic activities, e.g. phytase activity. In addition, such treatment only reduces lipoxygenase activity from the point when the heat treatment is undertaken and thus it does not affect the prior accumulation of lipoxygenase products.

Accordingly, in one embodiment the plant products according to the invention are prepared using a method, wherein the barley kernels are not subjected to soaking at a temperature of at least 70° C. It is also preferred that the plant products according to the invention are prepared using a method, wherein the barley kernels are not subjected to soaking at a temperature of at least 57° C. in the presence of lactic acid.

Figure 3:
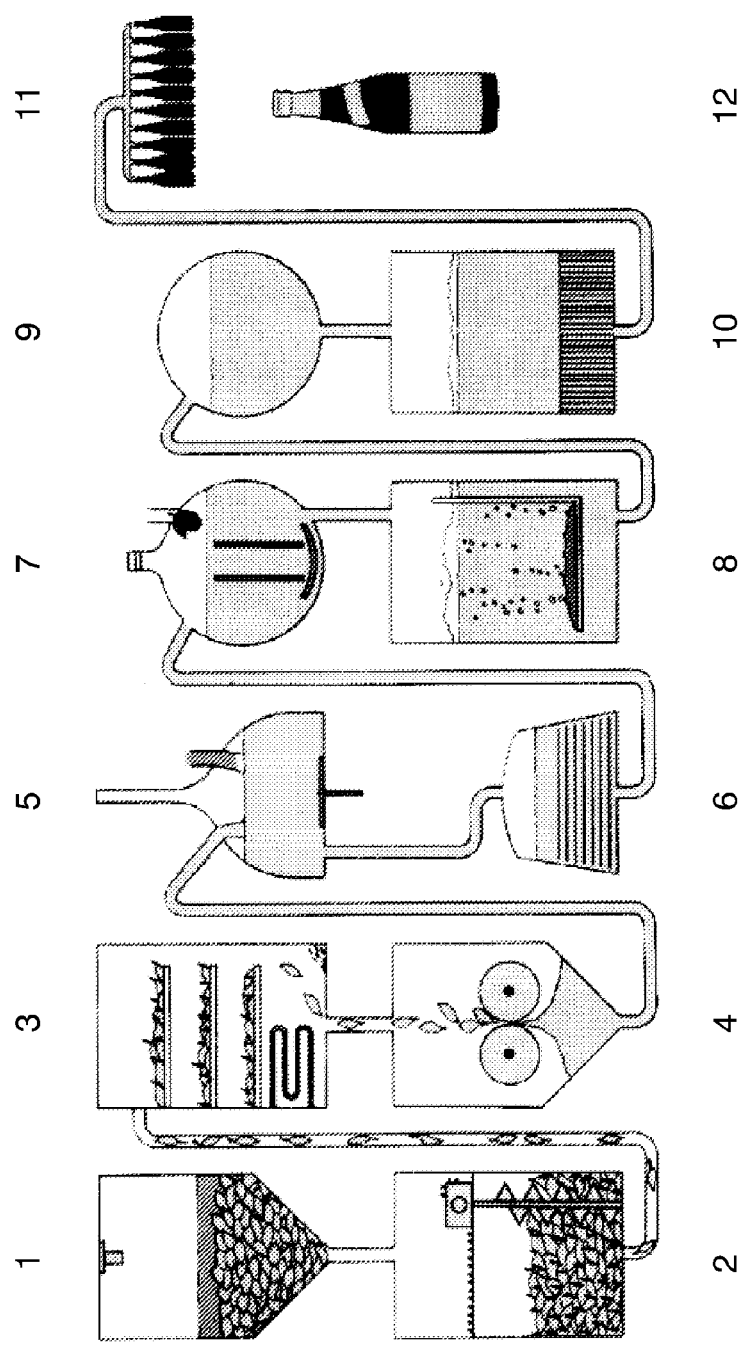
FIG. 3 shows a simplified, schematic overview of a preferred beer production process, including steeping of barley grain (1), malting (2), kiln drying (3), milling of the dried malt (4), mashing (5), filtration (6), wort boiling in the presence of added hops (7), fermentation in the presence of yeast (8), beer maturation (9), beer filtration (10), packaging, such as the packaging into bottles, cans, or the like (11), and labeling (12). The individual processes can be grouped into sections comprising malt production (1-3), wort production (4-7), fermentation (8-9), and the preparation of the finished beer (10-12). Although a preferred method is illustrated, other methods may be envisaged that omit some of the depicted steps (filtration may, for example, be omitted, or hops may not be added—or additional steps may be added, such as addition of adjuncts, sugars, syrups, or carbonate).

In one aspect, the invention relates to malt compositions prepared from double null-LOX kernels by malting. By the term "malting" is to be understood germination of steeped barley kernels taking place under controlled environmental conditions (for example, as illustrated in FIG. 3, steps 2 and 3).

Said malt compositions preferably comprise less than 30%, more preferably less than 20%, even more preferably less than 10% free T2N compared to a malt composition prepared in the same manner from a wild-type barley, preferably from cv. Power. More preferably, said malt compositions comprise less than 60%, more preferably less than 50% free T2N compared to a malt composition prepared in the same manner from the barley null-LOX-1 mutant D112 described in WO 2005/087934. It is furthermore preferred that said malt compositions comprise less than 60%, preferably less than 50%, more preferably less than 40%, even more preferably less than 30%, more preferably less than 20%, even more preferably less than 10% T2N potential compared to a malt composition prepared in the same manner from a wild-type barley, preferably from cv. Power. More preferably, said malt compositions comprise less than 60%, more preferably 50% T2N potential compared to a malt composition prepared in the same manner from the barley null-LOX-1 mutant D112 described in WO 2005/087934. Malting is a process of controlled steeping and germination, followed by drying of the barley grain, preferably kiln drying of the barley grain. Prior to drying, the steeped and germinated barley grains are referred to as "green malt", which may also represent a plant product according to the present invention. This sequence of events is important for the synthesis of numerous enzymes that cause grain modification, processes that principally depolymerize cell walls of the dead endosperm to mobilize the grain nutrients and activate other depolymerases. In the subsequent drying process, flavor and color are produced due to chemical browning reactions. Although the primary use of malt is for beverage production, it can also be utilized in other industrial processes, for example as an enzyme source in the baking industry, or as a flavoring and coloring agent in the food industry, such as malt or malt flour, or indirectly as a malt syrup, etc.

In one aspect, the present invention relates to methods of producing said malt composition. The methods preferably comprise the steps of:

(i) Providing double null-LOX barley kernels;
(ii) Steeping said kernels;
(iii) Germinating the steeped kernels under predetermined conditions;
(iv) Drying said germinated kernels;

thereby producing a malt composition with a total loss of LOX-1 activity and LOX-2 activity. For example, the malt may be produced by any of the methods described by Briggs et al. (1981) and by Hough et al. (1982). However, any other suitable method for producing malt may also be used with the present invention, such as methods for production of specialty malts, including, but not limited to, methods of roasting the malt. Non-limiting examples are described in Examples 6 and 8.

Malt may be further processed, for example by milling. Thus, the plant product according to the invention may be any kind of malt, such as unprocessed malt or milled malt, or flour thereof. Milled malt and flour thereof comprise chemical components of the malt and dead cells that lack the capacity to re-germinate.

In another aspect, the plant products according to the invention comprise or even consist of syrup, such as a barley syrup, or a barley malt syrup. The plant product may also be an extract of barley or malt.

In another aspect, the invention relates to types of plant products, which are wort compositions prepared from malt compositions derived from double null-LOX kernels. Said malts may be prepared from only double null-LOX kernels, or mixtures comprising other kernels as well. The invention also relates to wort compositions prepared using double null-LOX barley, or parts thereof, alone or mixed with other components.

Said wort compositions preferably comprise less than 30%, more preferably less than 20%, even more preferably less than 10% free T2N compared to a wort composition prepared in the same manner from a wild-type barley, preferably from cv. Power. More preferably, said wort compositions comprise less than 60%, more preferably less than 50% free T2N compared to a wort composition prepared in the same manner from barley mutant D112 described in WO 2005/087934. It is furthermore preferred that said wort compositions preferably comprise less than 40%, more preferably less than 30%, even more preferably less than 25% T2N potential compared to a wort composition prepared in the same manner from a wild-type barley, preferably from cv. Power. More preferably, said wort compositions comprise less than 60%, more preferably less than 50% T2N potential compared to a wort composition prepared in the same manner from barley mutant D112 described in WO 2005/087934.

Said wort may be the first, and/or the second, and/or further worts. The wort composition may be sweet wort, boiled wort, or a mixture thereof. The wort composition may also be barley wort. In general, a wort composition contains a high content of amino nitrogen and fermentable carbohydrates, the latter mainly being maltose. In FIG. 3, steps 4 to 6 illustrate the common method for preparation of wort from malt. In general, wort is prepared by combining and incubating malt and water, i.e. in a mashing process. During mashing, the malt/liquid composition may be supplemented with additional carbohydrate-rich adjunct compositions, for example milled barley, maize, or rice adjuncts. Unmalted cereal adjuncts usually contain little or no active enzymes, making it important to supplement with malt or exogenous enzymes to provide enzymes necessary for sugar conversion.

In general, wort production is initiated by the milling of malt such that water may gain access to grain particles in the mashing phase. Said mashing is basically an extension of the malting process, with enzymatic depolymerization of substrates. During mashing, milled malt is incubated with a liquid fraction, such as water. The incubation temperature is in general either kept constant (isothermal mashing), or gradually increased. In either case, soluble substances produced in malting and mashing are liberated into said liquid fraction. A subsequent filtration confers separation of wort and residual solid particles, the latter also denoted "spent grain". Said wort may also be denoted "first wort". After sparging and filtration, a "second wort" may be obtained. Further worts may be prepared by repeating the procedure. Non-limiting examples of suitable procedures for preparation of wort is described by Briggs et al. (supra) and Hough et al. (supra).

It has been described that lipoxygenase activity may be reduced by heat treatment of the enzymes. It has been described that wort may be heat treated to reduced lipxogenase activity and/or that mashing is performed at high temperatures. However, in addition to reducing lipoxygenase activity, heat treatment may have other adverse effects, such as reducing other enzymatic activities. In addition, heat treatment only reduces lipoxygenase activity from the point when the heat treatment is undertaken and thus it does not affect the prior accumulation of lipoxygenase products.

Accordingly, in one embodiment wort according to the invention is prepared using a method wherein the initial mashing temperature does not exceed 70° C., preferably does not exceed 69° C., thus for example the initial mashing temperature may be in the range of 50° C. to 69° C., such as in the range of 55° C. to 69° C., for example in the range of 55° C. to 65° C. It is also preferred that the wort according to the invention has not been subjected to temperatures of 70° C. or higher for more than 25 min, preferably not for more than 20 min, more preferably not for more than 15 min. during mashing. If the mashing temperatures are too high, it will affect the enzymatic activity in the mash and may reduce, or even abolish, desirable enzymatic activities, which will result in an altered quality of the wort.

First, second and further worts may be combined, and thereafter subjected to boiling. The non-boiled wort, either a pure first wort or a combined wort, is also referred to as "sweet wort"; after boiling it may be referred to as "boiled wort". If the wort is to be used in production of beer, hops are frequently added prior to boiling.

The wort composition may also be prepared by incubating double null-LOX barley plants, or parts thereof, such as unmalted double null-LOX kernels, in particular milled, unmalted double null-LOX kernels, or parts thereof, with one or more suitable enzymes, such as enzyme compositions or enzyme mixture compositions, for example Cereflo, Ultraflo, or Ondea Pro (Novozymes). A method for producing a beverage from wort thus prepared may also be referred to as "barley brewing", and a wort composition thereof as "barley wort", or "barley-brewed" wort. The wort composition may also be prepared using a mixture of malt and unmalted barley plants, or parts thereof, or unmalted barley only, optionally adding one or more suitable enzymes during said preparation, in particular amylases, glucanases [preferably (1-4)- and/or (1-3, 1-4)-β-glucanase], and/or xylanase (such as arabinoxylanase), and/or proteases, or enzyme mixtures comprising one or more of the aforementioned enzymes, e.g. adding the enzyme mixture Ondea Pro (Novozymes).

In one specific embodiment of the invention the wort composition according to the present invention is a barley wort, such as boiled barley wort, i.e. wort prepared by incubating unmalted (and preferably milled) double null-LOX kernels with water, preferably by mashing and sparging. Such barley wort is characterized by extremely low levels of T2N and T2N potential. Thus, said barley wort preferably comprises less than 50%, more preferably less than 40%, even more preferably less than 30% free T2N compared to a barley wort composition prepared in the same manner from a wild-type barley, preferably from cv. Power. More preferably, said wort compositions comprise less than 70%, more preferably less than 60% free T2N compared to a wort composition prepared in the same manner from barley mutant D112 described in WO 2005/087934. Moreover, it is preferred that said barley wort comprises at the most most 0.15 ppb free T2N, when said wort is adjusted to a °p in the range of 13 to 16, preferably in the range of 14 to 15, more preferably to 14.5° p. It is furthermore preferred that said barley wort preferably comprises less than 50%, more preferably less than 40%, even more preferably less than 30% T2N potential compared to a barley wort composition prepared in the same manner from a wild-type barley, preferably from cv. Power. It is also preferred that said barley wort preferably comprises less than 50%, more preferably less than 40%, even more preferably less than 30% T2N precursor compared to a barley wort composition prepared in the same manner from a wild-type barley, preferably from cv. Power.

The present invention also relates to plant products, which may be food compositions, feed compositions, and fragrance raw material compositions that comprise double null-LOX barley plants, or parts thereof. Food compositions, for example, may be, but are not limited to, malted and unmalted barley kernels, barley meals, bread, porridge, cereal mixes comprising barley, health products, such as beverages comprising barley, barley syrups, and flaked, milled or extruded barley compositions. Feed compositions, for example, include compositions comprising barley kernels, and/or meals. Fragrance raw material compositions are described herein below.

The invention also relates to mixtures of the compositions of the invention. For example, the invention in one aspect relates to a composition prepared by a mixture of:
  (i) a composition comprising a barley plant, or a part thereof, comprising a first mutation that results in a total loss of function of LOX-1 activity, such as a total loss of functional LOX-1 enzyme, and a second mutation resulting in a total loss of function of LOX-2 activity, such as total loss of functional LOX-2 enzyme; and
  (ii) a malt composition prepared from double null-LOX kernels.

In a preferred aspect, the present invention relates to beverages, more preferred malt beverages, even more preferred fermented beverages, such as fermented malt beverages, preferably alcoholic beverages, such as beer having stable organoleptic qualities, wherein said beverage is prepared using double null-LOX barley, or parts thereof. Hence, in one preferred embodiment of the invention, the beverage is preferably prepared by fermentation of double null-LOX barley, or parts thereof, or extracts thereof, for example by fermentation of wort from double null-LOX malt, alone or in combination with other ingredients.

In other embodiments of the invention, however, the beverage is a non-fermented beverage, for example wort, preferably wort prepared from double null-LOX malt. It is also comprised within the present invention that said beverage may be prepared from unmalted barley plants, or parts thereof.

The beverage may be a non-alcoholic beverage, such as non-alcoholic beer or other kinds of non-alcoholic beverages, such as non-alcoholic malt beverages, such as maltina.

Preferably, however, said beverage is prepared from a malt composition prepared from double null-LOX barley kernels.

More preferably, said beverage is beer. This may be any kind of beer known to the person skilled in the art. In one embodiment, the beer is, for example, a lager beer. The beer is preferably brewed using a malt composition comprising germinated double null-LOX barley, more preferably said beer is brewed using a malt composition prepared exclusively from germinated double null-LOX barley. The malt composition may, however, also comprise other components, for example other germinated or non-germinated cereals, such as wild-type barley, null-LOX-1 barley, wheat and/or rye, or non-germinated raw materials that comprise sugars, or compositions derived from malted or unmalted raw materials, including syrup compositions. However, preferably all barley, such as all malted and/or unmalted barley and/or germinated and/or non-germinated barley used for preparation of said beer is preferably double null-LOX barley.

In a preferred embodiment, the beverage according to the invention is beer that has been produced from wort prepared from kilned malt, preferably by mashing and optionally sparging. Such beer may also be referred to as "malted" herein. However, the beverage according to the invention may also be beer prepared from barley wort. Such beer is also referred to as "barley beer".

In a preferred embodiment, the beverage according to the invention comprises less than 50%, preferably less than 40%, more preferably less than 35%, such as less 30% T2N potential compared to the T2N potential of a beverage prepared in the same manner from wild-type barley, preferably from cv. Power. It is also preferred that the beverage according to the invention comprises less than 70%, preferably less than 60%, such as less than 50% T2N potential compared to a beverage prepared in the same manner from a null-LOX-1 barley mutant, preferably from barley mutant D112 described in WO 2005/087934. It is also preferred that the beverages according to the invention comprise at the most 2 ppb, more preferably at the most 1.5 ppb, such as at the most 1 ppb T2N potential if the ° p in the original extract upon which the beverage is based is adjusted to in the range of 10 to 12° p, more preferably to 11° p.

In a preferred embodiment, the beverage according to the invention comprises less than 50%, preferably less than 40%, more preferably less than 35%, such as less 30% T2N precursor compared to the T2N precursor of a beverage prepared in the same manner from wild-type barley, preferably from cv. Power. It is also preferred that the beverage according to the invention comprises less than 70%, preferably less than 60%, such as less than 50% T2N precursor compared to a beverage prepared in the same manner from barley mutant D112 described in WO 2005/087934. It is also preferred that the beverages according to the invention comprise at the most 2 ppb, more preferably at the most 1.5 ppb, such as at the most 1 ppb T2N precursor if the ° p in the original extract upon which the beverage is based is adjusted to in the range of 10 to 12° p, more preferably to 11° p.

In one specific embodiment of the invention, the beverage is barley beer, which comprises less than 50%, preferably less than 40%, more preferably less than 35% T2N potential compared to the T2N potential of a barley beer prepared in the same manner from wild-type barley, preferably from cv. Power. In this embodiment, it is also preferred that said barley beer comprises less than 50%, preferably less than 40%, more preferably less than 35% T2N precursor compared to the T2N precursors of a barley beer prepared in the same manner from wild-type barley, preferably from cv. Power. In this embodiment, it is also preferred that the barley beer according to the invention comprises at the most 2 ppb, more preferably at the most 1.5 ppb, even more preferably at the most 1.2 ppb T2N potential. In this embodiment, it is furthermore preferred that the barley beer according to the invention comprises at the most 2 ppb, more preferably at the most 1.5 ppb, even more preferably at the most 1.2 ppb T2N precursor if the ° p in the original extract upon which the beverage is based is adjusted to in the range of 10 to 12° p, more preferably to 11° p.

In another specific embodiment of the invention the beverage is beer prepared from malt, wherein said beer comprises less than 50%, preferably less than 40%, more preferably less than 30% T2N potential compared to the T2N potential of a beer prepared in the same manner from wild-type barley, preferably from cv. Power. In this embodiment, it is also preferred that said beer comprises less than 50%, preferably less than 40%, more preferably less than 30% T2N precursor compared to the T2N precursors of a beer prepared in the same manner from wild-type barley, preferably from cv. Power. In this embodiment, it is also preferred that the beer according to the invention comprises at the most 2 ppb, more preferably at the most 1.5 ppb, even more preferably at the most 1 ppb T2N potential. In this embodiment, it is furthermore preferred that the beer according to the invention comprises at the most 2 ppb, more preferably at the most 1.5 ppb, even more preferably at the most 1 ppb T2N precursor if the ° p in the original extract upon which the beverage is based is adjusted to in the range of 10 to 12° p, more preferably to 11° p.

"Organoleptic qualities" means qualities appealing to the human olfactory and taste senses. These are analyzed, for example, by a trained, specialized taste panel. Preferably, said taste panel is trained specifically to recognize aldehyde off-flavors, such as T2N. In general, the taste panel will consist of in the range of 3 to 30 members, for example in the range of 5 to 15 members, preferably in the range of 8 to 12 members. The taste panel may evaluate the presence of various flavors, such as papery, oxidized, aged, and bready off-flavors. In relation to the present invention, it is preferred that papery and/or aged off-flavors are in particular reduced. A method of determining the "organoleptic qualities" of a beverage is described in Example 6 in international patent application WO 2005/087934. Another preferred method of determining "organoleptic qualities" of a beverage is described in Examples 8 and 9 hereinafter. In preferred embodiments, the stable organoleptic qualities are, at least partly, a result of low levels of T2N or T2N potential.

It is preferred that the beverages according to the present invention are characterized by having a less papery taste compared to a similar beverage prepared in the same manner from a barley plant containing LOX-1 and LOX-2 activity after storage for at least 10 months at in the range of 15 to 25° C., such as around 20° C. Preferably, said papery taste is less than 90%, more preferably less than 80%, such as less than 70% as evaluated by a trained taste panel.

It is also preferred that the beverages according to the present invention have reduced papery taste as compared to a similar beverage prepared from wild-type barley after storage at elevated temperatures. When the property "papery taste" is determined by a trained, specialized taste panel—as described above, and scored on a scale from 0 to 5, where 0 is absent and 5 is extreme—then it is preferred that the beverages of the invention have one or more, preferably at least two, such as at least three, for example all of the following scores for papery taste:
(i) A score for papery taste at least 0.5, preferably at least 0.7, more preferably at least 1.0 lower than the score for papery taste of a beverage prepared in the same manner from wild-type barley, preferably from cv. Power after incubation at 37° C. for one week;

(ii) A score for papery taste at least 0.5, preferably at least 0.7, more preferably at least 1.0 lower than the score for papery taste of a beverage prepared in the same manner from wild-type barley, preferably from cv. Power after incubation at 37° C. for two weeks;

(iii) A score for papery taste at least 0.5, preferably at least 0.7, such as at least 1.0 lower than the score for papery taste of a beverage prepared in the same manner from wild-type barley, preferably from cv. Power after incubation at 37° C. for three weeks;

(iv) A score for papery taste at the most 90%, preferably at the most 80%, more preferably at the most 70%, even more preferably at the most 60%, yet more preferably at the most 50% of the score for papery taste of a beverage prepared in the same manner from wild-type barley, preferably from cv. Power after incubation at 37° C. for one week;

(v) A score for papery taste at the most 90%, preferably at the most 80%, more preferably at the most 70%, even more preferably at the most 60% of the score for papery taste of a beverage prepared in the same manner from wild-type barley, preferably from cv. Power after incubation at 37° C. for two weeks;

(vi) A score for papery taste at the most 90%, preferably at the most 80% of the score for papery taste of a beverage prepared in the same manner from wild-type barley, preferably from cv. Power after incubation at 37° C. for three weeks;

A beverage is said to have "stable organoleptic qualities", when said beverage comprises very low levels of free T2N, even after storage. Accordingly, it is an objective of the present invention to provide beverages (such as beer with stable organoleptic qualities), manufactured using a double null-LOX barley plant. Such beverages preferably comprise very low levels of T2N potential—preferably less than 50%, preferably less than 40%, more preferably less than 35%, such as less than 30%, for example less than 20%, such as less than 10% T2N potential compared to a beverage prepared in the same manner from wild-type barley, preferably from cv. Power—after storage for at least 1 week, preferably at least 2 weeks, more preferably at least 3 weeks, even more preferably for at least 4 weeks, such as in the range of 1 to 3 months, for example in the range of 3 to 6 months, such as in the range of 6 to 12 months, for example for more than one year.

Moreover, it is preferred that the beverages according to the invention comprise very low levels of T2N—preferably less than 50%, preferably less than 40%, more preferably less than 35%, even more preferably less than 30%, for example less than 25% free T2N compared to a beverage prepared in the same manner from wild-type barley, preferably from cv. Power—after storage for at least 1 week, preferably at least 2 weeks, more preferably at least 3 weeks, even more preferably for at least 4 weeks at a temperature in the range of 30 to 40° C., preferably at 37° C., such as in the range of 1 to 3 months, for example in the range of 3 to 6 months, such as in the range of 6 to 12 months, for example for more than one year at a temperature in the range of 20-30°.

In particular, it is preferred that the beverages according to the invention comprise very low levels of T2N—preferably less than 50%, preferably less than 40%, more preferably less than 35% free T2N compared to a beverage prepared in the same manner from wild-type barley, preferably from cv. Power—after storage for 2 weeks at 37° C. It is also preferred that the beverages according to the invention comprises less than 50 ppt, even more preferably less than 40 ppt, even more preferably less than 30 ppt free T2N after storage for 2 weeks at 37° C. Preferably said storage is performed in the presence of a level of sulfite not exceeding 10 ppm, preferably a level of sulfite in the range of 1 to 10 ppm, more preferably in the range of 1 to 8 ppm, more preferably in the range of 2 to 6 ppm, yet more preferably in the range of 3 to 5 ppm, such as 4 ppm sulfite.

It is also preferred that the beverages according to the invention comprise less than 80%, preferably less than 75%, such as less than 60% free T2N compared to a beverage prepared in the same manner from null-LOX-1 barley, preferably from barley mutant D112 described in WO 2005/087934—after storage for 2 weeks at 37° C. Preferably said storage is performed in the presence of a level of sulfite not exceeding 10 ppm, preferably a level of sulfite in the range of 1 to 10 ppm, more preferably in the range of 1 to 8 ppm, more preferably in the range of 2 to 6 ppm, yet more preferably in the range of 2 to 4 ppm.

It is also particularly preferred that the beverages (such as beer, for example barley beer) according to the invention comprise very low levels of T2N—preferably less than 50%, preferably less than 40%, more preferably less than 35%, even more preferably less than 30%, yet more preferably less than 25% free T2N compared to a beverage prepared in the same manner from wild-type barley, preferably from cv. Power—after storage for 8 weeks at 37° C. It is furthermore preferred that the beverages (such as beer, for example barley beer) comprises at the most 50 ppt, even more preferably at the most 40 ppt, yet more preferably at the most 30 ppt, even more preferably at the most 20 ppt free T2N after storage for 8 weeks at 37° C. Preferably said storage is performed in the presence of a level of sulfite not exceeding 10 ppm, preferably a level of sulfite in the range of 1 to 10 ppm, more preferably in the range of 1 to 8 ppm, more preferably in the range of 1 to 6 ppm, yet more preferably in the range of 2 to 4 ppm, such as 3 ppm sulfite.

It is also preferred that the beverages according to the invention comprise less than 70%, preferably less than 60%, even more preferably less than 55% free T2N compared to a beverage prepared in the same manner from null-LOX-1 barley, preferably from barley mutant D112 described in WO 2005/087934—after storage for 8 weeks at 37° C. Preferably said storage is performed in the presence of a level of sulfite not exceeding 10 ppm, preferably a level of sulfite in the range of 1 to 10 ppm, more preferably in the range of 1 to 8 ppm, more preferably in the range of 2 to 6 ppm, yet more preferably in the range of 2 to 4 ppm.

Furthermore, it is an objective of the present invention to provide beverages, such as beer manufactured using a double null-LOX barley plant—preferably comprising less than 70%, preferably less than 60%, such as less than 50% T2N and/or T2N potential, more preferably less than 70%, preferably less than 60%, such as less than 50% free T2N—compared to a beverage prepared in the same manner from barley mutant D112 as described in WO 2005/087934, after storage for at least 1 week, preferably at least 2 weeks, more preferably at least 3 weeks, even more preferably for at least 4 weeks at a temperature in the range of 30 to 40° C., preferably at 37° C., such as in the range of 1 to 3 months, for example in the range of 3 to 6 months, such as in the range of 6 to 12 months, for example for more than one year at a temperature in the range 20 to 30° C.

In particular, it is preferred that the beverages (such as beer, for example barley beer) according to the invention comprise very low levels of T2N—preferably less than 70%, preferably less than 60%, more preferably less than 55%, even more preferably less than 52% free T2N—compared to a beverage prepared in the same manner from wild-type barley, preferably from cv. Power, after storage for 8 weeks at 37° C.

Preferably said storage is performed in the presence of a level of sulfite not exceeding 10 ppm, preferably a level of sulfite in the range of 1 to 10 ppm, more preferably in the range of 1 to 8 ppm, more preferably in the range of 1 to 6 ppm, yet more preferably in the range of 2 to 4 ppm, such as 3 ppm sulfite.

Preferably, the beverage according to the invention also comprises in the range of 1 to 10 parts per million (ppm) sulfite, more preferably in the range of 2 to 8 ppm, more preferably in the range of 3 to 7 ppm, yet more preferably in the range of 4 to 6 ppm sulfite. The beverages of the invention preferably comprise at the most 0.07, preferably at the most 0.06, more preferably at the most 0.05, even more preferably at the most 0.04, such as at the most 0.03 parts per billion (ppb) free T2N after storage for at least 1 week, preferably at least 2 weeks, more preferably at least 3 weeks, even more preferably for at least 4 weeks, such as in the range of 1 to 3 months, for example in the range of 3 to 6 months, such as in the range of 6 to 12 months, for example for more than one year after storage at a temperature in the range of 15° C. to 40° C., preferably in the range of 30° C. to 37° C., more preferably at 37° C. In one preferred embodiment of the invention, the beverages according to the invention comprise at the most 0.03 ppb, preferably at the most 0.025 ppb, more preferably at the most 0.02 ppb (parts per billion) free T2N after storage for 4 weeks at 37° C. in the presence of in the range of 4 to 6 ppm sulfite.

The beverages with stable organoleptic qualities according to the invention preferably comprise low levels of T2N potential, preferably less than 40%, more preferably less than 30%, even more preferably less than 25% T2N potential compared to a similar beverage prepared in the same manner from a wild-type barley plant, preferably from cv. Power.

In one embodiment, the invention relates to beverages, such as beer, with low levels of certain trihydroxy octadecenoic acids (also denoted THAs), in particular to beverages with low levels of 9,12,13-THA and 9,10,13-THA. THAs are characterized by a bitter taste (Baur and Grosch, 1977; Baur et al., 1977), and are therefore considered undesirable.

It is thus desirable that the level of 9,12,13-THA and 9,10,13-THA is as low as possible, preferably lower than 1.3 ppm, such as lower than 1 ppm. However, the overall concentration of 9,12,13-THA and 9,10,13-THA in a malt-derived beverage—such as beer—is also dependent on the amount of malt used for preparation of said specific beverage. Thus, in general, a strong beer will comprise more 9,12,13-THA and 9,10,13-THA than a lighter beer, making a higher over-all level of 9,12,13-THA and 9,10,13-THA acceptable in a stronger beer. Accordingly, it is preferred that the beverage according to the invention comprises a lower level of 9,12,13-THA and 9,10,13-THA than a beverage prepared in the same manner from wild-type barley, preferably from cv. Power. In particular, a beverage according to the invention preferably has a level of 9,12,13 THA, which is at the most 50%, preferably at the most 40%, more preferably at the most 30% compared to the level in a beverage prepared in the same manner from a wild-type barley, preferably from cv. Power. It is furthermore preferred that a beverage according to the invention has a level of 9,10,13 THA, which is at the most 70%, preferably at the most 60% compared to the level in a beverage prepared in the same manner from a wild-type barley, preferably from cv. Power. Such beverages may be prepared by using double null-LOX barley.

In one embodiment of the invention, the beverages have improved foam quality. This is in particular relevant when the beverage is a beer. Accordingly, it is an objective of the invention to provide beverages, such as beer, with superior foam quality. Preferably, the beverages of the invention produce at least 10% more, preferably at least 20% more, yet more preferably at least 25% more foam in 60 to 80 min, preferably in 80 min. compared to a beverage prepared in the same manner from wild-type barley, preferably from cv. Power. Said foam production is determined as described in Example 9 herein below.

The invention also relates to methods of producing said beverage. The methods preferably comprise the steps of:
(i) Providing a malt composition comprising germinated double null-LOX kernels;
(ii) Processing said malt composition into a beverage;
thereby obtaining a beverage with more stable organoleptic qualities.

In one preferred embodiment, the beverage is beer. In this case, the processing step preferably comprises preparing wort from said malt composition, for example by any of the methods described hereinabove, and fermenting said wort.

In general terms, alcoholic beverages—such as beer—may be manufactured from malted and/or unmalted barley grains. Malt, in addition to hops and yeast, contributes to flavor and color of the beer. Furthermore, malt functions as a source of fermentable sugar and enzymes. A schematic representation of a general process of beer production is shown in FIG. 3, while detailed descriptions of examples of suitable methods for malting and brewing can be found, for example, in publications by Briggs et al. (1981) and Hough et al. (1982). Numerous, regularly updated methods for analyses of barley, malt and beer products are available, for example, but not limited to, American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention. Non-limiting example are described in Example 8 and Example 9.

The malt composition of the aforementioned beverage—such as beer, malt drinks, or non-fermented wort—may, for example, be obtained by any of the methods described herein above. Wort may be prepared from said malt composition as described hereinabove.

The first step of producing beer from wort preferably involves boiling said wort. During boiling, other ingredients may be added—for example hops that provide the typical bitter and aromatic beer characteristics. Boiling of wort also causes aggregation between polyphenols and denatured proteins, which mainly precipitate during the subsequent phase of wort cooling. After being cooled, the wort is transferred to fermentation tanks containing yeast. Preferably, said yeast is brewer's yeast, *Saccharomyces carlsbergensis*. The wort will be fermented for any suitable time period, in general in the range of 1 to 100 days. During the several-day-long fermentation process, sugar is converted to alcohol and $CO_2$ concomitantly with the development of some flavor substances.

Subsequently, the beer may be further processed, for example chilled. It may also be filtered and/or lagered—a process that develops a pleasant aroma and a less yeasty flavor. Also additives may be added. Furthermore, $CO_2$ may be added. Finally, the beer may be pasteurized and/or filtered, before it is packaged (e.g. bottled or canned).

Despite advances in the area of beer production, it would be beneficial to reduce the levels of T2N and T2N potential in beer. Accordingly, there remains a need for new raw materials, particularly barley and malt that contribute with less off-flavors to the finished beer. It is therefore an objective of the present invention to provide such barley plants and malt.

Various methods are available to determine whether a barley plant, or a plant product, is prepared from a barley plant carrying mutations in the genes for LOX-1 and LOX-2, causing a total loss of functional LOX-1 enzyme and a total loss of functional LOX-2 enzyme. Plant products will, in general, comprise at least some genomic DNA from the plant utilized for its production. Thus, malt will contain large amounts of genomic DNA, but even barley or malt extracts, such as wort, may comprise genomic DNA or fragments thereof from said barley or malt. Also barley-based beverages, such as beer, may comprise genomic DNA or fragments thereof from said plant. By analysis of DNA in a plant product, it may be established whether the plant, from which the plant product is prepared, carries mutations in the LOX-1 and LOX-2 genes, causing a total loss of functional LOX-1 enzyme and a total loss of functional LOX-2 enzyme. Said mutations could, for example, be any of the mutations in the LOX-1 and LOX-2 genes described hereinabove in the section "Loss of function of LOX activity". The genomic DNA may be analyzed by any useful method, such as sequencing or by amplification-based methods, including PCR-based methods. If particular mutations in the LOX-1 gene and/or the LOX-2 gene are assumed, then polymorphism analysis may be employed, for example SNP analysis. Such analysis may be performed as described hereinafter in Example 10. The skilled person will be able to adapt the specific SNP analysis described in these examples for use with other mutations or other starting material.

If the above-mentioned plant products only are prepared from barley plants carrying mutations in the genes for LOX-1 and LOX-2, causing a total loss of functional LOX-1 enzyme and a total loss of functional LOX-2 enzyme, then presence vs. absence of barley LOX-1 mRNA and LOX-2 mRNA and/or LOX-1 protein and LOX-2 protein may also be indicative of whether said plant product is prepared from a double null-LOX barley plant. Examination of the plant product may also be accomplished by western blot analysis, or other protein analysis, or by RT-PCR, or by Northern blot analysis, or by other mRNA analyses. Such analyses are particularly useful when the plant product is malt.

Chemical Mutagenesis

In order to generate double null-LOX barley plants according to the present invention—i.e. plants comprising a first mutation that results in a total loss of functional LOX-1 enzyme and a second mutation resulting in a total loss of functional LOX-2 enzyme—a very large number of barley mutants are prepared by any suitable mutagenesis method, for example by the use of chemical mutagenesis of barley kernels. This method is known to introduce mutations at random. Mutagenesis of barley may be performed using any mutagenizing chemical. However, it is preferably performed by treating kernels with $NaN_3$, letting the surviving kernels germinate, followed by analysis of off-spring plants. The plant generation growing from the mutagenized kernels, referred to as M0, contains heterozygote chimeras for any given mutation. Progeny plants collected after self-pollination are referred to as the M1 generation, in which a given mutation segregates into the corresponding heterozygotes and homozygotes (cf. FIG. 1).

Treating kernels with $NaN_3$ is not equivalent to treating a single cell, because the kernels after the treatment will contain some non-mutant cells and a variety of cells having DNA mutations. Since mutations in cell lineages that do not lead to the germ line will be lost, the goal is to target the mutagen to the few cells that develop into reproductive tissues which contribute to development of the M1 generation.

To assess the overall mutation efficiency, albino chimeras and albino plants may be counted in the generations M0 and M1. Scoring mutant number as a function of surviving plants gives an estimate for the mutation efficiency, while scoring mutant number as a function of treated seeds measures the combination of both mutation efficiency and kernel kill.

It is notable that cells have quality assurance mechanisms at virtually every step of gene expression, possibly to moderate the effects of damaging mutations. One well-studied example in eukaryotes is nonsense-mediated mRNA decay, denoted NMD, which prevents the synthesis of potentially deleterious, prematurely truncated proteins (Maquat and Carmichael, 2001; Wu et al., 2007). In NMD, a termination codon is identified as premature by its position relative to downstream destabilizing elements. Mutations that generate premature termination (nonsense) codons (PTCs) sometimes increase the levels of alternatively spliced transcripts that skip the offending mutations, thereby potentially saving protein function (Mendell and Dietz, 2001).

Plant Breeding

In one embodiment of the invention, the objective is to provide agronomical useful barley plants comprising the double null-LOX trait. Crop development is often a lengthy and difficult process that begins with the introduction of the new trait. From the perspective of a plant breeder, however, this step almost always results in a plant that has a less desirable overall profile of agronomic traits than do current commercial varieties.

In addition to the double null-LOX trait, there are additional factors which also may be considered in the art of generating a commercial malting barley variety, for example kernel yield and size, and other parameters that relate to malting performance or brewing performance. Since many— if not all—relevant traits have been shown to be under genetic control, the present invention also provides modern, homozygous, high-yielding malting cultivars, which may be prepared from crosses with the double null-LOX barley plants that are disclosed in the present publication. Kernels of such barley plants provide a new raw material having low capacity for generation of T2N potential, i.e. malt produced from such kernels preferably have less than 50% T2N potential compared to malt produced in the same manner from barley null-LOX-1 mutant D112 described in WO 2005/087934. The skilled barley breeder will be able to select and develop barley plants, which—following crossings with double null-LOX barley—will result in superior cultivars. Alternatively, the barley breeder may utilize plants of the present invention for further mutagenesis to generate new cultivars derived from double null-LOX barley.

One method to ensure that the double null-LOX trait is maintained in progeny lines concerns SNP analysis of the LOX-1 gene and of the LOX-2 gene. Preferably, LOX-1 and LOX-2 activities are also determined.

The barley plants according to the present invention may be introduced into any suitable breeding scheme.

Another objective of the present invention is to provide agronomical elite barley plants comprising the double null-LOX trait. Accordingly, this invention also is directed to methods for producing a new double null-LOX barley plant by crossing a first parental barley plant with a second parental barley plant, wherein the first or second plant is a double null-LOX barley. Additionally, both first and second parental barley plants can come from a double null-LOX barley variety. Thus, any such methods using the double null-LOX barley variety are part of this invention: selfing, backcrossing, crossing to populations, and the like. All plants produced using a double null-LOX barley variety as a parent are within the scope of this invention, including those plants developed from varieties derived from a double null-LOX barley variety.

The double null-LOX barley can also be used for genetic transformation in such cases where exogenous DNA is introduced and expressed in the double null-LOX plant or plant tissue.

Backcrossing methods can be used with the present invention to introduce into another cultivar the double null-LOX trait of a mutated barley plant, for example cv. Scarlett or cv. Jersey, both of which are contemporary, high-yielding malting barley cultivars. In a standard backcross protocol, the original variety of interest, i.e. the recurrent parental plant, is crossed to a second variety (non-recurrent parental plant), carrying the mutant LOX genes of interest to be transferred. The resulting double null-LOX progeny plants from this cross are subsequently crossed to the recurrent parental plant, with the process being repeated until a barley plant is obtained wherein essentially all of the characteristics specified by the recurrent parent are recovered in the generated plant—in addition to the double null-LOX trait of the nonrecurrent parental plant. Eventually, the last-generated, backcrossed plant is selfed to yield a pure double null-LOX breeding progeny plant.

A way to accelerate the process of plant breeding comprises the initial multiplication of generated mutants by application of tissue culture and regeneration techniques. Thus, another aspect of the present invention is to provide cells, which upon growth and differentiation produce barley plants having the double null-LOX trait. For example, breeding may involve traditional crossings, preparing fertile anther-derived plants or using microspore culture.

LOX Pathway Products

In various embodiments, the present invention relates to barley plants, and products thereof, comprising low levels of T2N potential. LOX enzymes catalyze dioxygenation of polyunsaturated fatty acids with a cis-1,cis-4 pentadiene system. In barley, the $C_{18}$ polyunsaturated fatty acids linoleic acid ($18:2^{\Delta 9,12}$) and α-linolenic acid ($18:3^{\Delta 9,12,15}$) are major LOX substrates. The lipoxygenase pathway of fatty acid metabolism is initiated by the addition of molecular oxygen at the C-9 position (mostly catalyzed by LOX-1) or C-13 position (mostly catalyzed by LOX-2) of the acyl chain, yielding the corresponding 9- and 13-HPODEs [9- and 13-hydroperoxy octadecatrienoic acids (HPOTEs) are products when the substrate is α-linolenic acid, but HPOTEs do not function as precursors for T2N]. In the hydroperoxide lyase branch of the LOX pathway, both 9- and 13-HPODEs may be cleaved to short-chain oxoacids and aldehydes (cf. FIG. 2). In particular, 9-HPODE may be cleaved to form cis-nonenal that is converted to T2N, whereas 13-HPODE is the precursor of 2-E-hexenal. Thus, 13-HPODE, the major product of LOX-2-catalyzed dioxygenation of linoleic acid was not anticipated to be an upstream component in the pathway leading to formation of the stale flavor T2N.

It is recognized that the present invention encompasses influencing production of downstream metabolites of LOX-1 and LOX-2 catalysis, which are not produced as a direct product of a LOX-1 or LOX-2-catalyzed reaction, but as a result of a subsequent series of reactions. These include spontaneous, factor-induced, or enzyme-catalyzed isomerizations and conversions. Thus, the production of these downstream metabolites could be influenced by modulating the expression of other components of the pathway, for example hydroperoxide lyase (HPL).

T2N Potential

An important objective of the present invention is to reduce or eliminate the T2N potential. Thus, it is an objective of the present invention to reduce the formation of T2N precursors and aldehyde adducts. Although several chemical reactions related to beer staling remain elusive, generation of free T2N from T2N potential is recognized as a major cause of the development of stale flavor in beer products (Kuroda et al., supra). Accordingly, it is an objective of the present invention to provide beverages with low level of T2N potential as well as beverages with low level of T2N precursors.

Most of the T2N potential is transferred from wort to the finished beer, in which free T2N may be liberated (Liegeois et al., 2002), with the conditions of acidity and temperature being important factors in this process. With reference to the present invention, T2N potential is defined as described hereinabove in the definitions. Other methods for determining the level of T2N potential are also available. In order to avoid confusion, the meaning of "T2N potential" in the present context is as described herein above in the definitions. The chemical substances which have the capacity to release T2N or be converted into T2N are denoted "T2N precursors" herein, and T2N precursors determined or measured by alternative methods other than the method for determining T2N potential are referred to as "T2N precursors". T2N precursors may in particular be determined by first treating a sample such that essentially all (preferably all) of its chemical substances, which have the capacity to release T2N or be converted into T2N actually do release T2N and/or convert to T2N, respectively. Thereafter, the level of T2N is determined.

Barley kernels of the instant invention comprise no LOX-1 and LOX-2 activities. Interestingly, such barley kernels contain very little T2N potential.

Beers produced using double null-LOX barley kernels will therefore not only possess a very low level of T2N, but also a very low level of T2N potential. Within the scope of the present invention are double null-LOX barley kernels, which yield beer products that contain very low levels of T2N potential, preferably less than 40%, more preferably less than 30%, even more preferably less than 25% of the level of T2N potential of a similar beer product produced in the same manner from wild-type barley (preferably cv. Power). Thus, said beer product preferably comprises less than 60%, more preferably less than 50% of the T2N potential of a similar beer product produced in the same manner from barley mutant D112 described on WO 2005/087934.

Also, it is preferred that plant products derived from double null-LOX barley kernels possess a very low level of T2N precursors. Within the scope of the present invention are plant products prepared from double null-LOX barley kernels, said plant products containing less than 40%, more preferably less than 30%, even more preferably less than 25% of the level of T2N precursors of a similar plant product produced in the same manner from wild-type barley (preferably cv. Power). Thus, said plant product preferably comprises less than 60%, more preferably less than 50% of the T2N precursors of a similar plant product produced in the same manner from barley mutant D112 described on WO 2005/087934.

It is notable that measured T2N values often are higher in samples of, and in products from, a micro-malted raw material than that from a raw material produced in larger scale, for example from a 30-kg-large pilot-malted sample. However, the relative, experimental values of T2N between large- and small-scale experiments are in general similar.

Similarly, it is notable that measured T2N potentials (and T2N precursors) often are higher in samples of, and in products from, a micro-malted raw material than that from a a raw material produced in larger scale, for example from a 30-kg-large pilot-malted sample. However, the relative, experimental values of T2N potentials between large- and small-scale experiments are in general similar.

EXAMPLES

The examples herein illustrate preferred embodiments of the invention and should not be considered as limiting for the invention.

Unless otherwise indicated, basic molecular biological techniques were performed for manipulating nucleic acids and bacteria as described in Sambrook and Russel (2001).

Example 1

Screening for Low LOX-2 Activity in Mutated, Mature Embryos of a Mutated Null-LOX-1 Population, Generation M3

LOX-1 and LOX-2 are both synthesized in the maturing barley embryo (with LOX-1 being the predominant enzyme), and also in the germinating embryo (with equal levels of both enzymes). For determination of LOX activities in thousands of samples, assays utilizing extracts of barley embryos would be most convenient. And in assays for LOX-2 levels, it would be highly advantageous to screen kernels of mutagenized null-LOX-1 barley, cf. WO 2005/087934.

Kernels were collected from barley plants of null-LOX-1 mutant D112 (described in WO 2005/087934 and deposited with ATCC under the number PTA-5487), and incubated with the mutagen $NaN_3$ to induce point mutations in the barley genomic DNA. The experimental set-ups followed the recommendations provided by Kleinhofs et al. (supra).

Next, mutated grains of generation M1 were propagated in field plots through two subsequent generations, eventually yielding a high proportion of homozygous plants of generation M3 for screening purposes (cf. FIG. 1 for a procedure overview). Mutated grains of generation M3 were expected to contain gene mutations at a frequency of 0.9-2.3 per 10,000 grains (Kleinhofs et al., supra).

LOX-2 activity in mature embryos of the null-LOX-1 mutant was found to be low, as measured by the conventional LOX-1 assay. Here, the stock solutions of the reaction mixture are combined simultaneously with the extract (as described in WO 2005/087934). In the application is detailed a method that improves assay sensitivity, wherein both the enzyme extraction conditions as well as the mixing of the reaction mixture stock solutions were altered.

For LOX extraction, the present inventors found interestingly that using a 100-mM lactic acid buffer, pH 4.5, conferred a significantly reduced background level of HPODE-consuming activity, permitting accumulation of HPODEs in the assay buffer. Additionally, the inventors found that the assay could be further improved by allowing a minor fraction of the formed HPODEs to activate LOX-2 through $Fe^{++} \rightarrow Fe^{+++}$ oxidation of its bound iron atoms prior to addition of the remaining assay reactants, eventually forming a blue indamine dye.

In short, LOX-2 enzyme was extracted from isolated, mature embryos using 200 μl extraction buffer (100 mM lactic acid, pH 4.5). Extraction was performed in 96-well plates in which each 1.2-ml well contained a circular 5-mm glass bead. The plates were incubated on ice for 10 min before transfer to a MM 300 laboratory mill (Retsch), electronically adjusted to shake at a frequency of 27 sec$^{-1}$ for 35 sec. Subsequently, the plate was centrifuged at 4,000 rpm in an Allegra 6R Centrifuge (Beckman-Coulter) for 10 min at 4° C. to precipitate insoluble material, and thereafter kept on ice for max. 2 h before further processing. The 96-well plate was transferred to a Biomek 2000 Laboratory Automation Workstation (Beckman-Coulter) for further pipetting. Initially, 96×40 μl embryo extracts were transferred to a standard 96-well microtitre plate (Nunc), followed by addition of 90 μl of Reagent A [12.5 mM 3-(dimethylamino)benzoic acid, 0.625 mM linoleic acid], which was made by first mixing 155 μl of linoleic acid, corresponding to 134 mg free acid (Sigma, L-1376) and 257 μl Tween-20; then $H_2O$ was added to a volume of 5 ml, followed by addition of 600 μl of 1 M NaOH. The cleared solution was adjusted to 20 ml with $H_2O$. The mixtures were incubated for 10 min before adding 90 μl Reagent B (0.25 mM 3-methyl-2-benzothiazolinehydrazone, 0.125 mg/ml hemoglobin). After further incubation for 5 min, $A_{595}$ was measured in each of the 96 wells of the plate using a Fluorostar Galaxy spectrophotometer (BMG Labtechnologies), with the color formation reflecting the presence of HPODEs generated by LOX-2-catalyzed dioxygenation (activities are accordingly given in $A_{595}$ units).

Using the above-described procedure, a total of 21,000 barley mutant lines were assayed for LOX-2 activity, and 1,550 lines thereof selected based on low LOX-2 activity. These lines were further propagated in the field, with the LOX-2 activity thereafter measured in the mature grains. However, none of the lines were found to transmit the low LOX-2 trait to the next generation.

Example 2

Screening for Low LOX-2 Activity in Germinating Barley Embryos

Improved screening material. Kernels collected from barley plants of null-LOX-1 line Ca211901—generated by the crosses (null-LOX-1 mutant D112×Jersey)×Sebastian— were incubated with the mutagen $NaN_3$ according to the details provided by Kleinhofs et al. (supra). This procedure was chosen since it is known to induce point mutations in the genomic DNA of barley, eventually conferring amino acid residue substitutions or truncations in proteins encoded by the mutagenized DNA. In the mutagenesis experiments of the instant publication, it was chosen to propagate mutated grains of generation M1 in field plots through two subsequent generations, eventually yielding a high proportion of homozygous plants for screening purposes (cf. FIG. 1). While grains of generation M2 were not screened, primarily because these were expected to contain a relatively high proportion of heterozygous point mutations, mutant grains of generation M3 were used as screening material, expecting 0.9-2.3 mutations per 10,000 grains (Kleinhofs et al., supra).

Surprisingly, the instant inventors found that analysis of germinating embryos provided much-improved assay results as compared to analysis of extracts of mature embryos (as described above in Example 1). A high-throughput screening procedure was therefore established to measure LOX-2 activity in the germinating embryo, including its scutellum tissue.

Two embryos were isolated from mature grains of 35,125 barley ears (20,977 lines of generation M4 of null-LOX-1 mutant D112, and 14,148 lines of generation M3 of null-LOX-1 line Ca211901 lines), and transferred to 96-well storage plates (ABgene). Embryo germination was initiated following addition of 20 μl water to each well, which was covered with a wet Kimnett tissue and a plastic lid. The plates were incubated in plastic bags at 20° C. for 48 h. After incubation, LOX-2 enzyme was extracted; to each well was first added a 5-mm glass bead and 200 μl of extraction buffer (100 mM lactic acid solution, pH 4.5), followed by milling for 35 sec at a frequency of 27 sec$^{-1}$ in an MM 300 laboratory mill (Retsch). Subsequently, the plate was centrifuged at 4,000 rpm for 10 min at 4° C. in an Allegra 6R centrifuge (Beckman-Coulter), to precipitate insoluble material. LOX-2 activity was determined basically as described for analysis of LOX-2 activity of mature embryo extracts (Example 1), only differing in the usage of only 30 μl extract per assay instead of 40 μl.

Identification of potential mutants. As described above, two grains each of the above-mentioned 35,125 barley lines were analyzed for LOX-2 activity, with the aim to identify grains highly reduced in said activity when compared with null-LOX-1 and wild-type grains. A total of 7 potential raw mutants were identified in the M3 generation of line Ca211901. These were further propagated in the greenhouse, harvested, and then re-screened for the trait related to very low LOX activity. Eventually, only one mutant of line Ca211901, denoted mutant A689 (and herein also denoted double null-LOX mutant A689), was shown to exhibit essentially no LOX-2 activity. Detailed measurements of total LOX activity were performed with extracts of germinated embryos in which the LOX activity was conferred almost exclusively by LOX-2 (Schmitt and van Mechelen, 1997). For germinated embryos of M3 grains of mutant A689, the total LOX activity—as determined by the colorimetric LOX assay (Example 1; Table 1)—was 0.163±5.5% $A_{595}$ U/germinated embryo, while that for the null-LOX-1 mother variety Ca211901 was 1.224±3.8% $A_{595}$ U/germinated embryo (the corresponding value for null-LOX-1 raw mutant D112 was 1.215±6.0% $A_{595}$ U/germinated embryo.

Example 3

Barley Mutant A689

Analyses were conducted to establish whether null-LOX-2 plants of generations M4 and M5 were homozygous for the corresponding mutant phenotype. This type of analysis would help to determine whether the mutation was genetically recessive or dominant. Additionally, if plants of generation M3 were heterozygous for a dominant mutation, then individuals of subsequent generations would segregate for that phenotype.

Figure 4:
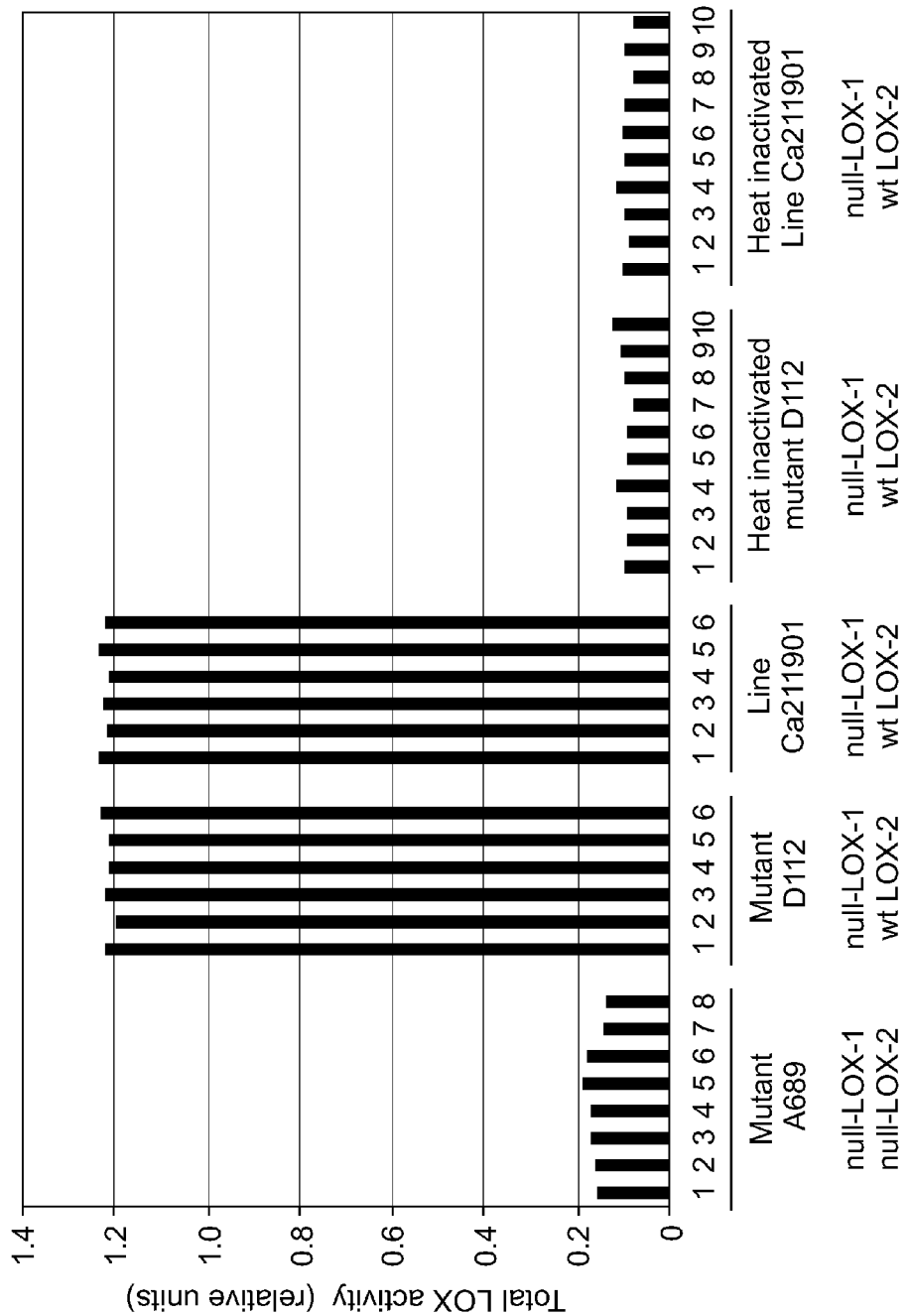
FIG. 4 shows the results of comparisons of total LOX activities in germinated kernels of generation M3 (A), generation M4 (B), and generation M5 (C). Said activities were measured in extracts of embryos that were isolated from germinated kernels of double null-LOX mutant A689, null-LOX-1 mutant D112 and null-LOX-1 breeding line Ca211901. Heat-inactivated extract aliquots of the same samples served as experimental controls [in C: null-LOX-1 raw mutant D112 (*), null-LOX-1 breeding line Ca211901 (**)]. Shown are also the LOX-1 and LOX-2 genotypes of the plant samples analyzed (wt: wild-type).
Figure 4:
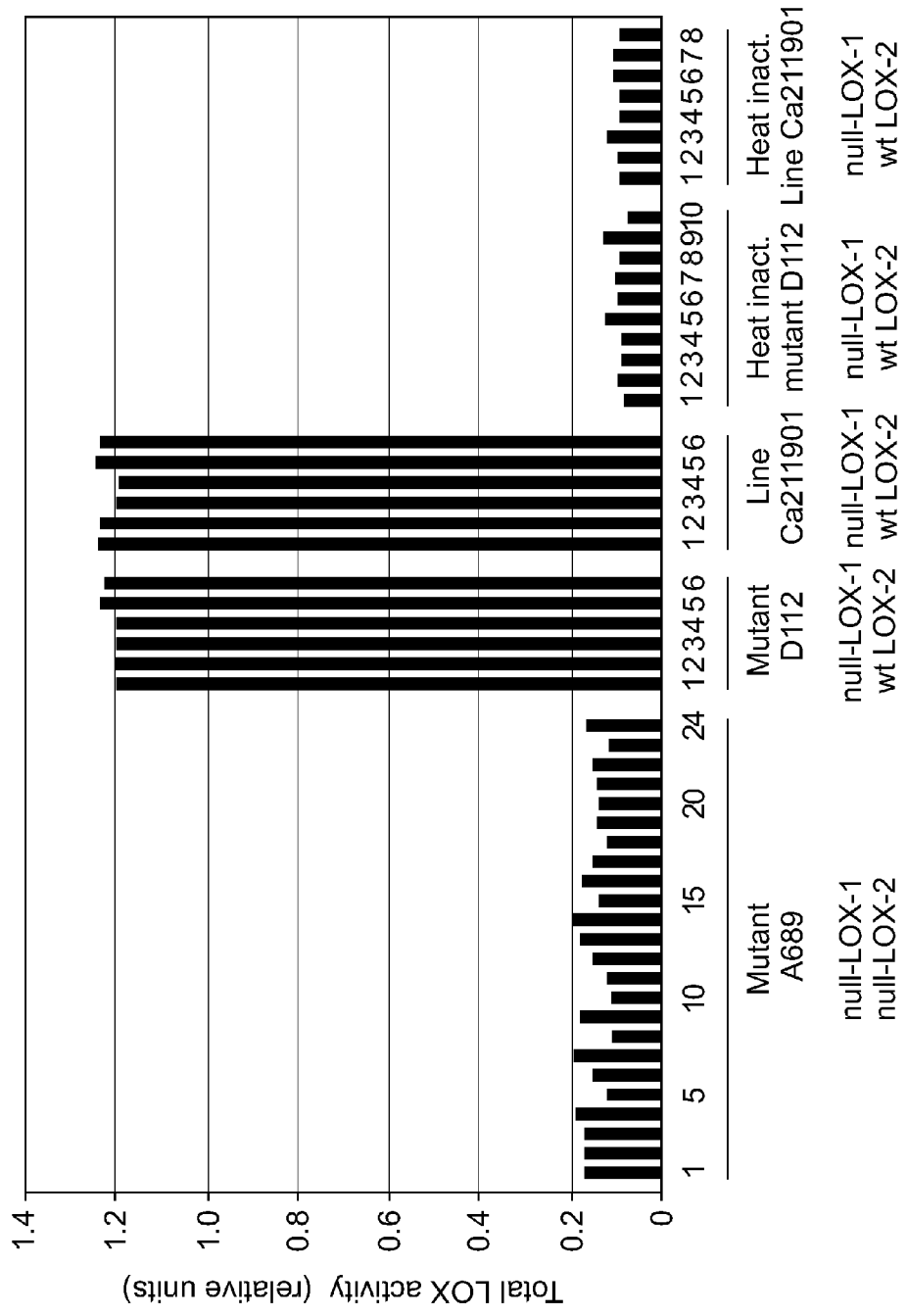
Figure 4:
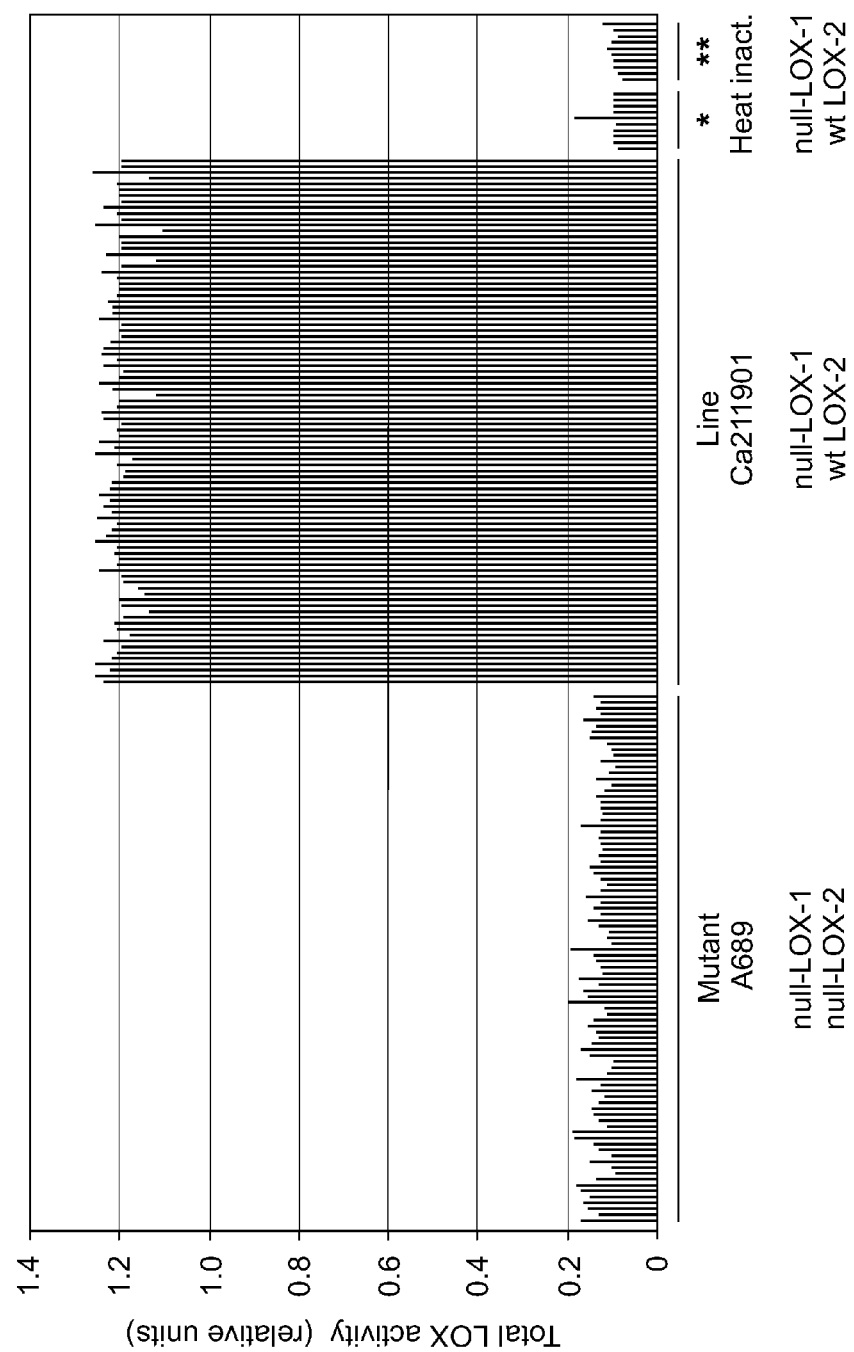

Total LOX activity was measured in barley embryos of generations M3, M4, and M5 of mutant A689, and activities were not only compared with those of embryos of the mother line Ca211901, but also with null-LOX-1 mutant D112. Determination of LOX activity was as described in Example 1 of the instant publication. In all of the experiments, control samples included standard extracts from germinating embryos of the mother line, as well as heat inactivated, standard extracts from embryos of null-LOX-1 mutant line Ca211901 and mutant D112. For embryos of generation M4 grains of mutant A689, the average total LOX activity was 0.151±2.6% $A_{595}$ U (n=24), and that for germinating embryos of generation M5 of mutant A689 was 0.16±2.3% $A_{595}$ U (n=90). For comparison, germinating embryos of null-LOX-1 line Ca211901 and mutant D112 yielded 1.210±3.0% $A_{595}$ U (n=90; generation M4) and 1.199±4.6% $A_{595}$ U (n=90; generation M5), respectively. The results are summarized in Table 1, and in FIG. 4A-C. In summary, the experimental data confirmed that grains of generations M4 and M5 of mutant D112 were homozygous for the genetic trait specifying a very low, total LOX activity, reflecting a double null-LOX phenotype.

TABLE 1

Total LOX activity (average) in extracts prepared form germinated barley embryos of raw mutants (generation M3), and progenies (generations M4 and M5).

| Extracts | Total LOX activity $A_{595}$ units | Lines assayed No. | Standard deviation % |
|---|---|---|---|
| Generation M3 | | | |
| Mutant A689 | 0.163 | 8 | 5.5 |
| Ca211901 | 1.224 | 6 | 3.8 |
| D112 | 1.215 | 6 | 6.0 |
| Ca211901 (heat-inactivated) | 0.099 | 10 | 1.3 |
| D112 (heat-inactivated) | 0.096 | 10 | 1.1 |
| Generation M4 (progeny) | | | |
| Mutant A689 | 0.151 | 24 | 2.6 |
| Ca211901 | 1.223 | 6 | 2.3 |
| D112 | 1.209 | 6 | 5.6 |
| Ca211901 (heat-inactivated) | 0.096 | 10 | 1.7 |
| D112 (heat-inactivated) | 0.101 | 10 | 1.0 |
| Generation M5 (progeny) | | | |
| Mutant A689 | 0.160 | 90 | 2.3 |
| Ca211901 | 1.210 | 90 | 3.0 |
| D112 | 1.199 | 90 | 4.6 |
| Ca211901 (heat-inactivated) | 0.103 | 10 | 2.0 |
| D112 (heat-inactivated) | 0.097 | 10 | 1.2 |

Example 4

HPLC-Based Analysis of HPODEs in Germinated and Micro-Malted Barley

Analysis for barley HPODEs was carried out essentially as described in International Patent Application WO 2005/087934, except utilizing germinating instead of mature embryos. Grains of generation M4 were germinated for 48 h as described in Example 2. Grains of generation M5 were subjected to a micro-malting procedure performed essentially as described in Example 6 hereinafter, but the specific HPODE levels were determined after 72 h of germination, and the kilning procedure was omitted. Levels of 9- and 13-HPODEs were determined by letting crude protein extracts from germinating embryos of generations M4 and M5 of mutant A689 and control samples incubate with the substrate linoleic acid. Reaction products were analyzed by HPLC.

The germinated embryos were dissected from the barley grains using a scalpel to cut between the scutellum and the endosperm. Each 4-embryo-large sample was then placed between two pieces of weighing paper, and hammered gently to produce a homogenous flour. This was transferred to a 1.5-ml microcentrifuge tube; 600 μl of a 200-mM lactic acid buffer, pH 4.5, was added, and the tube was placed on ice for 10 min before further homogenization using a plastic pestle (Kontes). Subsequently, 600 μl $H_2O$ was added to each tube, and the samples were centrifuged for 2 min at 20.000×g. A 100-μl aliquot of the resulting supernatant was transferred to a 15-ml centrifuge tube (Cellstar; cat. no. 188271), to prepare for analysis of the reaction products following LOX action. 2 ml of a 100-mM Na-phosphate buffer, pH 6.5, containing 260 μM linoleic acid [this substrate was prepared by mixing 10 ml of a 100-mM Na-phosphate buffer, pH 6.5, with 100 μl of a 24-mM linoleic acid stock solution. The latter was made by first mixing 155 μl of linoleic acid (corresponding to 134 mg free acid; L-1376, Sigma) and 257 μl Tween-20, then adding $H_2O$ to a volume of 5 ml, followed by addition of 600 μl 1 M NaOH, and when the solution turned clear, adjusting the volume to 20 ml with $H_2O$. After a 15-min incubation at ~30 rpm on a blood tube rotator, 2 ml ethyl acetate was added, and the sample content mixed by vigorous shaking for 5 sec in order to extract 9- and 13-HPODEs. The sample was then centrifuged for 10 min at 800×g, and 1 ml ethyl acetate was transferred to a 1.5-ml microcentrifuge tube, in which ethyl acetate was evaporated under a stream of nitrogen gas. Subsequently, the HPODEs were resuspended in 300 µl methanol, and filtered through a 0.45-µm membrane (Millex-HN filter, Millipore). Analysis of the HPODE content was performed by HPLC. A total of 15 µl from each sample was injected into a HPLC apparatus (HP 1100 Series, Hewlett Packard), equipped with a 4.6×250 mm Symmetry C18 column (Waters). The mobile phase used was a 16:12:12:10:0.5 (v:v:v:v:v) mixture of water:methanol:acetonitrile:tetrahydrofuran:trifluoroacetic acid. The flow of the mobile phase was 1 ml $min^{-1}$, and the pressure measured in front of the column was 140 bars. The separation was performed at 30° C. Detection of linoleic acid hydroperoxides with conjugated double bonds was performed at 234 nm.

Figure 5:
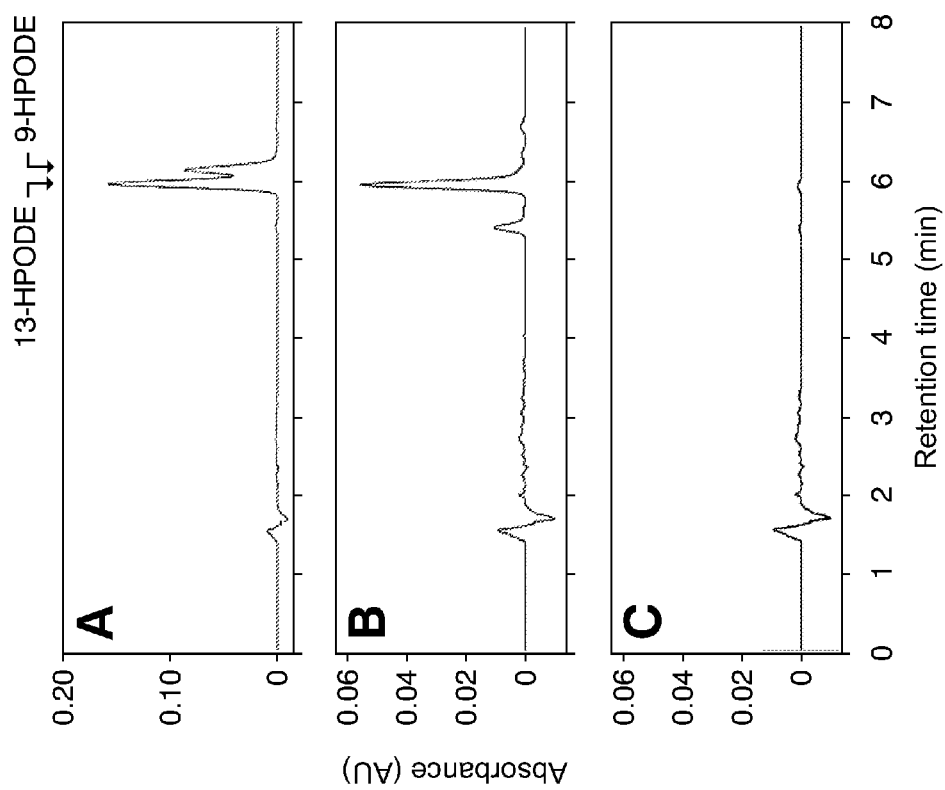
FIG. 5 shows the chromatograms of HPLC analyses used to assay for the formation of 9- and 13-HPODEs in 48-h germinated barley embryos. The HPODEs were detected by measuring the absorbance at 234 nm, with the results given in relative absorbance units (AU). Peaks of the elution profiles that correspond to 9- and 13-HPODEs are indicated by arrows. (A) Chromatogram of 9- and 13-HPODE standards. (B) Chromatogram of HPODEs formed in extracts prepared from germinated embryos of null-LOX-1 mutant D112. (C) Chromatogram of HPODEs formed in extracts prepared from germinated embryos of double null-LOX mutant A689, generation M4.

In FIG. 5 is shown a comparison of HPODE profiles obtained. A chromatogram of a standard sample comprising a mixture of 9- and 13-HPODEs is shown in FIG. 5A. Comparisons of the chromatogram of an extract prepared from 48-h germinated grains of generation M4 of null-LOX mutant D112 (FIG. 5B), with that of double null-LOX mutant A689 (FIG. 5C, revealed pronounced 13-HPODE formation by LOXs extracted from germinated embryos of null-LOX-1 mutant D112, whereas only no or extremely little of 9- and 13-HPODEs were observed in extracts of double null-LOX mutant A689.

Figure 6:
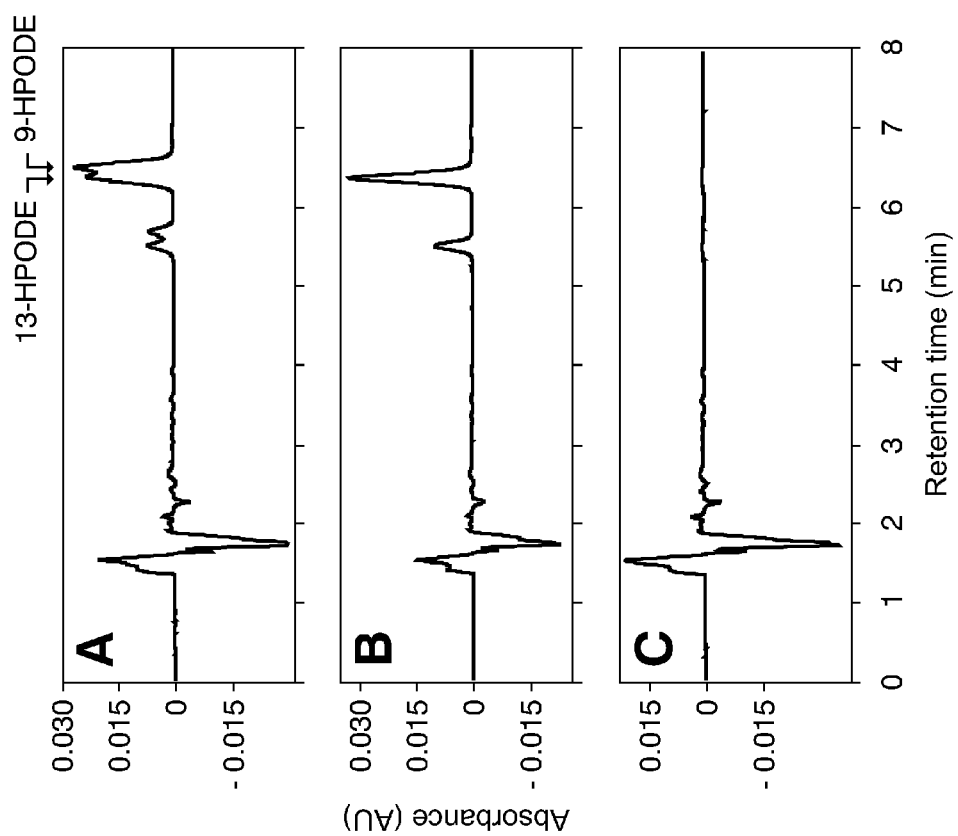
FIG. 6 shows the chromatograms of HPLC analyses used to assay for the formation of 9- and 13-HPODEs in embryos of 72-h micro-malted kernels. HPODE were detected by measuring the absorbance at 234 nm, with the results given in relative absorbance units (AU). Peaks of the elution profiles that correspond to 9- and 13-HPODEs are indicated by arrows. (A) Chromatogram of 9- and 13-HPODEs formed in wild-type cv. Barke. (B) Chromatogram of HPODEs formed in extracts of embryos of null-LOX-1 mutant D112. (C) Chromatogram of HPODEs formed in extracts of double null-LOX mutant A689, generation M5.

Similar characteristics were observed when analyzing 72-h micro-malted embryos of wild-type cv. Barke (FIG. 6A), null-LOX-1 mutant D112 (FIG. 6B), and double null-LOX mutant A689 (FIG. 6C). Again, significant levels of both 9- and 13-HPODEs were formed in extracts of mature embryos of the wild-type cv. Barke (FIG. 6A). Extracts of null-LOX-1 mutant D112 embryos formed very low amounts of 9-HPODE, but high amounts of 13-HPODE (FIG. 6B), thus verifying the lack of LOX-1 activity. And again, embryo extracts of double null-LOX mutant A689 formed no significant levels of 9- and 13-HPODEs (FIG. 6C), confirming the total absence of both LOX-1 and LOX-2 activities.

Example 5

Properties of Barley Double Null-LOX Mutant A689, its Null-LOX-1 Mother Variety Ca211901, and Null-LOX-1 Mutant D112

Plant propagation in the greenhouse. Generation M4 and M5 grains of double null-LOX mutant A689 and its mother line Ca211901 were germinated in the greenhouse, and grown in daily cycles under 20 h of light at 12° C. and 65% relative humidity. The growth characteristics of line Ca211901 and double null-LOX mutant A689 plants were similar with respect to plant height, number of tillers per plant, the onset of flowering, and the number of grains per spike—emphasizing that grain development and growth physiology of mutant A689 is wild-type-like.

Agronomic performance of mutant A689 under field conditions. Plants of double null-LOX mutant A689 and null-LOX-1 mutant D112, as well as plants of line Ca211901, were compared in standard field trials—aiming to identify possible differences with respect to plant height, heading date, disease resistance, lodging, ear breakage, maturation time, and yield (cf. Table 2). Accordingly, equal amounts of the aforementioned kernels were sown in 7.88-$m^2$ plots at one location, each comprising two replications. Agronomic properties, again with emphasis on the aforementioned properties, were carefully observed throughout the entire growth season. No differences with respect to agronomic traits were observed for any of the tested plants.

TABLE 2

Comparison of agronomic performance.

| Property | Mutant A689 | Mother line Ca211901 | Mutant D112 |
|---|---|---|---|
| LOX genotype | null-LOX-1, null-LOX-2 | null LOX-1, wt LOX-2 | null-LOX-1, wt LOX-2 |
| Date of sowing 2007 | 29 March | 29 March | 29 March |
| Length at maturity (cm) | 68 | 69 | 74 |
| Heading date 2007 | 14 June | 14 June | 12 June |
| Powdery mildew* | 0 | 0 | 0 |
| Spot blotch* | 3 | 3 | 2 |
| Net blotch* | 1 | 1 | 1 |
| *Ramularia** | 3 | 3 | 2 |
| Rust* | 1 | 1 | 2 |
| Lodging* | 2 | 2 | 4 |
| Date of maturity 2007 | 1 August | 1 August | 1 August |
| Relative yield 2007** | 107 | 108 | 100 |
| Relative yield 2008** | 104 | 103 | 99 |

*On a scale from 0 to 9, where 0 represents no infection or lodging, and 9 represents extreme infection or lodging.
**Relative yield performance compared to cv. Barke, the mother variety of null-LOX-1 mutant D112.

Example 6

Analysis of Micro-Malts and Worts Thereof

Micro-malting was performed with 100-g samples of barley mutants A689 and D112, as well as cvs. Barke and Power. The mutant lines were propagated in the field for several seasons in order to obtain sufficient grain material for malting and brewing trials.

Steeping. The conditions were: 8 h wet; 14 h dry; 8 h wet; 10 h dry; 4 h wet in steeping water at 16° C.

Malting. The conditions were: 12 h at 18° C.; 24 h at 16° C.; 24 h at 14° C.; 60 h at 12° C.

Kiln drying conditions were: 12 h at 60° C.; 3 h at 68° C.; 4 h at 74° C.; 3 h at 80° C. The finish malts were subjected to T2N measurements.

In addition, barley and malt samples of mutants A689 and D112, as well as cvs. Barke and Power, barley and malt samples were subjected to analyses by standard EBC methods (see Table 3).

Wort preparation. To test the properties of mutants A689 and D112 in comparison with cv. Power, malt samples of 25-225 g were produced, and used in a laboratory mashing system that comprised an external stirrer and a water bath equipped with a thermostat capable of ramping the temperature in a defined pattern. Mashing was performed in small-scale, with the finished mash separated through a paper filter to obtain the sweet wort. Wort boiling was performed in laboratory-scale using a heating mantel and a round-bottomed flask connected to a reflux cooler.

Figure 7:
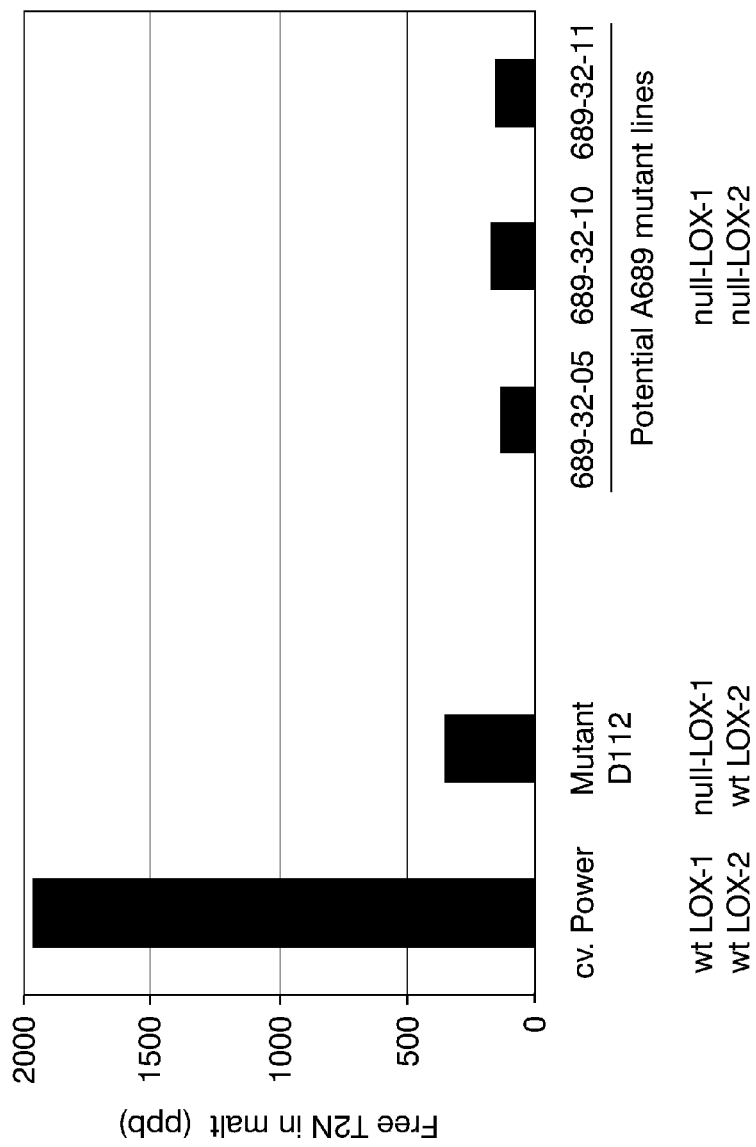
FIG. 7 shows the levels of free T2N formed in micro-malted samples of wild-type barley cv. Power, null-LOX-1 mutant D112, and three potential double null-LOX lines of mutant A689, generation M5. Included are also the LOX-1 and LOX-2 genotypes of the barley samples analyzed (wt: wild-type).
Figure 8:
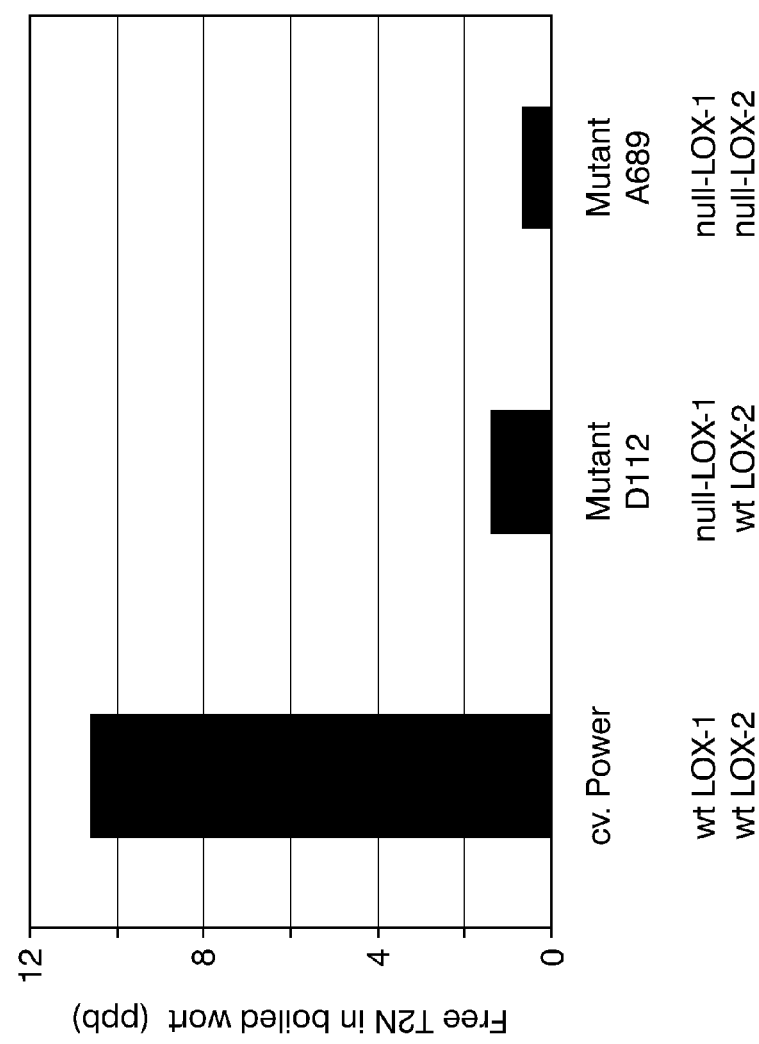
FIG. 8 shows the levels of free T2N formed in samples of boiled wort produced from micro-malted kernels of wild-type cv. Power, null-LOX-1 mutant D112, and double null-LOX mutant A689, generation M5. Shown are also the LOX-1 and LOX-2 genotypes of the barley samples analyzed (wt: wild-type).
Figure 9:
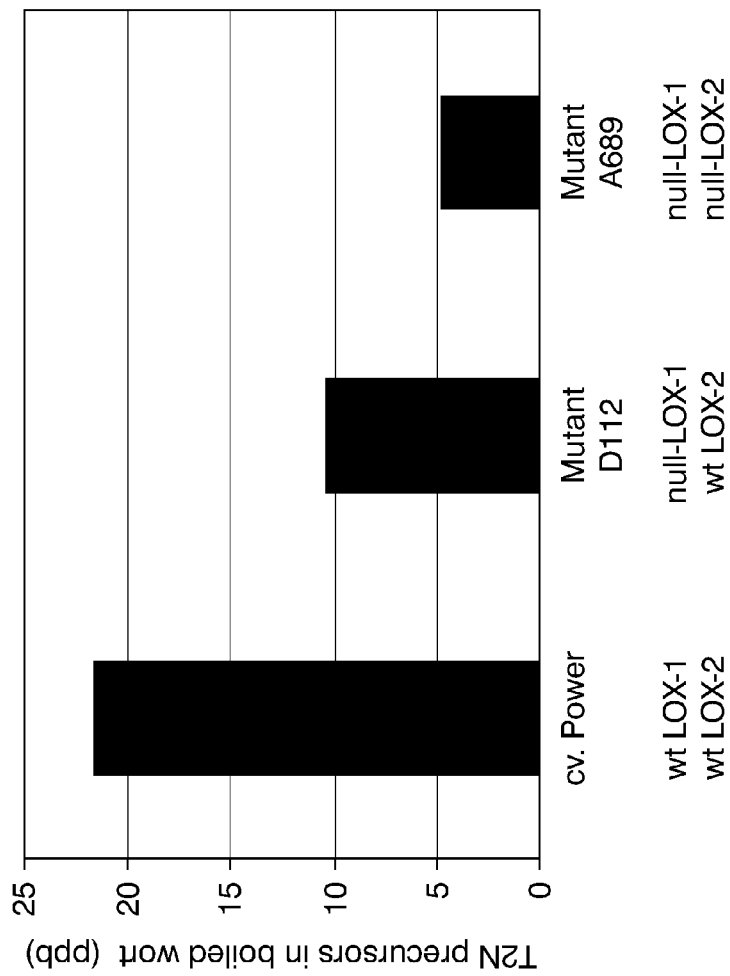
FIG. 9 shows the levels of the T2N precursors in samples of boiled wort produced from micro-malted kernels of wild-type cv. Power, null-LOX-1 mutant D112 and double null-LOX mutant A689, generation M5.

Both sweet and boiled worts were subjected to T2N measurements (cf. FIGS. 7-9). For samples derived from generation M5 grains of double null-LOX mutant A689, there was observed a pronounced ~75% decrease in levels of T2N (average of three A689 mutant lines). Additionally, notable reductions were registered for levels of both free T2N and T2N precursors in wort produced from the micro-malted samples (FIGS. 8-9).

T2N levels were determined by gas chromatography with mass spectrometric detection (GC-MS), following derivatization of carbonyls with O-(2,3,4,5,6-pentafluorobenzyl)-hydroxylamine, essentially as described by Groenqvist et al. (1993).

TABLE 3

Micro-malt analysis.

| Sample | | cv. Power | Mutant A689 | Mutant D112 |
|---|---|---|---|---|
| LOX genotype | | wt LOX-1, wt LOX-2 | null LOX-1, null-LOX-2 | null-LOX-1, wt LOX-2 |
| Barley | | | | |
| Moisture content | %* | 9.3 | 9.5 | 10.5 |
| Protein | %* | 12 | 10.6 | 10.9 |
| Starch | %* | 61.7 | 63.0 | 62.4 |
| Germination, 72 h | % | 100 | 95 | 95 |
| Germination Index | | 9.9 | 6.6 | 8.3 |
| Screening | >2.5 mm | 97 | 98.8 | 91.6 |
| TKW | G | 48.6 | 55.8 | 37.5 |
| β-Glucan | %, dry | 4.0 | 3.6 | 3.3 |
| β-Amylase** | U/g | 1039 | 1458 | 1027 |
| Predicted DP | WK | 385 | 538 | 381 |
| Malt | | | | |
| Malting time | H | 124 | 148 | 124 |
| Malt yield | % | 95.1 | 95.9 | 95.3 |
| Moisture content | %* | 4.8 | 5.6 | 4.6 |
| Protein, dry | %* | 11.2 | 10.3 | 9.9 |
| N, dry | %* | 1.72 | 1.65 | 1.58 |
| Soluble N | %* | 0.67 | 0.62 | 0.64 |
| Wort | | | | |
| Extract | %* | 81.0 | 81.0 | 80.9 |
| β-Glucan | %*, dry | 0.2 | 0.3 | 0.26 |
| Malt modification | % | 95 | 95 | 96 |
| Malt homogeneity | % | 81 | 70 | 71 |
| β-Amylase** | U/g | 956 | 1235 | 937 |
| Predicted DP | WK | 385 | 478 | 379 |
| α-Amylase*** | U/g | 242 | 234 | 264 |

*Measured by standard near infrared transmittance spectroscopy.
**β-Amylase activity was measured using a Megazyme kit (product code K-BETA).
***α-Amylase activity was measured using a Megazyme kit (product code K-CERA).

Example 7

THAs in Beer Produced from Malt of Double Null-LOX Mutant A689

Beer-specific THAs are likely to be derived from linoleic acid (Drost et al., 1974). Several reports have verified that the total content of THAs in beer ranges from 5.7 to 11.4 µg/ml (Hamberg, 1991; and references therein). While 9,12,13-THA normally constitutes 75-85% of the THAs in beer, that of 9,10,13-THA is normally only 15-25%. Other isomers are found in trace amounts.

In beer produced from wort prepared from malt of barley double null-LOX mutant A689 (cf. Example 8, except that a mashing in temperature of 60° C. was used), the concentration of 9,12,13-THA was reduced by 75% compared to the control beer made from malt of cv. Power, and reduced by 45% compared to the null-LOX-1 raw mutant D112 (Table 4). Similar differences were also observed for the 9,10,13-THA isomer. These measurements were carried out using standard HPLC-mass spectrometry analyses (Hamberg, supra).

TABLE 4

THAs in beers produced from malt of cv. Power, null-LOX-1 mutants D112, and double null-LOX mutant A689 (average of 3 measurements).

| | THA | | |
|---|---|---|---|
| | 9,12,13- | 9,10,13- | 9,12,13-:9,10,13- |
| Malt type | ppm | | ratio |
| cv. Power | 3.76 | 1.12 | 3.35 |
| Mutant D112 | 1.72 | 0.94 | 1.80 |
| Mutant A689 | 0.94 | 0.50 | 1.88 |

Example 8

Pilot Malting and Brewing

Malting. The experiments were carried out with kernels of double null-LOX mutant A689, null-LOX-1 mutant D112, and cv. Power (in all cases of harvest 2007). Maltings in 30-kg-large scales were performed in a malt house as follows:

(i) Steeping at 16° C.: 8 h wet; 14 h dry; 8 h wet; 10 h dry; 4 h wet;

(ii) Malting: 12 h at 18° C.; 24 h at 16° C.; 24 h at 14° C.; 60 h at 12° C.;

(iii) Drying: 12 h at 60° C.; 3 h at 68° C.; 4 h at 74° C.; 3 h at 80° C.

Properties of the barley and the malt are listed in Table 5. Examination of the results revealed that the samples fulfilled malt specifications for use of the raw materials in brewing.

TABLE 5

Experimental data.

| Sample | | cv. Power | Mutant A689 | Mutant D112 | cv. Barke |
|---|---|---|---|---|---|
| LOX genotype | | wt LOX-1 wt LOX-2 | null LOX-1 null LOX-2 | null LOX-1 wt LOX-2 | wt LOX-1 wt LOX-2 |
| Barley | | | | | |
| Protein | %* | 12.0 | 10.6 | 10.9 | 10.6 |
| Starch | %* | 61.7 | 63.0 | 62.5 | 64.2 |
| Germination, 72 h | % | 100 | 95 | 85 | 100.0 |
| Germination Index | 1-10 | 9.9 | 6.6 | 8.3 | 9.6 |
| Water sensitivity | % | 1 | 78 | 45 | 14 |
| Grading > 2.5 mm | % | 97.0 | 98.8 | 91.6 | 88.3 |
| TKW | g | 48.6 | 55.8 | 37.5 | 49.5 |
| β-Glucan | %, dry | 4.0 | 3.6 | 3.3 | 3.6 |
| β-Amylase** | U/g | 1039 | 1458 | 1027 | 1093 |

TABLE 5-continued

Experimental data.

| Sample | | cv. Power | Mutant A689 | Mutant D112 | cv. Barke |
|---|---|---|---|---|---|
| Malt | | | | | |
| Steeping and germination time | h | 124 | 148 | 124 | 124.0 |
| Extract | %* | 81.0 | 80.7 | 80.9 | 82.5 |
| Kolbach Index | % | 37.5 | 37.1 | 40.2 | 42.0 |
| Modification | % | 95 | 94 | 97 | 96 |
| Homogenity | % | 81 | 61 | 81 | 83 |
| β-Glucan | %, dry | 0.2 | 0.3 | 0.2 | 0.1 |
| β-Amylase** | U/g | 956 | 1261 | 928 | 985 |
| α-Amylase*** | U/g | 242 | 222 | 262 | 201 |

*Measured by standard near infrared transmittance spectroscopy.
**β-Amylase activity was measured using a Megazyme kit (product code K-BETA).
***α-Amylase activity was measured using a Megazyme kit (product code K-CERA).

Figure 10:
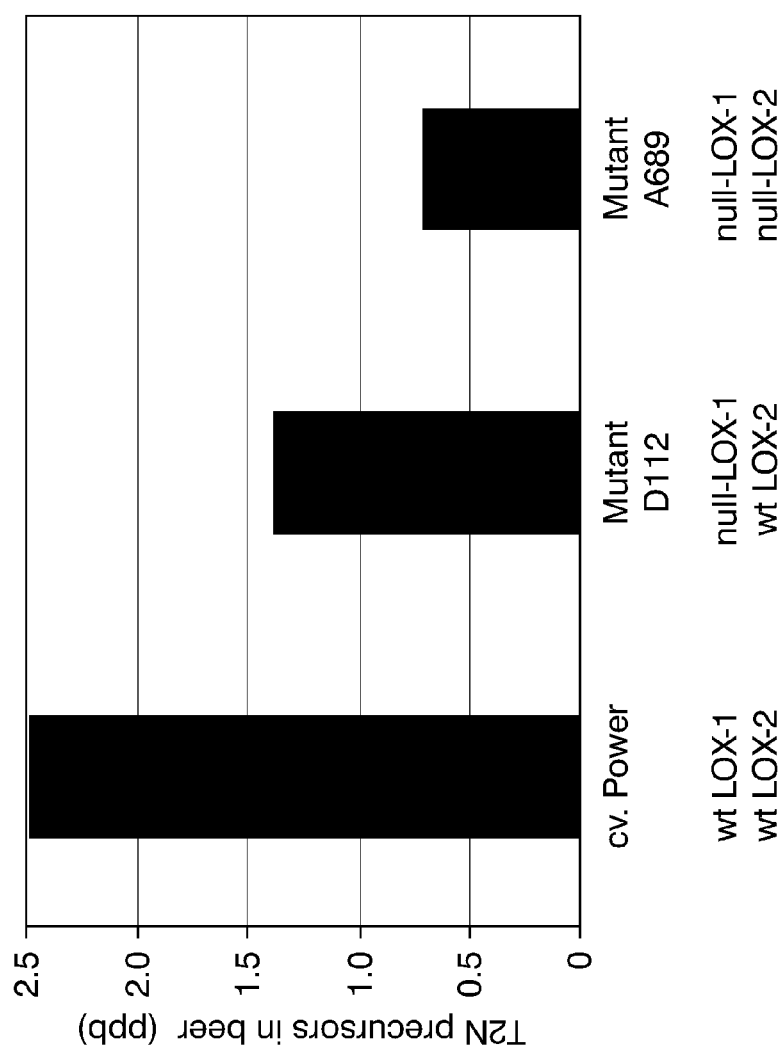
FIG. 10 shows the levels of T2N precursors in beers produced in a 200-l-large brewing experiment using malt of cv. Power, null-LOX-1 mutant D112, and double null-LOX mutant A689. Shown are the LOX-1 and LOX-2 genotypes of the malts used (wt: wild-type).

Pilot brewing with malt. An initial 200-l trial, with key results thereof illustrated in FIGS. 10A,B, involved the following steps:
 (i) Wort preparation;
 (ii) Wort separation;
 (iii) Wort boiling;
 (iv) Fermentation;
 (v) Lagering;
 (vi) Bright beer filtration; and
 (vii) Bottling.

Worts were prepared using 30-kg-large malt samples of wild-type cv. Power, null-LOX-1 mutant D112, and double null-LOX. Mashing-in was at 48° C. for 20 min, followed by 18 min of heating in which the temperature was raised from 48° C. to 67° C. The saccharification pause at 67° C. was for 30 min, followed by a heat-up step to 72° C. for 5 min, and a rest for 15 min before mashing-off at 78° C. The brewing steps as referred to herein above—i.e. wort boiling and filtration, whirlpool separation, fermentation, lagering, and packaging in green glass bottles—were according to specifications for standard brewing practice.

The T2N precursors of the finished beers were determined (FIG. 10), using the same experimental set-up as described in Example 6. Results of the instant large-scale experiment showed the same trend in relative levels of the T2N precursors as that in boiled wort of micro-malted kernels (compare FIGS. 9 and 10), again revealing notably lower values for both null-LOX-1 mutant D112 and double null-LOX mutant A876 in comparison with that of cv. Power. More specifically, the T2N precursors were reduced by ~40% and ~70% in beer samples of null-LOX-1 and double null-LOX, respectively, when compared to beer of wild-type cv. Power malt.

Also, levels of free T2N were measured in the aforementioned pilot-brewed beers, again showing the same trend as observed for the T2N potential—namely that beers made of null-LOX-1 and double null-LOX malt were notably lower in T2N than that brewed with malt of cv. Power. With respect to T2N levels, beer of double null-LOX malt was accordingly again demonstrated to be superior to that of null-LOX-1.

A separate aim was to establish whether beers were superior in taste qualities after forced aging when these were produced in 200-l-scale using a double null-LOX raw material. The specialized beer taste panel as described in Example 9 was therefore asked to evaluate the pilot-brewed, normal beers for papery off-flavor taste after forced-aging at 37° C. for one week, using a score from 0 (absent) to 5 (extreme). While beer of cv. Power was found to yield a papery score of 1.6, those of null-LOX-1 and double null-LOX were 1.2. and 0.6, respectively. This result substantiated the superiority of the double null-LOX raw material for production of flavor-stable beer.

Example 9

Comparisons of Normal and Barley-Brewed Beers

Kernels of unmalted double null-LOX mutant A689, null-LOX-1 barley mutant D112, and wild-type cv. Power were applied to identical processes of barley brewings, each utilizing 25 kg milled, unmalted barley as the raw material for production of 200 l beer (for comparative purposes, 30 kg of milled malt was used to produce 200 l of normal beer in a parallel running experiment). The aim was not only to compare properties of wort and beer from barley and malt-derived brewings, but also to determine whether the above-mentioned mutants could confer improved off-flavor chararacteristics in both barley-brewed and normal, finished beer. The 200-l-large brewing trials comprised the same production steps as listed above in Example 8, with specific details described herein below.

Mashing and brewing with barley. In the instant experiment, wort was prepared in the presence of the enzyme mixture Ondea Pro (Novozymes; batch no. NFNG0005), added at mashing-in according the recommendations provided by manufacturer (i.e. 87.5 g enzyme mix per 80 l $H_2O$). The mashing conditions were: mashing-in at 54° C. for 30 min; 10 min of heating to raise the temperature to 64° C.; incubation for 45 min 64° C.; heating up to 78° C. for 13 min; 10 min pause at 78° C. The brewing steps of wort filtration and boiling, whirlpool separation, fermentation, lagering, and packaging in green glass bottles were according to specifications for standard brewing practice.

Standard malting, mashing, and brewing. Malting utilized barley kernels of double null-LOX mutant A689, null-LOX-1 mutant D112, and wild-type cv. Power (all from harvest 2009). Steeping incubation times at 16° C. were: 8 h wet; 14 h dry; 8 h wet; 10 h dry; 4 h wet. Malting conditions were: 12 h at 18° C.; 24 h at 16° C.; 24 h at 14° C.; 60 h at 12° C. Kiln drying conditions were: 12 h at 60° C.; 3 h at 68° C.; 4 h at 74° C.; 3 h at 80° C. Barley and malt analyses of the aforementioned raw materials were performed according to standard EBC methods, with the results listed in Table 6. All of the malts were considered suitable for brewing.

Mashing conditions were: initial incubation at 48° C. for 20 min; a 18-min-long heating-up to 67° C.; 30 min incubation at 67° C.; then heating-up to 72° C. for 5 min; 15 min of incubation at 72° C.; heating-up to 78° C. for 6 min; ending with a 5-min incubation at 78° C. The brewing steps of wort filtration and boiling, whirlpool separation, fermentation, lagering, and packaging in green glass bottles were according to specifications for standard brewing practice.

Analysis of boiled wort—Free T2N. T2N levels in the extracts were determined by gas chromatography with mass spectrometric (GC-MS) detection following solid phase extraction on a C18 column, and derivatization of carbonyls with O-(2,3,4,5,6-pentafluorobenzyl)-hydroxylamine, essentially as described by Groenqvist et al. (1993); see also Example 5.

Figure 11:
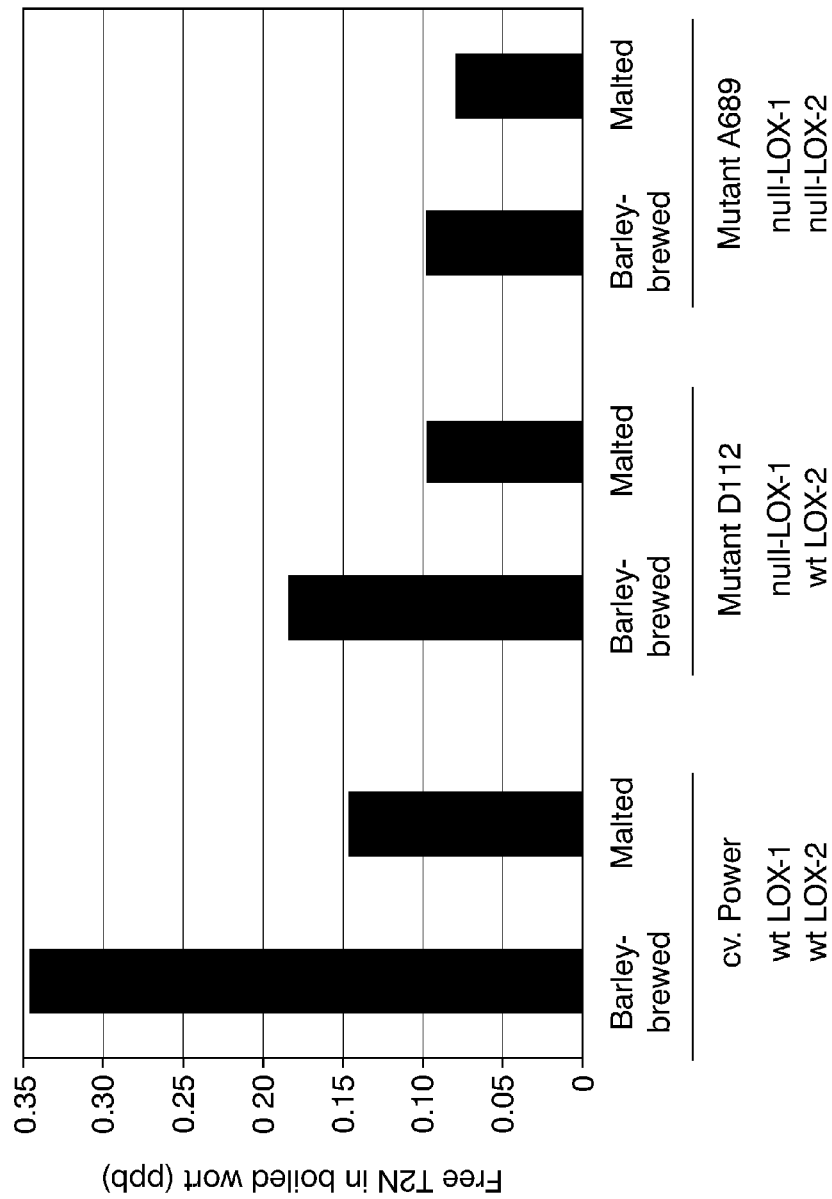
FIG. 11 shows a comparison of the free T2N levels in aliquots of the indicated samples taken from 200-l-large boiled worts, produced by barley brewing or by normal malting and mashing. Shown are the LOX-1 and LOX-2 genotypes of the raw materials used (wt: wild-type).

In a direct comparison with samples of cv. Power and null-LOX-1 mutant D112, there was observed a notable reduction in free T2N in boiled wort produced from both barley-brewed and normal malt of double null-LOX mutant A689 (FIG. 11). When compared with barley-brewed, boiled wort produced from null-LOX-1 mutant D112, that of double null-LOX mutant A689 exhibited a ~45% reduction in the level of free T2N (for the corresponding malted samples, the reduction was ~15%).

Similarly, a ~72% reduction was noted for free T2N in beer of double null-LOX mutant A689 in comparison with that of cv. Power (for the corresponding malted samples, the reduction was ~45%).

Analysis of boiled wort—T2N precursor. T2N precursors in boiled, barley-brewed and normal wort samples of cv. Power, null-LOX-1 mutant D112, and double null-LOX mutant A689 were determined by GC-MS following derivatization of carbonyls with O-(2,3,4,5,6-pentafluorobenzyl)-hydroxylamine, essentially as described by Gronqvist et al. (supra).

Figure 12:
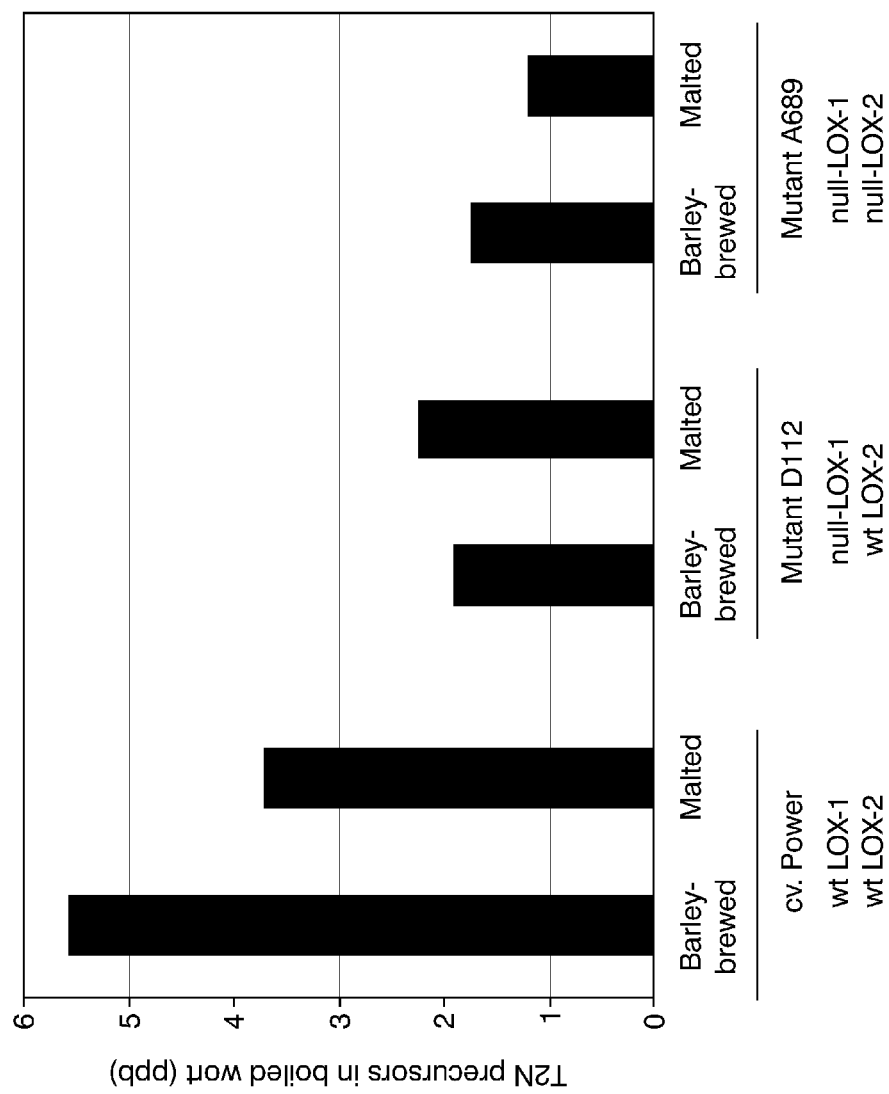
FIG. 12 shows a comparison of the levels of T2N precursors in the indicated sample aliquots taken from 200-l-large boiled worts (cf.

As illustrated in FIG. 12, the T2N precursors of boiled, barley-brewed and normal worts were markedly lowest in samples from double null-LOX mutant A689, amounting to a reduction of ~70% in comparison with that of wild-type cv. Power (reductions were also registered in comparisons with samples from null-LOX mutant D112).

Analysis of barley-brewed beer only—Free T2N, forced aging. Bottled beer derived from fermentations of barley-brewed wort samples—and comprising similar levels of sulfite—were analyzed within one month for production of T2N over time.

The aforementioned barley-brewed beers were forced-aged at 37° C. to follow the development of free T2N, as described herein above.

Figure 13:
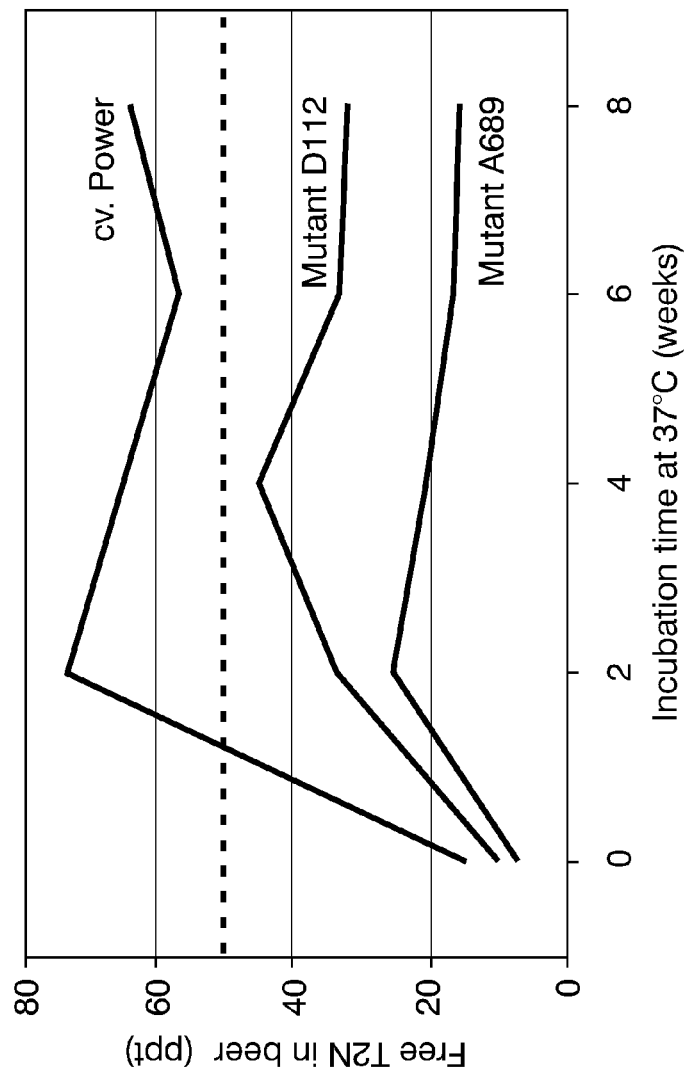
FIG. 13 shows aspects of T2N development in beers from 200-l-large brewing trials, using the indicated barley cultivar and mutants as raw materials. (A) Analyses of barley-brewed beer only, focusing on the development of free T2N during forced aging. The taste threshold level of T2N at 50 ppt is indicated by a horizontal, dashed line. In a separate experiment was compared levels of T2N precursors in fresh beers of barley brews and normal brews (B); in (C) is shown the levels of freeT2N in fresh beers (white bars) compared with levels after two weeks at 37° C. (black bars). Shown are also the LOX-1 and LOX-2 genotypes of the raw materials used (wt: wild-type).
Figure 13:
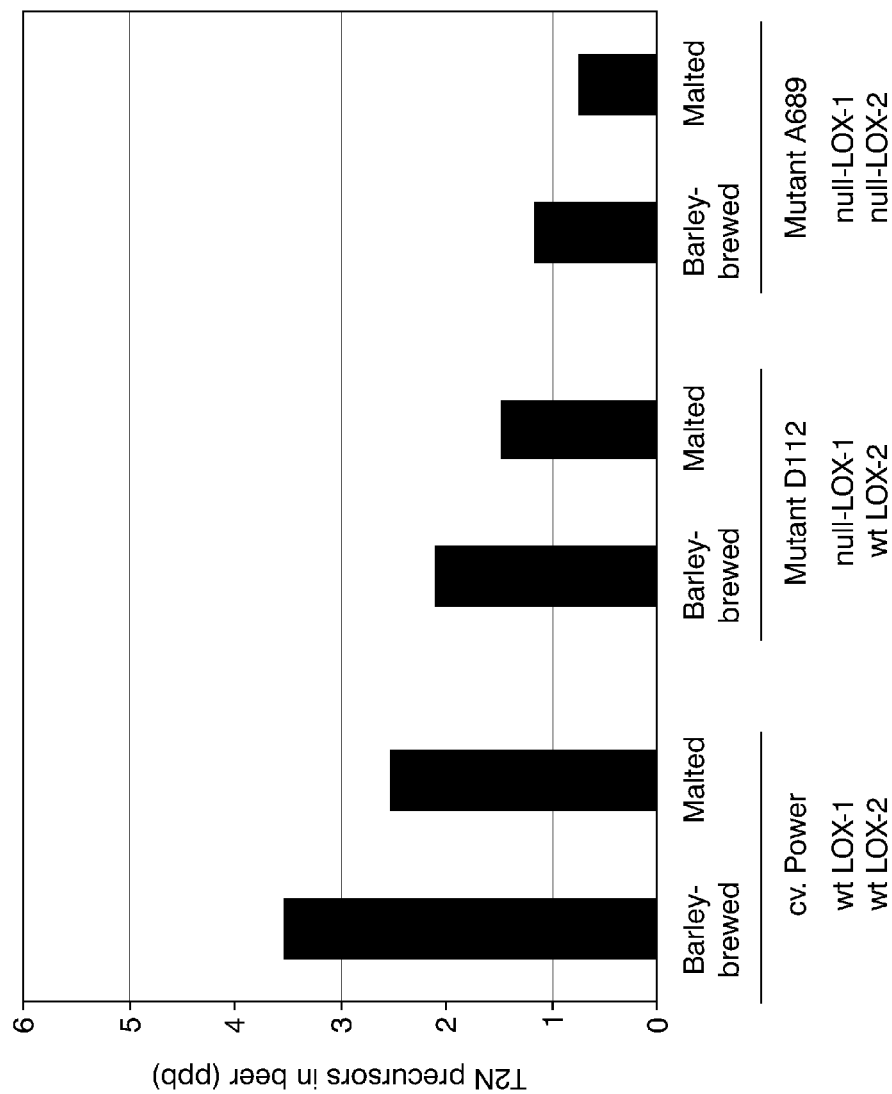
Figure 13:
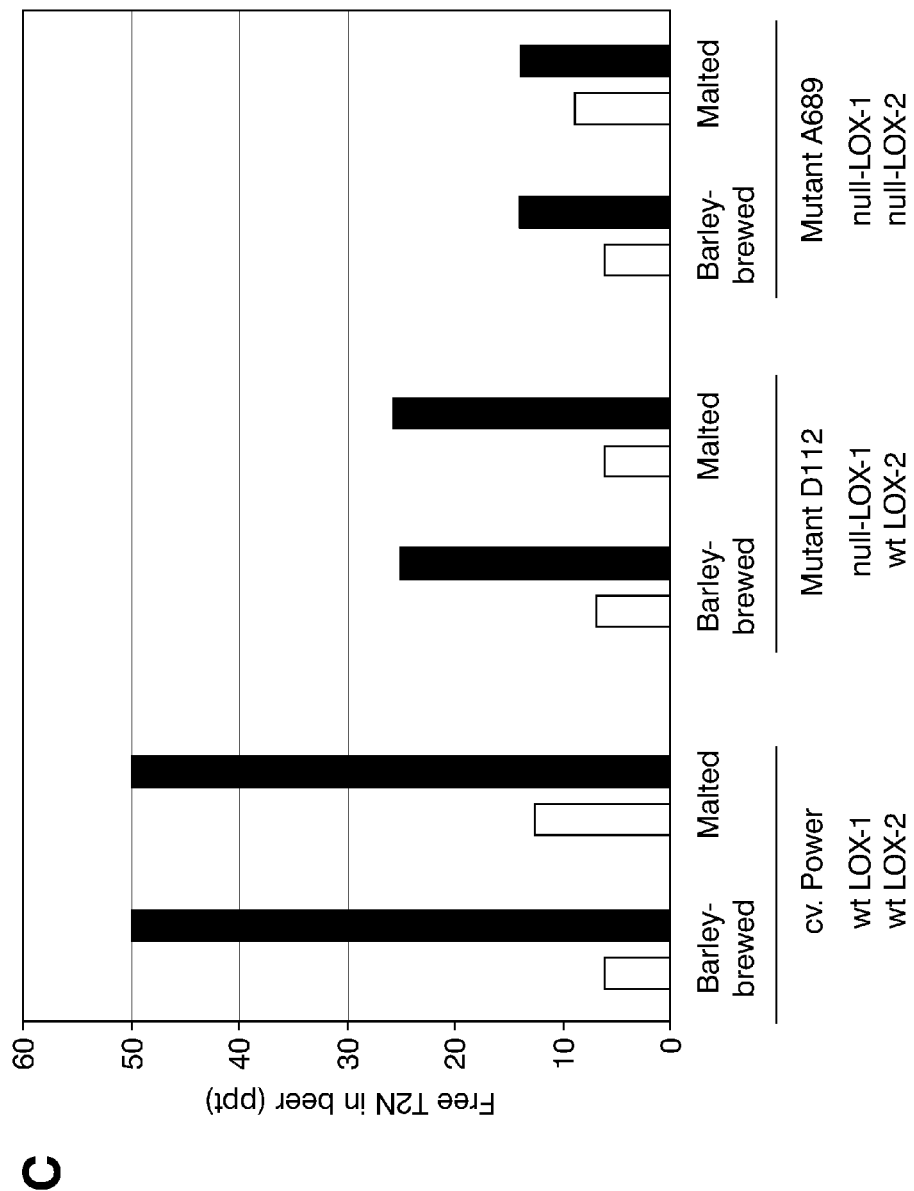

As illustrated in FIG. 13A, the three types of barley-brewed beers were easily distinguished as a result of pronounced differences in the kinetics of T2N development. While the reference beer of cv. Power barley performed as expected (64 ppt T2N after 8 weeks at 37° C.)—with T2N levels 10-20% higher than a similar malt-based beer (not shown)—an unexpected and remarkably low development of T2N was observed in the barley beers derived from double null-LOX mutant A689 (16 ppt T2N after 8 weeks at 37° C.), corresponding to a 75% reduction in free T2N of the final beer. For the barley-brewed beer of null-LOX-1 mutant D112 as compared with the same type of beer of wild-type kernels, there was 52% less free T2N over 8 weeks.

The forced-aging experiment emphasized the notable differences among the beers analyzed. Already after 1.5 weeks, the T2N level of the reference, barley-brewed beer of cv. Power exceeded the taste threshold level of ~50 ppt, while that of double null-LOX mutant 689 levelled-off at ~16 ppt T2N, thus far better than 32 ppt T2N for the barley-brewed beer of null-LOX-1 mutant D112.

Comparisons of barley-brewed and normal beer—T2N precursor. In FIG. 13B is provided a summary on data specifying levels of T2N precursor in fresh beer of barley-brewed and malted raw materials, both produced in a 200-l volume. Again, double null-LOX raw materials were superior in measured properties, actually with lower T2N potentials in barley-brewed beers (1.2 ppb), than in beers produced with null-LOX-1 malt (1.5 ppb).

Comparisons of barley-brewed and normal beer—Forced development of T2N. Also in this case, i.e. forced aging of beer at 37° C., there was a marked difference between beers made of wild-type and mutant raw materials (FIG. 13C). While both barley-brewed and normal beer of wild-type cv. Barke kernels exhibited ~50 ppt T2N after two weeks, the corresponding values were reduced by ~50% and ~75% for raw materials of null-LOX-1 mutant D112 and double null-LOX mutant A876, respectively. The same trend was observed after three weeks of forced-aging. Accordingly, it was substantiated that the use in beer production of raw materials deficient in LOX enzymes represents a superior way to drastically reduce the development of T2N during aging. And further in this respect, the raw materials of double null-LOX mutant A876 are superior to those of null-LOX-1 mutant D112.

Comparisons of barley-brewed and normal beer—THAs. Beer-specific THAs derived from linoleic acid were already described several decades back in time (Drost et al., 1974). Since then, various reports have verified that the total content of THAs in beer ranges from ~5-12 ppm (Hamberg, 1991; and references therein). While 9,12,13-THA normally constitutes 75-85% of the THAs in beer, that of 9,10,13-THA amounts to 15-25%; other isomers are found in trace amounts.

Figure 14:
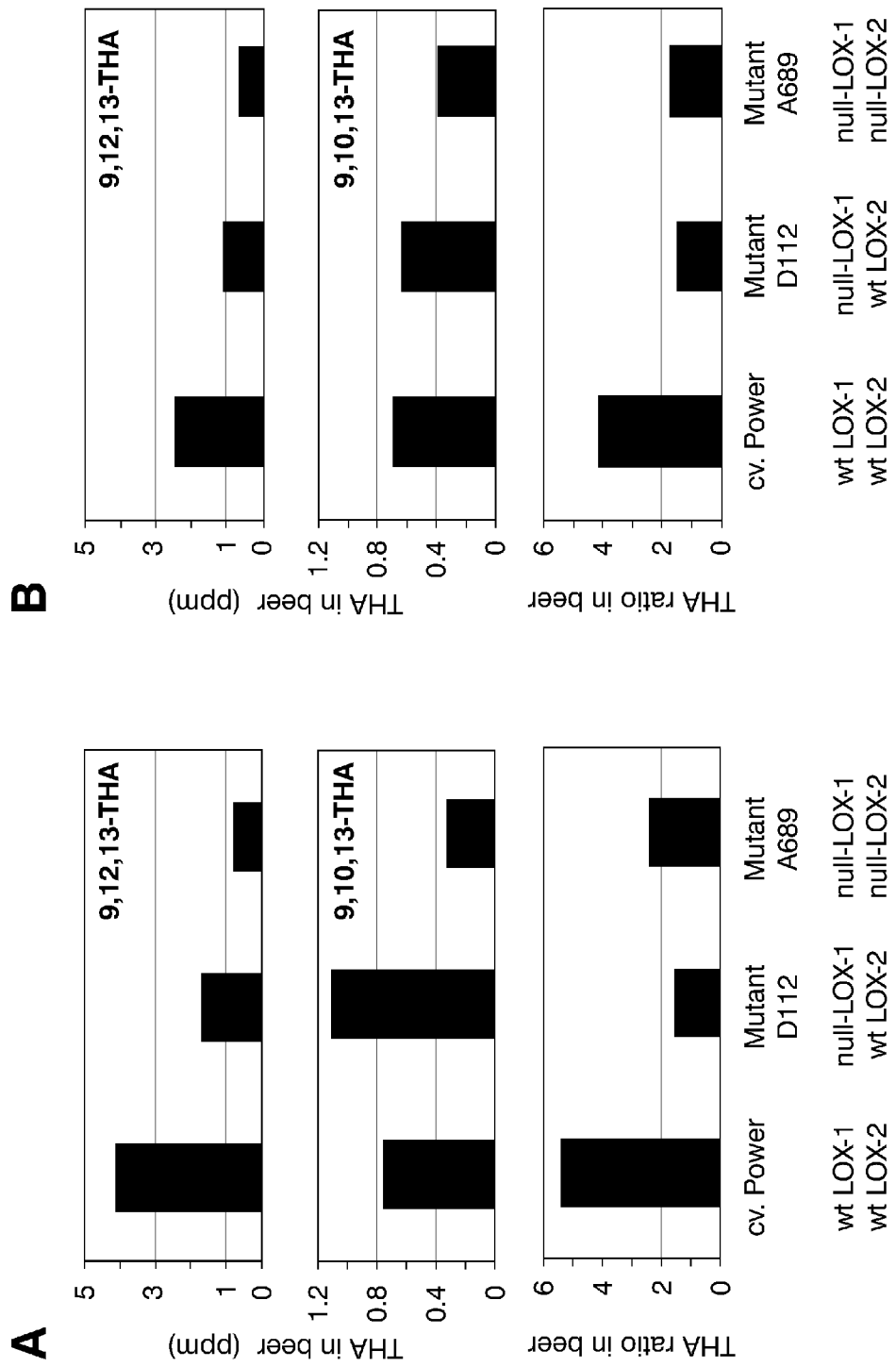
FIG. 14 shows a comparison of THA levels and ratios in both barley-brewed beers (A), and in beers produced using normal malt (B). 9,12,13- and 9,10,13-THAs are generated by partially unknown reactions of the LOX-1 and LOX-2 pathway, respectively.

In fresh barley-brewed beers of a 200-l-scale experiment with raw materials of null-LOX-1 mutant D112 and double null-LOX mutant A689, the levels of LOX-1 and LOX-2 pathway-derived 9,12,13- and 9,10,13-THA were found to be reduced by ~60% and ~80%, respectively, in comparison with that of the control of cv. Power (FIG. 14A). A surprisingly high level of 9,10,13-THA, the main THA product from the LOX-2 branch of the LOX pathway, was measured in barley-brewed beer of null-LOX-1 mutant D112, namely +47% in comparison with that of beer from cv. Power. The result contrasted that obtained with double null-LOX mutant A689, for which there was measured a 60% decrease, again in comparison with cv. Power. Results of a separate experiment confirmed the aforementioned conclusion. The molecular basis for the observation remains elusive, but some cellular mechanism(s) may be speculated to be activated to compensate for the absence of LOX-1 in mutant D112 by enhancing the synthesis of enzymes involved in 9,10,13-THA formation.

For that reason, barley-brewed beer produced from double null-LOX mutant A689 generated a significantly lower 9,12, 13-THA:9,10,13-THA ratio in comparison with cv. Power.

Determination of the 9,12,13-THA and 9,10,13-THA levels, combined with determination of their ratio, represents a convenient, initial tool to indicate whether a beer is produced using barley of double null-LOX mutant A689. However, a firmer assessment on that issue may involve additional examinations as described in the instant application.

In beer produced from malt of double null-LOX mutant A689, the concentration of LOX pathway-derived 9,12,13- and 9,10,13-THA was found to be reduced by ~75% and ~40%, respectively, as compared to the control beer of malted cv. Power (FIG. 14B). In said beer, there can also be calculated a very low 9,12,13:THA:9,10,13-THA ratio when compared to beer of cv. Power. In general, but not in all instances, THA levels are slightly lower in malt-based beers than in barley-brewed beers (compare FIGS. 14A and B).

Analysis of barley-brewed beer only—Taste and flavor stability. A panel of flavor specialists evaluated the aforementioned, forced-aged barley-brewed beers of cv. Power, null-LOX-1 mutant D112, and double null-LOX mutant A689.

In general, the taste panel found satisfactory flavor profiles for all types of the fresh and the forced-aged beers after 1 week at 37° C. However, the "papery" taste scores were significantly higher for the reference beer than for that produced using malt of double null-LOX mutant A689 and null-LOX-1 mutant D112 (FIG. 15A), i.e. the reference beer was charaterized by a more intense taste of said off-flavor. In general, the taste panel preferred the barley-brewed beer produced from double null-LOX barley of mutant A689.

Figure 15:
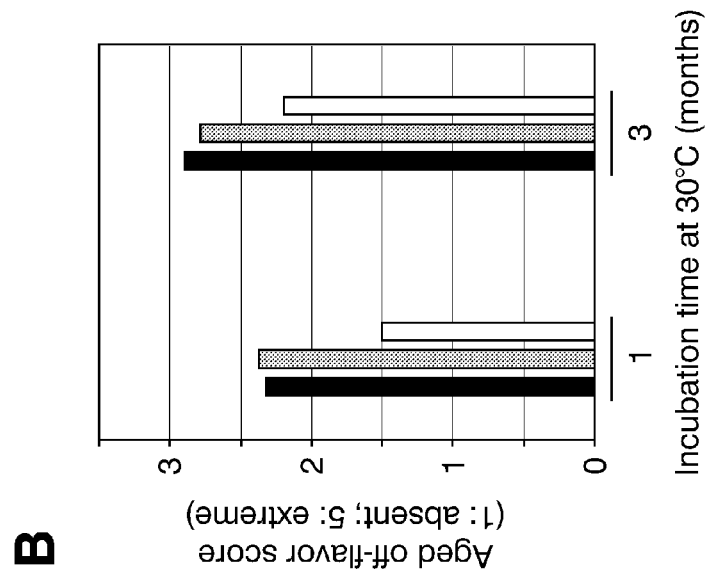
FIG. 15 shows an illustration on the development over time of the off-flavors "papery" (A) and "aged" (B) in 200-l-scale barley-brewed beer, using the raw materials cv. Power (black bars), null-LOX-1 (grey bars), and double null-LOX (white bars). A specialized beer taste panel judged the beers, using a scale from 0 (no off-flavor) to 5 (extreme off-flavor).
Figure 15:
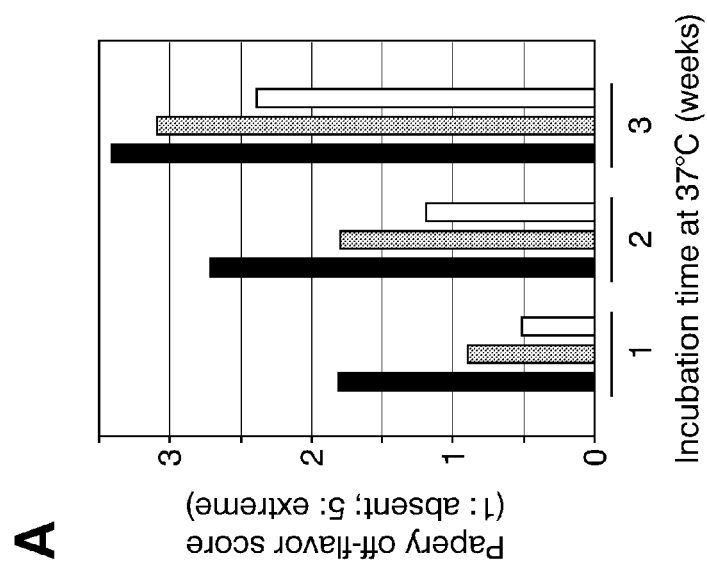

The trained taste panel also evaluated the more general "aged" taste after beer storage for 1 month and 3 months at 30° C., again demonstrating that said flavor scores were significantly higher for the beers of cv. Power and null-LOX-1 than that of double null-LOX barley mutant A689 (FIG. 15B).

In summary, the improved flavor stability of barley-brewed and normal beer of double null-LOX mutant 689 is remarkable—simply because of the low T2N levels following storage, particularly at high temperatures. Accordingly, the actions of LOX-1 and LOX-2 in brewing set-ups represent key determinants for the appearance of T2N, a principal off-flavor compound in aged beer.

Comparisons of barley-brewed and normal beer—Beer foam. Barley-brewed and control beers were degassed for 20 min in an ultrasonic bath before 50 ml $H_2O$ was added to 150 ml beer. The mixture was slowly poured into a foam tower, consisting of a 16-cm-long, 7-cm-wide glass tube (with a glass filter and connector at the bottom and top, respectively). $N_2$ gas, at a flow rate of 400 ml min$^{-1}$, was bubbled through said mixture from the bottom to generate beer foam. This was led through a tube, and collected in a graded sedimentation cone positioned on a weight.

Figure 16:
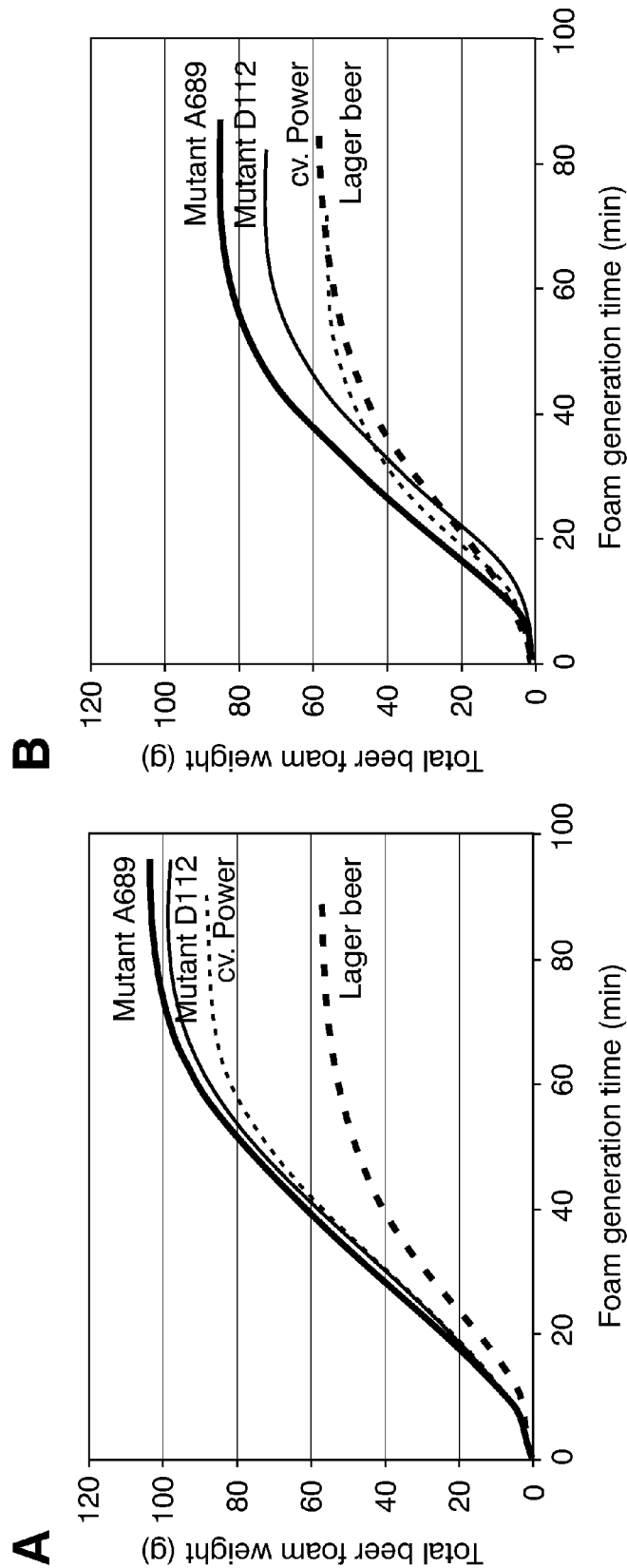
FIG. 16 shows how foam develops in barley-brewed beers (A), and in malt-based beers (B). In both experiments, a commercial lager beer served as reference (thick dashed line), in comparison with beer produced using raw materials of cv. Power (thin dashed line), null-LOX-1 (thin unbroken line), and double null-LOX (thick unbroken line).

The total foam weight was recorded at time intervals of 5 min until foam development ceased, both for barley-brewed beer (FIG. 16A), and for malt-brewed beer (FIG. 16B). In either case, beer of raw materials from double null-LOX mutant A689 generated the most foam. Actually, foam development was better in barley-brewed beer than in the comparable malt-based beer.

TABLE 6

Barley, malt, wort, and beer analyses.

| Sample | | cv. Power | Mutant D112 | Mutant A689 |
|---|---|---|---|---|
| Barley analyses | | | | |
| Protein | %* | 11.7 | 11.2 | 10.1 |
| Starch | %* | 63.3 | 62.9 | 62.7 |
| Germination at 72 h | % | 98 | 99 | 99 |
| Germination Index | 1-10 | 8.4 | 7.8 | 7.8 |
| Water sensitivity | % | 9 | 17 | 24 |
| Grading >2.5 mm | % | 96.2 | 98.9 | 98.0 |
| TKW | g | 48.2 | 54.2 | 47.7 |
| β-Amylase (barley)* | U/g | 1039 | 979 | 1491 |
| trans-2-Nonenal† | ppb | 270 | 190 | 150 |
| Malt, wort, and beer analyses | | | | |
| Steeping and germination | h | 120 | 120 | 120 |
| Extract | %* | 81.5 | 81.2 | 81.4 |
| Soluble N | %, NIT* | 0.67 | 0.63 | 0.64 |
| Modification | % | 96 | 97 | 97 |
| Homogenity | % | 88 | 86 | 81 |

TABLE 6-continued

Barley, malt, wort, and beer analyses.

| Sample | | cv. Power | Mutant D112 | Mutant A689 |
|---|---|---|---|---|
| β-Amylase** | U/g | 768 | 865 | 1007 |
| α-Amylase*** | U/g | 175 | 172 | 200 |
| trans-2-Nonenal† | ppb | 1100 | 470 | 390 |
| Alcohol | % | 3.94 | 3.87 | 3.80 |
| Real extract | % Plato | 3.76 | 3.80 | 3.30 |
| Ph | | 4.3 | 4.2 | 4.2 |
| Color | EBC U | 7.1 | 8.2 | 5.2 |
| Original extract | % Plato | 11.42 | 11.33 | 10.72 |
| Real degree of fermentation | % | 68.4 | 67.8 | 70.4 |
| Alcohol | % (vol.) | 4 | 3 | 4 |
| $CO_2$ | g/l | 5.6 | 6.1 | 5.9 |
| $SO_2$ | ppm | 4 | 4 | 5 |
| Diacetyl | ppm | 23 | 21 | 10 |

*Measured by standard near infrared transmittance spectroscopy.
**β-Amylase activity was measured using a Megazyme kit (product code K-BETA).
***α-Amylase activity was measured using a Megazyme kit (product code K-CERA).
†Measured basically as described by Groenqvist et al. (1993).

Example 10

The Gene for LOX-2 in Barley Mutant A689 is Mutated

The genomic nucleotide sequence encoding LOX-2 of cv. Barke (SEQ ID NO:1), and that of double null-LOX mutant A689 (SEQ ID NO:2), were obtained as described hereinafter. The sequences obtained were subsequently compared in order to determine the molecular basis for the null-LOX-2 genotype of mutant A689, the phenotype of which is characterized by the absence of LOX-2 activity in the germinating barley grain.

For said comparative purposes, barley genomic DNAs from mutant A689 and wild-type cv. Barke were isolated from leaflets of seedlings using the Plant DNA Isolation Kit (Roche). The two 3331-bp sequences covering the protein coding regions for LOX-2 in the genomic DNAs of mutant A689 and cv. Barke were amplified by PCR using the primers 5'-CGCAGCGAGCTAACTTAGAAGCGTGCCACA-3' (SEQ ID NO:3) and 5'-CCTCATGCCTTTGTGCTATCCT-TGCTTGCT-3' (SEQ ID NO:4); basis for the primer sequences comprised the genomic sequence of the gene for LOX-2 (i.e. SEQ ID NO:1).

Figure 17:
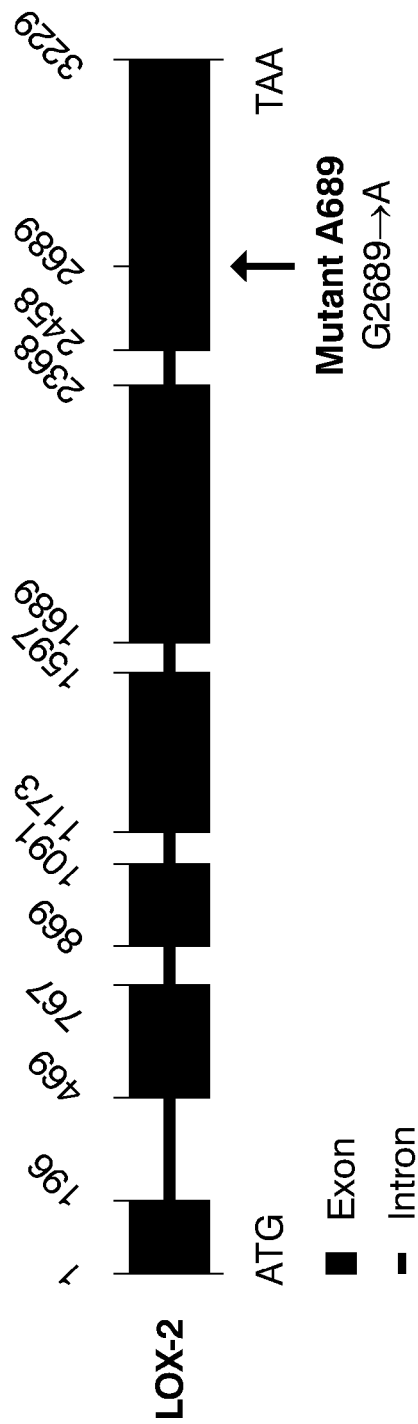
FIG. 17 shows a map on the organization of the genomic barley gene for LOX-2, focusing on the region spanning the start codon (ATG) and the stop codon (TAA). The 3229-bp sequence was found to consist of 6 exons (filled boxes), and 5 introns (lines). The mutation identified in the gene for LOX-2 of double null-LOX mutant A689 is indicted by a vertical arrow. Notably, double null-LOX mutant A689 also contains a premature translational stop codon in the gene for LOX-1 (cf. mutant D112 as illustrated in FIG. 15 of U.S. Pat. No. 7,420,105).

The PCR reactions consisted of 100 ng genomic DNA resuspended in 20 μl reaction buffer containing 5 μmol of each primer and 3.0 U FailSafe polymerase (Epicentre). The PCR amplifications were carried out in an MJ cycler, using the following parameters: 30 sec at 98° C. for 1 cycle; 15 sec at 98° C.; 30 sec at 65° C.; and 60 sec at 72° C. for 30 cycles; 10 min at 72° C. for 1 cycle. The resulting PCR products were separated on 1% agarose gels, and DNA fragments corresponding in length to the amplicons were purified using the Qiaex II gel extraction kit (Qiagen), and inserted into the plasmid vector pCR Blunt II TOPO Blunt (Invitrogen). The coding regions were applied to dideoxynucleotide chain termination reactions with specific oligonucleotide primers, followed by sequence determination on a MegaBACE 1000 DNA sequencer (GE Biosystems). In FIG. 17 is shown a schematic illustration of the genomic sequence spanning the start and stop codons of the region encoding LOX-2. Sequence comparisons were performed using the Lasergene sequence analysis software package ver. 5.2 (DNASTAR), revealing one point mutation in the form of a G→A substitution at position 2689 of SEQ ID NO: 2 in exon 6 (FIG. 17).

The wild-type sequence for LOX-2 encodes a 864-residue-long protein (SEQ ID NO:5), with a predicted mass of 96.7 kDa. While the mutation at position 684 in the LOX-1—encoding sequence of mutant D112 caused the introduction of a premature stop codon, that of the LOX-2—encoding gene of mutant A689 resulted in a C-terminal truncation of 180 amino acids, thus encoding a 76.8-kDa protein (SEQ ID NO:6).

Table 7 provides a summary on the molecular differences related to the gene of LOX-2 of the wild-type barley, null-LOX-1 barley mutant D112 (described in WO 2005/087934), and barley mutant A689 (double null-LOX).

TABLE 7

Molecular data on wild-type and mutant barley.

| Property | Wild-type barley | Mutant D112* | Mutant A689 |
|---|---|---|---|
| LOX genotype | wt LOX-1, wt LOX-2 | null-LOX-1, wt LOX-2 | null-LOX-1, null-LOX-2 |
| Base mutation** | | | |
| LOX-1 | — | G3474→A | G3474→A |
| LOX-2 | — | — | G2689→A |
| Protein data*** | | | |
| LOX-1 | 862 aa (96.4 kDa) | 665 aa (74.2 kDa) | 665 aa (74.2 kDa) |
| LOX-2 | 864 aa (96.7 kDa) | 864 aa (96.7 kDa) | 684 aa (76.8 kDa) |

*Mutant A689's mother line, Ca211901, exhibits identical properties.
**Sequence numbering according to SEQ ID NO: 1 of WO 2005/087934 for the LOX-1 gene, and for the LOX-2 gene according to SEQ ID NO: 1 of the present publication.
***Predicted protein lengths in amino acids (aa), with the corresponding, predicted masses in parentheses.

Example 11

Genetic Detection of Barley Double Null-LOX Mutant A689

Figure 18:
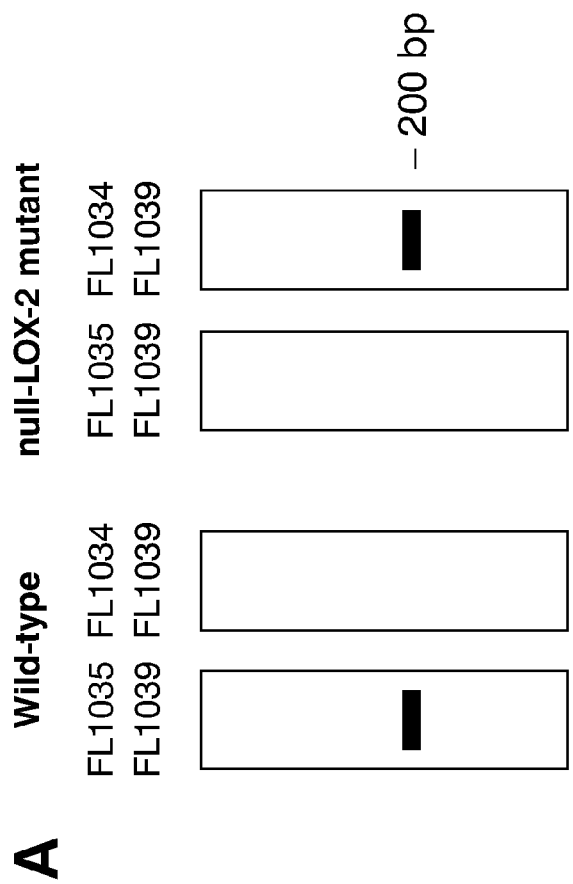
FIG. 18 shows how genotype analysis can be used to identify null-LOX mutants. Focus concerns SNP-assisted detection of a double null-LOX barley plant, i.e. a way to achieve the combined detection of a G→A mutation at position 3474 of the LOX-1 gene, and a G→A mutation at position 2689 of the LOX-2 gene. (A) Diagram of agarose gel electrophoresis of PCR fragments amplified form the indicated template DNA using the indicated primer pairs, i.e. the wild-type LOX-2 gene can be amplified by using primers FL1035 and FL1039, while the null-LOX-2 mutant gene can be amplified using primers FL1034 and FL1039. (B) Diagram to illustrate how PCRs with primer pair FL820 and FL823 (containing a 3' base complementary to the null-LOX-1—specific mutation as shown by an asterisk), and primer pair FL1034 (containing a 3' base complementary to the null-LOX-2 mutation as illustrated by an asterisk) and FL1039 can generate PCR products of 166 by and 200 bp, respectively, provided the presence of said null-LOX mutations. (C) Depiction of the result following agarose gel electrophoresis of marker DNA (lanes 1 and 4), and that of PCR-amplified DNA of double null-LOX mutant A689 using the aforementioned primer combinations for detection of the null-LOX-1 and null-LOX-2 mutations (lane 2). PCR reactions of wild-type barley yielded no corresponding PCR products (lane 3).
Figure 18:
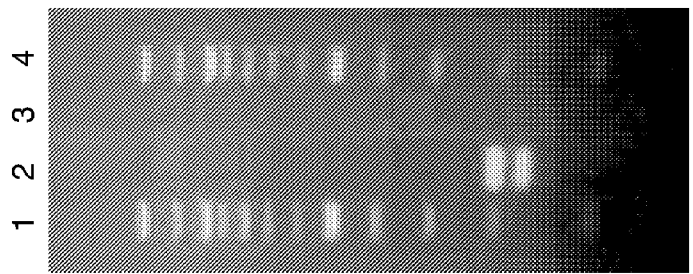
Figure 18:
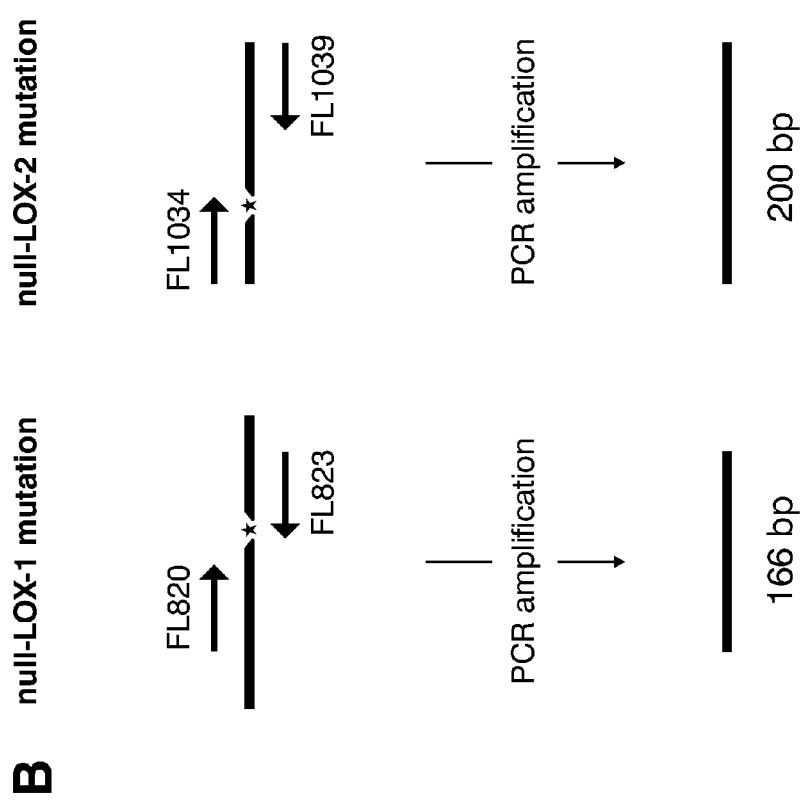

The single nucleotide polymorphism (SNP) assay represents a convenient way to identify plant mutants. By SNP is here meant a mutation point with at least two different nucleotides at one locus. Said assay is based on the combined use of two sets of PCR reactions using genomic DNA as template. Both reactions contain a locus-specific primer, and one of the two SNP primers (one for each allele of the sequence). Two sets of PCR reactions are performed per plant line, with the result of a PCR reaction being either that the SNP primer binds to sequences of the mutant or to the wild-type allele (FIG. 18A). In one of several methods, SNP analysis can be based on the identification of mutant lines by evaluating the banding pattern following gel electrophoresis of PCR products.

Genomic barley DNA from a barley breeding line and from the wild-type cv. Quench were isolated from leaf tissues of seedlings, using the Plant DNA isolation kit (Roche) according to the manufacturer's recommendations. The oligonucleotide primers used to amplify the SNP of the wild-type LOX-2 gene were 5'-ACCTCAAGGACGCGGCGTGG-3' (SEQ ID NO:7) and 5'-GAGCGAGGAGTACGCGGAG-3' (SEQ ID NO:8), while those for the corresponding mutant gene were 5'-ACCTCAAGGACGCGGCGTGA-3' (SEQ ID NO:9) and 5'-GAGCGAGGAGTACGCGGAG-3' (SEQ ID NO:8). These primer combinations were used in PCR reactions to amplify DNA fragments of 200 by comprising parts of the coding regions for LOX-2 of double null-LOX mutant A689 and cv. Quench, respectively (FIG. 18A). The PCR reactions consisted of 100 ng genomic DNA in 20 μl reaction buffer containing 25 μmol primer and 7 μl REDTaq mix (Sigma), used according to the manufacturer's instructions. The 29-cycles PCR amplifications were carried out in an MJ cycler: 2 min at 96° C. for 1 cycle; 1 min at 95° C.; 1 min at 68° C.; 1 min at 72° C.; ending with a 10-min extension at 72° C.

Cross pollination between a homozygous barley plant carrying the LOX-1 mutation and a homozygous plant carrying the LOX-2 mutation may result in 4 different events. Using two sets of primers, one SNP primer set—FL820 (SEQ ID NO:10 and FL823 (SEQ ID NO:11)—for identification of the LOX-1 mutation (G→A mutation at position 3474 of the LOX-1 gene), and one SNP primer set—FL1034 (SEQ ID NO:9) and FL1039 (SEQ ID NO:8)—for identification of a LOX-2 gene mutation [G→A substitution at position 2689 of the LOX-2 gene (SEQ ID NO:1)], it should be possible to identify one of the four aforementioned crossing events (outlined in FIG. 18B). In other words, a single combined PCR reaction can be used to generate PCR products specific for both of the aforementioned LOX-1 and LOX-2 mutations. The oligonucleotide primers used to amplify the SNP PCR product for the G→A mutation at position 3474 in the LOX-1 gene were 5'-CAAGGTGCGGTTGCTGGTGTC-3' (SEQ ID NO:10) and 5'-CTCGCGCGTCTCCTTCCAT-3' (SEQ ID NO:11), generating a 166-bp DNA fragment comprising a part of the coding region for LOX-1. The oligonucleotide primers used to amplify the SNP PCR product for detection of the G→A mutation at position 2689 in the gene for LOX-2 were 5'-ACCTCAAGGACGCGGCGTGA-3' (SEQ ID NO:9) and 5'-GAGCGAGGAGTACGCGGAG-3' (SEQ ID NO:8), generating a 200-bp DNA fragment comprising part of the coding region of LOX-2. FIG. 18C, lane 2, details that double null-LOX mutant A689 carried both of the aforementioned mutations, whereas the wild-type control carried neither (FIG. 18C, lane 3).

Figure 19:
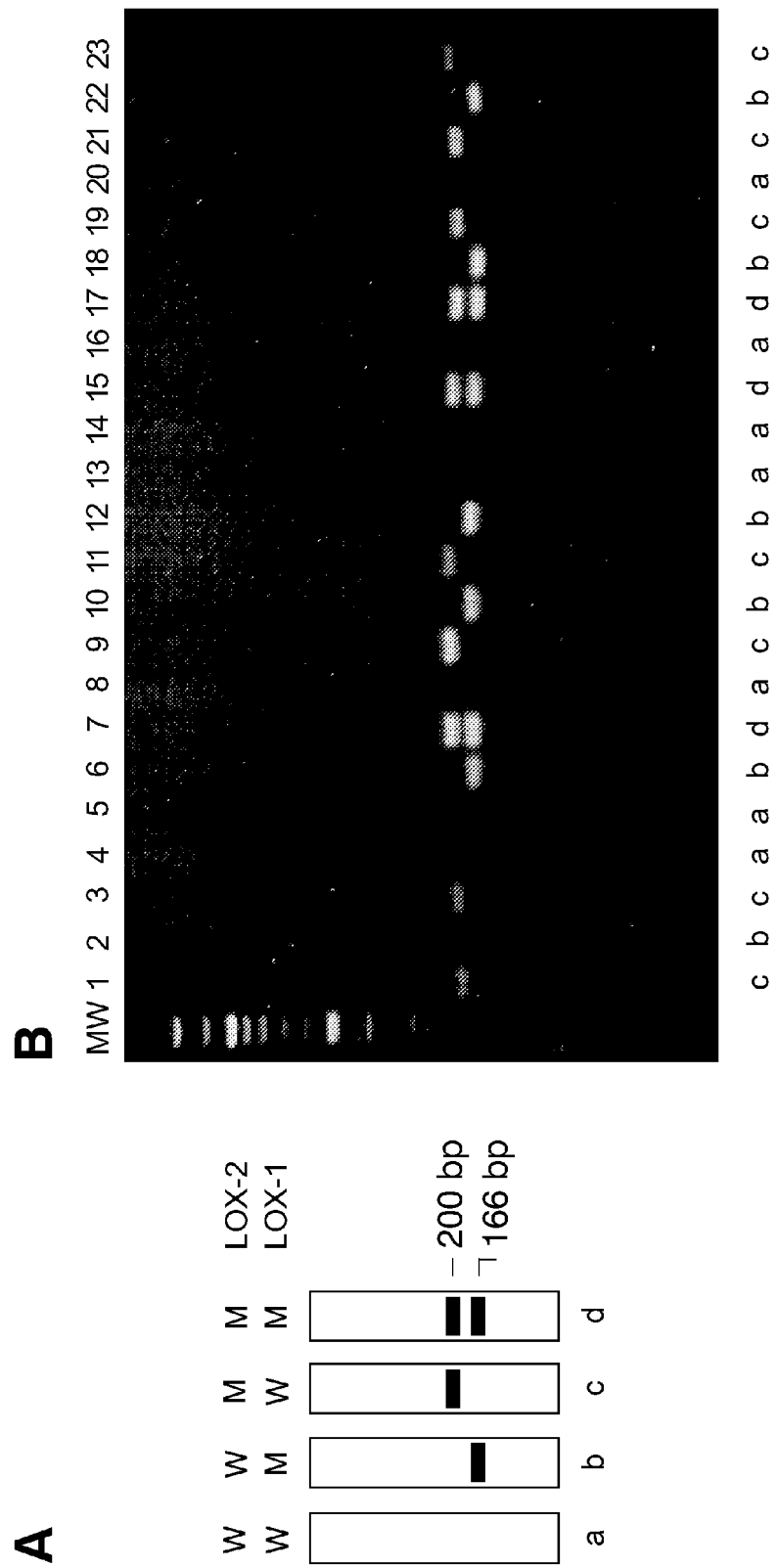
FIG. 19 shows an example on SNP-assisted analysis of off-spring plants from crosses with double null-LOX barley. (A) A schematic representation using the primer combinations detailed in the legend to FIG. 18 herein above, i.e. primers for PCR-based detection of null-LOX-1 and null-LOX-2 mutations. The first lane from left—with band pattern "a", as noted below the lane—contains no specific PCR product for the presence of the two mutations [i.e. both template regions had wild-type (W) sequences], while the next lane with band pattern "b" highlights a PCR product derived from a null-LOX-1 mutant plant (M). The third lane with band pattern "c" is derived from a null-LOX-2 plant, and that in the fourth lane with band pattern "d" is of a double null-LOX plant. (B) Agarose gel electrophoresis of wild-type, null-LOX-1, null-LOX-2, and double null-LOX barley genotypes. Analysis of the banding patterns, according to that described above in (A), revealed that lanes 2, 6, 10, 12, 18, and 22 contained amplified products from plants carrying the null-LOX-1 mutation (marked with "b" below the lanes), while lanes 1, 3, 9, 11, 19, 21, and 23 contained products from plants carrying the null-LOX-2 mutation (marked with "c" below the lanes). Lanes 7, 15, and 17 contained PCR products from double null-LOX plants carrying the combined LOX-1 and LOX-2 gene mutations (marked with "d" below the lanes). And lanes 4, 5, 8, 13, 14, 16, and 20 contained no amplification products from plants carrying either of the null-LOX alleles (marked with "a" below the lanes), i.e. the plants were wild-type with respect to the tested sequences. Marker DNA is separated in lane marked with "MW".

In another experiment, using the REDExtract-N-Amp Plant PCR Kit (Sigma) according to the manufacturer's instructions, genomic barley DNA was isolated from leaf tissues of 23 breeding line seedlings, and subsequently used in PCR reactions that consisted of 100 ng genomic DNA in 20 μl reaction buffer containing 25 μmol primer. Amplifications were carried out in a DNA Engine cycler (MJ Research), according to the manufacturer's instructions: 2 min at 96° C. for 1 cycle; 1 min at 95° C., 1 min at 68° C., 1 min at 72° C. for 29 cycles; and finally 10 min at 72° C. for 1 cycle. FIG. 19 shows the banding pattern following electrophoresis of the PCR products. Analysis revealed that the procedure is useful for selection of the desired combination null-LOX-1 and null-LOX-2 mutations.

Sequence Listing

| SEQ ID NO: 1 | The sequence of wild-type genomic DNA encoding LOX-2 from cv. Barke. |
|---|---|
| SEQ ID NO: 2 | The sequence of mutant LOX-2 genomic DNA from barley mutant A689. |
| SEQ ID NO: 3 | Primer for amplification of protein coding region for LOX-2 (also designated FL960). |
| SEQ ID NO: 4 | Primer for amplification of protein coding region of genomic LOX-2 DNA (also designated FL961). |
| SEQ ID NO: 5 | The sequence of full length LOX-2 protein of wild type barley, cv. Barke. |
| SEQ ID NO: 6 | The sequence of mutant LOX-2 protein lacking LOX-2 activity from barley mutant A689. |
| SEQ ID NO: 7 | Primer for amplification of wild type LOX-2 DNA (also designated FL1035). |
| SEQ ID NO: 8 | Primer for amplification of LOX-2 DNA (also designated FL1039). |
| SEQ ID NO: 9 | Primer for amplification of mutant LOX-2 DNA of mutant A689 (also designated FL1034). |

| | -continued |
|---|---|
| SEQ ID NO: 10 | Primer for amplification of mutant LOX-1 DNA of mutant D112 (also designated FL820). |
| SEQ ID NO: 11 | Primer for amplification of LOX-1 DNA (also designated FL823). |

REFERENCES CITED

Patent Documents
U.S. Pat. No. 4,683,195 to Mullis, K. B. et al.
U.S. Pat. No. 4,800,159 to Mullis, K. B. et al.
PCT patent application WO 02/053721 to Douma, A. C. et al.
PCT patent application WO 2005/087934 to Breddam, K. et al.
European patent no. EP 1609866 to Hirota, N. et al.
Other Publications
American Association of Cereal Chemists, "Approved methods of the American Association of Cereal Chemists." ISBN 0-913250-86-4 (1995).
American Society of Brewing Chemists, "Methods of analysis of the American Society of Brewing Chemists." ISBN 1-881696-01-4 (1992).
Baur, C. and Grosch. W., "Investigation about the taste of di-, tri- and tetrahydroxy fatty acids." Z. Lebensm. Unters. Forsch. 165: 82-84 (1977).
Baur, C. et al., "Enzymatic oxidation of linoleic acid: Formation of bittertasting fatty acids." Z. Lebensm. Unters. Forsch. 164:171-176 (1977).
Briggs, D. E. et al., "Malting and brewing science. Volume I Malt and sweet wort." Chapman and Hall. New York. USA. ISBN 0412165805 (1981).
Drost, B. W. et al., "Role of individual compounds in beer staling." Tech. Q. MBAA 11:127-134 (1974).
Durai, S. et al., "Zinc finger nucleases: custom-designed molecular scissors for genome engineering of plant and mammalian cells." Nucleic Acids Res. 33:5978-5990 (2005).
European Brewery Convention. "Analytica—EBC." ISBN 3-418-00759-7 (1998).
Groenqvist, A. et al., "Carbonyl compounds during beer production in beer." Proceedings of the 24th EBC Congress, Oslo, pp. 421-428 (1993).
Hamberg, M., "Trihydroxyoctadecenoic acids in beer: Qualitative and quantitative analysis." J. Agric. Food Chem. 39:1568-1572 (1991).
Hansen, M. et al., "Antisense-mediated suppression of C-hordein biosynthesis in the barley grain results in correlated changes in the transcriptome, protein profile, and amino acid composition." J. Exp. Bot. 58:3987-3995 (2007).
Hough, J. S. et al., "Malting and brewing science. Volume II Hopped wort and beer." Chapman and Hall, New York, USA. ISBN 0412165902 (1982).
Iida, S, and Terada, R., "Modification of endogenous natural genes by gene targeting in rice and other higher plants." Plant Mol. Biol. 59:205-219 (2005).
Institute of Brewing, "Institute of Brewing. Methods of analysis." ISBN 0-900489-10-3 (1997).
Jamieson, A. M. and van Gheluwe, J. E. A., "Identification of a compound responsible for cardboard flavor in beer." Proc. Am. Soc. Brew. Chem. 29:192-197 (1970).
Kleinhofs, A. et al., "Induction and selection of specific gene mutations in Hordeum and Pisum." Mut. Res. 51:29-35 (1978).
Kumar, S. et al., "Gene targeting in plants: fingers on the move." Trends Plant Sci. 11:159-161 (2006).
Kuroda, H. et al., "Characterization of factors involved in the production of 2(E)-nonenal during mashing." Biosci. Biotechnol. Biochem. 67:691-697 (2003).
Kuroda, H. et al., "Characterization of 9-fatty acid hydroperoxide lyase-like activity in germinating barley seeds that transforms 9(S)-hydroperoxy-10(E).12(Z)-octadecadienoic acid into 2(E)-nonenal." Biosci. Biotechnol. Biochem. 69:1661-1668 (2005).
Lermusieau, G. et al., "Nonoxidative mechanism for development of trans-2-nonenal in beer." J. Am. Soc. Brew. Chem. 57:29-33 (1999).
Liégeois, C. et al., "Release of deuterated (E)-2-nonenal during beer aging from labeled precursors synthesized before boiling." J. Agric. Food Chem. 50:7634-7638 (2002).
Maquat, L. E. and Carmichael, G. G., "Quality control of mRNA function." Cell 104:173-176 (2001).
Meilgaard, M. C., "Flavor chemistry of beer: Part II: Flavor and threshold of 239 aroma volatiles." Tech. Q. MBAA 12:151-167 (1975).
Mendell, J. T. and Dietz, H. C., "When the message goes awry: Disease-producing mutations that influence mRNA content and performance." Cell 107:411-414 (2002).
Nevo, E., "Resources for Breeding of Wild Barley." In: "Barley: Genetics. Biochemistry. Molecular Biology and Biotechnology." Shewry. P. R., ed., pp. 3-18. C.A.B. International. ISBN 0-85198-725-7 (1992).
Noordermeer, M. A. et al., "Fatty acid hydroperoxide lyase: A plant cytochrome P450 enzyme involved in wound healing and pest resistance." ChemBioChem 2:494-504 (2001).
Nyborg, M. et al., "Investigations of the protective mechanism of sulfite against beer staling and formation of adducts with trans-2-nonenal." J. Am. Soc. Brew. Chem. 57:24-28 (1999).
Rasmussen, S. K. and Hatzack, F., "Identification of two low-phytate barley (Hordeum vulgare L.) grain mutants by TLC and genetic analysis." Hereditas 129:107-112 (1998).
Robbins, M. P. et al., "Gene manipulation of condensed tannins in higher plants." Plant Physiol. 116:1133-1144 (1998).
Sambrook, J. and Russell. D. W., "Molecular Cloning. A Laboratory Manual. 3rd Ed.", Cold Spring Harbor Laboratory Press. Cold Spring Harbor. New York. ISBN 0-87969-577-3 (2001).
Schmitt, N. F. and van Mechelen. J. R., "Expression of lipoxygenase isoenzymes in developing barley grains." Plant Sci. 128:141-150 (1997).
Stahl, Y. et al., "Antisense downregulation of the barley limit dextrinase inhibitor modulates starch granule sizes distribution. starch composition and amylopectin structure". Plant J. 39:599-611 (2004).
Tzfira, T. and White. C., "Towards targeted mutagenesis and gene replacement in plants." Trends Biotechnol. 23:567-569 (2005).
von Bothmer, R. et al., "Diversity in barley (Hordeum vulgare)." In: "Diversity in Barley (Hordeum vulgare)." von Bothmer, R., van Hintum, T., Knüpffer, H., Sato. K., eds., pp. 129-136. ISBN 0-444-50587-7 (2003). Also available at http://www.genres.de/.
Wackerbauer, K. and Meyna, S., "Freie und triglyceridegebundene Hydroxyfettsäuren in Gerste und Malz", Monatsschrift für Brauwissenschaft, heft 3/4: 52-57 (2002).
Wu, J. et al., "Nonsense-mediated mRNA decay (NMD) silences the accumulation of aberrant trypsin proteinase inhibitor mRNA in Nicotiana attenuate." Plant J. 51:693-706 (2007).

The invention claimed is:

1. A beverage prepared from a barley plant, or from a part of said plant, wherein said beverage comprises less than 50% trans-2-nonenal (T2N) potential compared to the T2N potential of a beverage prepared in the same manner from barley cv. Power, and wherein said barley plant or part of said plant comprises a first mutation that results in a total loss of functional lipoxygenase (LOX)-1 enzyme, and a second mutation resulting in a total loss of functional LOX-2 enzyme.

2. The beverage according to claim 1, wherein said beverage is a malt beverage.

3. The beverage according to claim 1, wherein the beverage is beer.

4. The beverage according to claim 1, wherein the beverage is barley beer.

5. The beverage according to claim 1, wherein the beverage comprises less than 40% free T2N compared to a beverage prepared in the same manner from barley cv. Power after storage for 8 weeks at 37° C.

6. A barley plant or part thereof comprising a first mutation that results in a total loss of functional LOX-1 enzyme, and a second mutation resulting in a total loss of functional LOX-2 enzyme, wherein unmutated LOX-1 is encoded by the nucleic acid sequence of SEQ ID NO:12 and unmutated LOX-2 is encoded by the nucleic acid sequence of SEQ ID NO:1.

7. The barley plant or part thereof according to claim 6, wherein the gene encoding LOX-1 of said plant comprises a premature stop codon.

8. The barley plant or part thereof according to claim 6, wherein the gene encoding LOX-1 of said plant comprises a nonsense codon, said codon corresponding to base nos. 3572-3574 of SEQ ID NO: 13.

9. The barley plant or part thereof according to claim 6, wherein the gene encoding LOX-2 of said plant comprises a premature stop codon.

10. The barley plant or part thereof according to claim 6, wherein the gene encoding LOX-2 of said plant comprises a mutation at nucleotide position 2689 of SEQ ID NO:1, leading to formation of a stop codon.

11. The barley plant or part thereof according to claim 6, wherein said plant is selected from the group consisting of plants designated "Barley, *Hordeum vulgare* L.: Line A689," deposited with ATCC 13 with the deposit number PTA-9640, and progeny plants thereof comprising said first and second mutations.

12. A beverage prepared from the barley plant or part thereof according to claim 7, wherein said beverage comprises less than 50% T2N potential compared to the T2N potential of a beverage prepared in the same manner from barley cv. Power.

13. A beverage prepared from the barley plant or part thereof according to claim 8, wherein said beverage comprises less than 50% T2N potential compared to the T2N potential of a beverage prepared in the same manner from barley cv. Power.

14. A method of producing a beverage comprising the steps of:
   (i) Preparing a composition comprising a barley plant or part thereof, according to claim 6; and
   (ii) Processing the composition of (i) into a beverage.

15. A method of producing a malt composition comprising the steps of:
   (i) Providing kernels of a barley plant according to claim 6;
   (ii) Steeping said kernels;
   (iii) Germinating the steeped kernels; and
   (iv) Treating germinated kernels with heat.

16. The method according to claim 15, wherein the malt composition comprises at the most 50% T2N compared to the free T2N in a malt composition prepared from the same manner from barley mutant D112 having ATCC deposit accession No. PTA-5487.

17. A method of preparing a barley plant comprising a first mutation resulting in a total loss of functional LOX-1 enzyme, and a second mutation resulting in a total loss of functional LOX-2 enzyme, comprising the steps of:
   (i) Providing a barley plant or part thereof with a total loss of functional LOX-1 enzyme;
   (ii) Mutagenizing said barley plant, barley cells, barley tissue, barley kernels, and/or barley embryos from said barley plant thereby obtaining generation M0 barley;
   (ii) Breeding said mutagenized barley plants, kernels, and/or embryos for at least 2 generations, thereby obtaining generation Mx barley plants, wherein x is an integer ≥2;
   (iv) Obtaining embryos from said Mx barley plants;
   (v) Germinating said embryos;
   (vi) Determining the LOX-1 and LOX-2 activities in the germinated embryos or part thereof;
   (vii) Selecting plants with a total loss of LOX-1 and LOX-2 activities in the germinated embryos;
   (viii) Determining the presence or absence of a mutation in the gene encoding LOX-1 and in the gene encoding LOX-2; and
   (ix) Selecting plants carrying a mutation in the gene encoding LOX-1 and in the gene encoding LOX-2;
   thereby obtaining one or more barley plants comprising a first mutation resulting in a total loss of functional LOX-1 enzyme, and a second mutation resulting in a total loss of functional LOX-2 enzyme.

\* \* \* \* \*

UNITED STATES PATENT AND TRADEMARK OFFICE
CERTIFICATE OF CORRECTION

PATENT NO. : 9,363,959 B2  
APPLICATION NO. : 13/141579  
DATED : June 14, 2016  
INVENTOR(S) : Birgitte Skadhauge et al.

Page 1 of 1

It is certified that error appears in the above-identified patent and that said Letters Patent is hereby corrected as shown below:

In the claims,

Column 80, In claim 16, line 4, after "D112" insert a space;

Column 80, In claim 17, line 14, change "MO" to --M0--; and

Column 80, In claim 17, line 28, after "LOX-1" insert a space.

Signed and Sealed this
Twenty-third Day of August, 2016

Michelle K. Lee
*Director of the United States Patent and Trademark Office*

SEQUENCE LISTING

<160> NUMBER OF SEQ ID NOS: 13

<210> SEQ ID NO 1
<211> LENGTH: 3229
<212> TYPE: DNA
<213> ORGANISM: Hordeum vulgare cv: Barke

<400> SEQUENCE: 1

| | | | | | |
|---|---|---|---|---|---|
| atgtttggcg | tcggcggcat | cgtgagcgac | ctgacggggg | gcctccgggg | cgcccacctc | 60 |
| aagggctccg | tcgtcctcat | gcgcaagaac | gcgctcgact | tcaacgactt | cggcgccacc | 120 |
| gtcatggacg | gcgtcaccga | gctcctcggc | cgcggcgtca | cctgccagct | catcagctcc | 180 |
| accaacgtcg | accacagtga | gcactcactc | gccactcccc | gttttgtaat | ccctgccact | 240 |
| gtgatacatg | gaaaacggaa | gcagatccgc | atcctcacgc | ccgaaccaag | caaataatat | 300 |
| atataaagaa | ctaaaatgca | cgtatggtta | cggatgcatg | cttatgcttg | agcttgagct | 360 |
| tgagcttgag | agacagggac | gtgcaaaaaa | taacttaata | atggagtaac | taatgtgaga | 420 |
| catgacgcac | ggagggtttt | accttactac | taattaattg | tcgagcagac | aacggtgggc | 480 |
| gcgggaaggt | gggcgcggag | gcgaacctgg | agcagtggct | cctgccgacg | aacctgccgt | 540 |
| tcatcaccac | cggcgagaac | aagttcgccg | tcaccttcga | ctggtcggtg | acaagctgg | 600 |
| gggtgccggg | ggccatcatc | gtcaagaaca | accacgcctc | cgagttcttc | ctcaagacca | 660 |
| tcaccctcga | caacgtgccc | ggccgcggca | ccatcgtctt | cgtcgccaac | tcatgggtct | 720 |
| acccgcaggc | caagtaccgc | tacaaccgcg | tcttcttcgc | caacgacgtg | agtattttat | 780 |
| acgagtacca | ctccatggta | gctagtacga | tggatttcgc | ttgctcgatg | cctgactggt | 840 |
| cggttccgtt | gggacatacg | tgccgcagac | gtacctgccg | caccagatgc | cggcggcgct | 900 |
| gaagccgtac | cgcgacgacg | agctccggaa | cctgaggggc | gacgaccagc | aggggcccta | 960 |
| cctggaccac | gaccgcgtct | accgctacga | cgtctacaac | gacctcggcg | actcccgcga | 1020 |
| cgtcctcggc | ggctccaagg | acctccccta | cccgcgccgc | tgccgcaccg | gccggaagcc | 1080 |
| ctcggacagc | agtgcgtgtc | tcctcccttc | tccttccttt | cgatctcccc | ataacgtgta | 1140 |
| cttggtctga | caagcatgtg | tggccgacgc | agagcccgac | cacgagagcc | ggctgctgcc | 1200 |
| gctggtgcag | aacgtctacg | tgccgcgcga | cgagctcttc | ggccacctca | agcagtcgga | 1260 |
| cttcctgggc | tacacgctca | aggcgctggt | ggacgggatc | ataccggcca | tccgcaccta | 1320 |
| cgtcgacctc | tcccccggcg | agttcgactc | cttcgccgac | atcctcaagc | tctacgaggg | 1380 |
| cggcatcaag | ctgcccaaca | tcccggccct | cgaggaggtg | cgcaagcgct | cccgctcca | 1440 |
| gctcgtcaag | gacctcatcc | caagggcgg | cgacttcctc | ctcaagctcc | ccaagccgga | 1500 |
| gatcatcaag | gtagaccaga | aagcgtggat | gactgacgag | gagttcgcca | gggagatgct | 1560 |
| cgccggcgtc | aacccatga | tgatcaaacg | cctcaccgtg | agtgaccac | tccatctacc | 1620 |
| ggccattgaa | caaaatcgtc | catacatgtc | actaatcaat | actcacaccg | ttttgaccgc | 1680 |
| gtgtgcagga | gttccctccc | aagagcactc | tggatccgag | caagtacggc | gaccacacca | 1740 |
| gcaccatgac | cgaggagcac | gtggccaaga | gcctggaggg | cctcaccgtg | cagcaggcgc | 1800 |
| tcgccggcaa | caggctctac | atcgtagacc | agcacgacaa | cctgatgccg | ttcctgatcg | 1860 |
| acatcaacaa | cctcgacgcc | agcttcgtgt | acgccacaag | gacgctgctc | ttcctgcgag | 1920 |
| gggacggcac | gctggcgccg | gtcgccatcg | agctgagctc | gccgctgatc | cagggcgagc | 1980 |
| tgaccaccgc | caagagcgcc | gtgtacacgc | gcagcacgc | cggcgtggag | ggctggatat | 2040 |
| ggcagctcgc | caaggcctac | gcctccgtga | acgactacgg | gtggcaccag | ctcatcagcc | 2100 |

```
actggctcaa cacgcacgcc gtcatggagc ccttcgtcat cgccaccaac aggcagctca    2160
gcgtcaccca cccggtctac aagctcctgc acccgcacta ccgcgacacc atgaacatca    2220
acgcgcgggc gcgcgggctg ctcatcaacg ccggcggcgt catcgagatg accgtgttcc    2280
cgcacaagca cgccatgccc atgtcctcca tggtctacaa gcactggaac ttcaccgaac    2340
aagctctccc cgccgatcta atcaagaggt gcaacatgtt tacattatat aattgacgaa    2400
acggtccttg atttgatcaa aatgattaat cgatcttgat ggttgatgat gatgtagggg    2460
catggcggtg gaggacgcat cgagcccgca caaggtgcgg ctgctgatca aggactaccc    2520
gtacgcgacc gacgggctgg ccgtgtggga cgccatcgag cagtgggtgt cggactacct    2580
gaccatctac taccccaacg acggcgtgct gcagggcgac gtggagctgc aggcgtggtg    2640
gaaggaggtg agggaggtcg gcacggcga cctcaaggac gcggcgtggt ggccaaagat    2700
gcagacggtg gcggagctga tcaaggcgtg cgccaccatc atctggaccg gtcggcgct    2760 ccacgcggcc gtcaacttcg gcagtaccc ctactcgggc taccacccca caagccgtc    2820 ggcgagccgg aggccgatgc cggtgcaggg gagcgaggag tacgcggagc tggagcgaga    2880
cccggagaag gccttcatcc gcaccatcac cagccagttc catgccctgg tgggcatctc    2940
gctcatggag atcctctcca gcactcctc cgacgaggtc tacctgggcc agcacgacac    3000
gccggcgtgg acgtcggacg ccaaggcgct ggaggcgttc aagcggttcg gggcgaagct    3060
ggagggcatc gagaagcagg tggtggccat gaactcggac ccgcagctaa agaaccgcac    3120
cgggccggcc aagttcccat acatgctgct ctacccaaac acctccgacc acacgggaca    3180
ggccgagggg ctcaccgcca ggggcatccc gaacagcata tccatctga             3229
```

<210> SEQ ID NO 2
<211> LENGTH: 3229
<212> TYPE: DNA
<213> ORGANISM: Hordeum vulgare Mutant A689

<400> SEQUENCE: 2

```
atgtttggcg tcggcggcat cgtgagcgac ctgacggggg gcctccgggg cgcccacctc      60
aagggctccg tcgtcctcat gcgcaagaac gcgctcgact tcaacgactt cggcgccacc     120
gtcatggacg cgtcaccga gctcctcggc cgcggcgtca cctgccagct catcagctcc     180
accaacgtcg accacagtga gcactcactc gccactcccc gttttgtaat ccctgccact     240
gtgatacatg aaaacggaa gcagatccgc atcctcacgc ccgaaccaag caaataatat     300
atataaagaa ctaaaatgca cgtatggtta cggatgcatg cttatgcttg agcttgagct     360
tgagcttgag agacagggac gtgcaaaaaa taacttaata atggagtaac taatgtgaga     420
catgacgcac ggagggggtttt accttactac taattaattg tcgagcagac aacggtgggc     480
gcgggaaggt gggcgcggag gcgaacctgg agcagtggct cctgccgacg aacctgccgt     540
tcatcaccac cggcgagaac aagttcgccg tcaccttcga ctggtcggtg acaagctgg     600 gggtgccggg ggccatcatc gtcaagaaca accacgcctc cgagttcttc ctcaagacca     660
tcaccctcga caacgtgccc ggccgcggca ccatcgtctt cgtcgccaac tcatgggtct     720
acccgcaggc caagtaccgc tacaaccgcg tcttcttcgc caacgacgtg agtattttat     780
acgagtacca ctccatggta gctagtacga tggatttcgc ttgctcgatg cctgactggt     840
cggttccgtt gggacatacg tgccgcagac gtacctgccg caccagatgc cggcggcgct     900
gaagccgtac cgcgacgacg agctccggaa cctgaggggc gacgaccagc aggggcccta     960
```

```
cctggaccac gaccgcgtct accgctacga cgtctacaac gacctcggcg actcccgcga      1020
cgtcctcggc ggctccaagg acctccccta cccgcgccgc tgccgcaccg gccggaagcc      1080
ctcggacagc agtgcgtgtc tcctcccttc tccttccttt cgatctcccc ataacgtgta      1140
cttggtctga caagcatgtg tggccgacgc agagcccgac cacgagagcc ggctgctgcc      1200
gctggtgcag aacgtctacg tgccgcgcga cgagctcttc ggccacctca gcagtcgga       1260
cttcctgggc tacacgctca aggcgctggt ggacgggatc ataccggcca tccgcaccta      1320
cgtcgacctc tccccggcg agttcgactc cttcgccgac atcctcaagc tctacgaggg       1380
cggcatcaag ctgcccaaca tcccggccct cgaggaggtg cgcaagcgct cccgctcca       1440
gctcgtcaag gacctcatcc ccaagggcgg cgacttcctc ctcaagctcc ccaagccgga      1500
gatcatcaag gtagaccaga aagcgtggat gactgacgag gagttcgcca gggagatgct      1560
cgccggcgtc aaccccatga tgatcaaacg cctcaccgtg agtgacccac tccatctacc      1620
ggccattgaa caaaatcgtc catacatgtc actaatcaat actcacaccg ttttgaccgc      1680
gtgtgcagga gttccctccc aagagcactc tggatccgag caagtacggc gaccacacca      1740
gcaccatgac cgaggagcac gtggccaaga gcctggaggg cctcaccgtg cagcaggcgc      1800
tcgccggcaa caggctctac atcgtagacc agcacgacaa cctgatgccg ttcctgatcg      1860
acatcaacaa cctcgacgcc agcttcgtgt acgccacaag gacgctgctc ttcctgcgag      1920
gggacggcac gctggcgccg gtcgccatcg agctgagctc gccgctgatc cagggcgagc      1980
tgaccaccgc caagagcgcc gtgtacacgc cgcagcacgc cggcgtggag ggctggatat      2040
ggcagctcgc caaggcctac gcctccgtga acgactacgg gtggcaccag ctcatcagcc      2100
actggctcaa cacgcacgcc gtcatggagc ccttcgtcat cgccaccaac aggcagctca      2160
gcgtcaccca cccggtctac aagctcctgc accgcactac cgcgacacc atgaacatca       2220
acgcgcgggc gcgcgggctg ctcatcaacg ccggcggcgt catcgagatg accgtgttcc      2280
cgcacaagca cgccatgccc atgtcctcca tggtctacaa gcactggaac ttcaccgaac      2340
aagctctccc cgccgatcta atcaagaggt gcaacatgtt tacattatat aattgacgaa      2400
acggtccttg atttgatcaa aatgattaat cgatcttgat ggttgatgat gatgtagggg      2460
catggcggtg gaggacgcat cgagcccgca caaggtgcgg ctgctgatca aggactaccc      2520
gtacgcgacc gacgggctgg ccgtgtggga cgccatcgag cagtgggtgt cggactacct      2580
gaccatctac taccccaacg acggcgtgct gcagggcgac gtggagctgc aggcgtggtg      2640
gaaggaggtg agggaggtcg ggcacggcga cctcaaggac gcggcgtgat ggccaaagat      2700
gcagacggtg gcggagctga tcaaggcgtg cgccaccatc atctggaccg ggtcggcgct      2760
ccacgcggcc gtcaacttcg ggcagtaccc ctactcgggc taccacccca caagccgtc       2820
ggcgagccgg aggccgatgc cggtgcaggg gagcgaggag tacgcggagc tggagcgaga      2880
cccggagaag gccttcatcc gcaccatcac cagccagttc catgccctgg tgggcatctc      2940
gctcatggag atcctctcca gcactcctc cgacgaggtc tacctgggcc agcacgacac       3000
gccggcgtgg acgtcggacg ccaaggcgct ggaggcgttc aagcggttcg ggcgaagct       3060
ggagggcatc gagaagcagg tggtggccat gaactcggac ccgcagctaa gaaccgcac       3120
cgggccggcc aagttcccat acatgctgct ctacccaaac acctccgacc acacgggaca      3180
ggccgagggg ctcaccgcca ggggcatccc gaacagcata tccatctga                 3229
```

<210> SEQ ID NO 3
<211> LENGTH: 30

```
<212> TYPE: DNA
<213> ORGANISM: Artificial sequence
<220> FEATURE:
<223> OTHER INFORMATION: Primer for amplification of Hordeum vulgare
      LOX-2 gDNA

<400> SEQUENCE: 3
cgcagcgagc taacttagaa gcgtgccaca                                        30

<210> SEQ ID NO 4
<211> LENGTH: 30
<212> TYPE: DNA
<213> ORGANISM: Artificial sequence
<220> FEATURE:
<223> OTHER INFORMATION: Primer for amplification of Hordeum vulgare
      LOX-2 gDNA

<400> SEQUENCE: 4
cctcatgcct ttgtgctatc cttgcttgct                                        30

<210> SEQ ID NO 5
<211> LENGTH: 864
<212> TYPE: PRT
<213> ORGANISM: Hordeum vulgare cv: Barke

<400> SEQUENCE: 5

Met Leu Gly Val Gly Ile Val Ser Asp Leu Thr Gly Gly Ile Arg
1               5                   10                  15

Gly Ala His Leu Lys Gly Ser Val Val Leu Met Arg Lys Asn Ala Leu
                20                  25                  30

Asp Phe Asn Asp Phe Gly Ala His Val Met Asp Gly Val Thr Glu Leu
            35                  40                  45

Leu Gly Arg Gly Val Thr Cys Gln Leu Ile Ser Ser Thr Asn Val Asp
    50                  55                  60

His Asn Asn Gly Gly Arg Gly Lys Val Gly Ala Glu Ala Asn Leu Glu
65                  70                  75                  80

Gln Trp Leu Leu Pro Thr Asn Leu Pro Phe Ile Thr Thr Gly Glu Asn
                85                  90                  95

Lys Phe Ala Val Thr Phe Asp Trp Ser Val Asp Lys Leu Gly Val Pro
            100                 105                 110

Gly Ala Ile Ile Val Lys Asn Asn His Ala Ser Glu Phe Phe Leu Lys
        115                 120                 125

Thr Ile Thr Leu Asp Asn Val Pro Gly Arg Gly Thr Ile Val Phe Val
130                 135                 140

Ala Asn Ser Trp Val Tyr Pro Gln Ala Lys Tyr Arg Tyr Asn Arg Val
145                 150                 155                 160

Phe Phe Ala Asn Asp Thr Tyr Leu Pro His Gln Met Pro Ala Ala Leu
                165                 170                 175

Lys Pro Tyr Arg Asp Asp Glu Leu Arg Asn Leu Arg Gly Asp Gly Gln
            180                 185                 190

Gln Gly Pro Tyr Leu Asp His Asp Arg Val Tyr Arg Tyr Asp Val Tyr
        195                 200                 205

Asn Asp Leu Gly Asp Ser Arg Asp Val Leu Gly Gly Ser Lys Asp Leu
    210                 215                 220

Pro Tyr Pro Arg Arg Cys Arg Thr Gly Arg Lys Pro Ser Asp Ser Lys
225                 230                 235                 240

Pro Asp His Glu Ser Arg Leu Leu Leu Leu Val Gln Asn Val Tyr Val
                245                 250                 255
```

```
Leu Arg Asp Glu Leu Phe Gly His Leu Lys Gln Ser Asp Leu Leu Gly
            260                 265                 270

Tyr Thr Leu Lys Gly Trp Leu Asp Gly Ile Ile Leu Ala Ile Arg Thr
        275                 280                 285

Tyr Val Asp Leu Ser Pro Gly Glu Phe Asp Ser Phe Ala Asp Ile Leu
    290                 295                 300

Lys Leu Tyr Glu Gly Gly Ile Lys Leu Pro Asn Ile Pro Ala Leu Glu
305                 310                 315                 320

Glu Val Arg Lys Arg Phe Pro Leu Gln Leu Val Lys Asp Leu Ile Pro
                325                 330                 335

Lys Gly Gly Asp Phe Leu Leu Lys Leu Pro Lys Pro Glu Ile Ile Lys
            340                 345                 350

Val Asp Gln Lys Ala Trp Met Thr Asp Glu Glu Phe Ala Arg Glu Met
        355                 360                 365

Leu Ala Gly Val Asn Pro Met Met Ile Lys Arg Leu Thr Glu Phe Pro
    370                 375                 380

Pro Lys Ser Thr Leu Asp Pro Ser Lys Tyr Gly Asp His Thr Ser Thr
385                 390                 395                 400

Met Thr Glu Glu His Val Ala Lys Ser Leu Glu Gly Leu Thr Val Gln
                405                 410                 415

Gln Ala Leu Ala Gly Asn Arg Leu Tyr Ile Val Asp Gln His Asp Asn
            420                 425                 430

Leu Met Pro Phe Leu Ile Asp Ile Asn Asn Leu Asp Ala Ser Phe Val
        435                 440                 445

Tyr Ala Thr Arg Thr Leu Leu Phe Leu Arg Gly Asp Gly Thr Leu Ala
    450                 455                 460

Pro Val Ala Ile Glu Leu Ser Ser Pro Leu Ile Gln Gly Glu Leu Thr
465                 470                 475                 480

Thr Ala Lys Ser Ala Val Tyr Thr Pro Gln His Ala Gly Val Glu Gly
                485                 490                 495

Trp Ile Trp Gln Leu Ala Lys Ala Tyr Ala Ser Val Asn Asp Tyr Gly
            500                 505                 510

Trp His Gln Leu Ile Ser His Trp Leu Asn Thr His Ala Val Met Glu
        515                 520                 525

Pro Phe Val Ile Ala Thr Asn Arg Gln Leu Ser Val Thr His Pro Val
    530                 535                 540

Tyr Lys Leu Leu His Pro His Tyr Arg Asp Thr Met Asn Ile Asn Ala
545                 550                 555                 560

Arg Ala Arg Gly Leu Leu Ile Asn Ala Gly Gly Val Ile Glu Met Thr
                565                 570                 575

Val Phe Pro His Lys His Ala Met Pro Met Ser Ser Met Val Tyr Lys
            580                 585                 590

His Trp Asn Phe Thr Glu Gln Ala Leu Pro Ala Asp Leu Ile Lys Arg
        595                 600                 605

Gly Met Ala Val Glu Asp Ala Ser Ser Pro His Lys Val Arg Leu Leu
    610                 615                 620

Ile Lys Asp Tyr Pro Tyr Ala Thr Asp Gly Leu Ala Val Trp Asp Ala
625                 630                 635                 640

Ile Glu Gln Trp Val Ser Asp Tyr Leu Thr Ile Tyr Tyr Pro Asn Asp
                645                 650                 655

Gly Val Leu Gln Gly Asp Val Glu Leu Gln Ala Trp Trp Lys Glu Val
            660                 665                 670

Arg Glu Val Gly His Gly Asp Leu Lys Asp Ala Ala Trp Trp Pro Lys
```

```
              675                 680                 685
Met Gln Thr Val Ala Glu Leu Ile Lys Ala Cys Ala Thr Ile Ile Trp
690                 695                 700

Thr Gly Ser Ala Leu His Ala Val Asn Phe Gly Gln Tyr Pro Tyr
705                 710                 715                 720

Ser Gly Tyr His Pro Asn Lys Pro Ser Ala Ser Arg Arg Pro Met Pro
                725                 730                 735

Val Gln Gly Ser Glu Glu Tyr Ala Glu Leu Glu Arg Asp Pro Glu Lys
                740                 745                 750

Ala Phe Ile Arg Thr Ile Thr Ser Gln Phe His Ala Leu Val Gly Ile
                755                 760                 765

Ser Leu Met Glu Ile Leu Ser Lys His Ser Ser Asp Glu Val Tyr Leu
770                 775                 780

Gly Gln His Asp Thr Pro Ala Trp Thr Ser Asp Ala Lys Ala Leu Glu
785                 790                 795                 800

Ala Phe Lys Arg Phe Gly Ala Lys Leu Glu Gly Ile Glu Lys Gln Val
                805                 810                 815

Val Ala Met Asn Ser Asp Pro Gln Leu Lys Asn Arg Thr Gly Pro Ala
                820                 825                 830

Lys Phe Pro Tyr Met Leu Leu Tyr Pro Asn Thr Ser Asp His Thr Gly
                835                 840                 845

Gln Ala Glu Gly Leu Thr Ala Arg Gly Ile Pro Asn Ser Ile Ser Ile
850                 855                 860

<210> SEQ ID NO 6
<211> LENGTH: 684
<212> TYPE: PRT
<213> ORGANISM: Hordeum vulgare mutant A689

<400> SEQUENCE: 6

Met Leu Gly Val Gly Gly Ile Val Ser Asp Leu Thr Gly Gly Ile Arg
1               5                   10                  15

Gly Ala His Leu Lys Gly Ser Val Val Leu Met Arg Lys Asn Ala Leu
                20                  25                  30

Asp Phe Asn Asp Phe Gly Ala His Val Met Asp Gly Val Thr Glu Leu
            35                  40                  45

Leu Gly Arg Gly Val Thr Cys Gln Leu Ile Ser Ser Thr Asn Val Asp
    50                  55                  60

His Asn Asn Gly Gly Arg Gly Lys Val Gly Ala Glu Ala Asn Leu Glu
65                  70                  75                  80

Gln Trp Leu Leu Pro Thr Asn Leu Pro Phe Ile Thr Thr Gly Glu Asn
                85                  90                  95

Lys Phe Ala Val Thr Phe Asp Trp Ser Val Asp Lys Leu Gly Val Pro
            100                 105                 110

Gly Ala Ile Ile Val Lys Asn Asn His Ala Ser Glu Phe Phe Leu Lys
        115                 120                 125

Thr Ile Thr Leu Asp Asn Val Pro Gly Arg Gly Thr Ile Val Phe Val
    130                 135                 140

Ala Asn Ser Trp Val Tyr Pro Gln Ala Lys Tyr Arg Tyr Asn Arg Val
145                 150                 155                 160

Phe Phe Ala Asn Asp Thr Tyr Leu Pro His Gln Met Pro Ala Ala Leu
                165                 170                 175

Lys Pro Tyr Arg Asp Asp Glu Leu Arg Asn Leu Arg Gly Asp Asp Gln
            180                 185                 190
```

```
Gln Gly Pro Tyr Leu Asp His Asp Arg Val Tyr Arg Tyr Asp Val Tyr
            195                 200                 205

Asn Asp Leu Gly Asp Ser Arg Asp Val Leu Gly Gly Ser Lys Asp Leu
    210                 215                 220

Pro Tyr Pro Arg Arg Cys Arg Thr Gly Arg Lys Pro Ser Asp Ser Lys
225                 230                 235                 240

Pro Asp His Glu Ser Arg Leu Leu Leu Val Gln Asn Val Tyr Val
                245                 250                 255

Leu Arg Asp Glu Leu Phe Gly His Leu Lys Gln Ser Asp Leu Leu Gly
            260                 265                 270

Tyr Thr Leu Lys Gly Trp Leu Asp Gly Ile Ile Leu Ala Ile Arg Thr
        275                 280                 285

Tyr Val Asp Leu Ser Pro Gly Glu Phe Asp Ser Phe Ala Asp Ile Leu
        290                 295                 300

Lys Leu Tyr Glu Gly Gly Ile Lys Leu Pro Asn Ile Pro Ala Leu Glu
305                 310                 315                 320

Glu Val Arg Lys Arg Phe Pro Leu Gln Leu Val Lys Asp Leu Ile Pro
                325                 330                 335

Lys Gly Gly Asp Phe Leu Leu Lys Leu Pro Lys Pro Glu Ile Ile Lys
            340                 345                 350

Val Asp Gln Lys Ala Trp Met Thr Asp Glu Glu Phe Ala Arg Glu Met
        355                 360                 365

Leu Ala Gly Val Asn Pro Met Met Ile Lys Arg Leu Thr Glu Phe Pro
        370                 375                 380

Pro Lys Ser Thr Leu Asp Pro Ser Lys Tyr Gly Asp His Thr Ser Thr
385                 390                 395                 400

Met Thr Glu Glu His Val Ala Lys Ser Leu Glu Gly Leu Thr Val Gln
                405                 410                 415

Gln Ala Leu Ala Gly Asn Arg Leu Tyr Ile Val Asp Gln His Asp Asn
            420                 425                 430

Leu Met Pro Phe Leu Ile Asp Ile Asn Asn Leu Asp Ala Ser Phe Val
        435                 440                 445

Tyr Ala Thr Arg Thr Leu Leu Phe Leu Arg Gly Asp Gly Thr Leu Ala
450                 455                 460

Pro Val Ala Ile Glu Leu Ser Ser Pro Leu Ile Gln Gly Glu Leu Thr
465                 470                 475                 480

Thr Ala Lys Ser Ala Val Tyr Thr Pro Gln His Ala Gly Val Glu Gly
                485                 490                 495

Trp Ile Trp Gln Leu Ala Lys Ala Tyr Ala Ser Val Asn Asp Tyr Gly
            500                 505                 510

Trp His Gln Leu Ile Ser His Trp Leu Asn Thr His Ala Val Met Glu
        515                 520                 525

Pro Phe Val Ile Ala Thr Asn Arg Gln Leu Ser Val Thr His Pro Val
        530                 535                 540

Tyr Lys Leu Leu His Pro His Tyr Arg Asp Thr Met Asn Ile Asn Ala
545                 550                 555                 560

Arg Ala Arg Gly Leu Leu Ile Asn Ala Gly Gly Val Ile Glu Met Thr
                565                 570                 575

Val Phe Pro His Lys His Ala Met Pro Met Ser Ser Met Val Tyr Lys
            580                 585                 590

His Trp Asn Phe Thr Glu Gln Ala Leu Pro Ala Asp Leu Ile Lys Arg
        595                 600                 605

Gly Met Ala Val Glu Asp Ala Ser Ser Pro His Lys Val Arg Leu Leu
```

```
                     610                 615                 620

Ile Lys Asp Tyr Pro Tyr Ala Thr Asp Gly Leu Ala Val Trp Asp Ala
625                 630                 635                 640

Ile Glu Gln Trp Val Ser Asp Tyr Leu Thr Ile Tyr Tyr Pro Asn Asp
                    645                 650                 655

Gly Val Leu Gln Gly Asp Val Glu Leu Gln Ala Trp Trp Lys Glu Val
                660                 665                 670

Arg Glu Val Gly His Gly Asp Leu Lys Asp Ala Ala
        675                 680

<210> SEQ ID NO 7
<211> LENGTH: 20
<212> TYPE: DNA
<213> ORGANISM: Artificial sequence
<220> FEATURE:
<223> OTHER INFORMATION: Primer for amplification of Hordeum vulgare
      LOX-2 gDNA

<400> SEQUENCE: 7
acctcaagga cgcggcgtgg                                            20

<210> SEQ ID NO 8
<211> LENGTH: 19
<212> TYPE: DNA
<213> ORGANISM: Artificial sequence
<220> FEATURE:
<223> OTHER INFORMATION: Primer for amplification of Hordeum vulgare
      LOX-2 gDNA

<400> SEQUENCE: 8
gagcgaggag tacgcggag                                             19

<210> SEQ ID NO 9
<211> LENGTH: 20
<212> TYPE: DNA
<213> ORGANISM: Artificial sequence
<220> FEATURE:
<223> OTHER INFORMATION: Primer for amplification of Hordeum vulgare
      mutant A689 LOX-2 gDNA

<400> SEQUENCE: 9
acctcaagga cgcggcgtga                                            20

<210> SEQ ID NO 10
<211> LENGTH: 21
<212> TYPE: DNA
<213> ORGANISM: Artificial sequence
<220> FEATURE:
<223> OTHER INFORMATION: Primer for amplification of Hordeum vulgare
      mutant D112 LOX-1 gDNA

<400> SEQUENCE: 10
caaggtgcgg ttgctggtgt c                                          21

<210> SEQ ID NO 11
<211> LENGTH: 19
<212> TYPE: DNA
<213> ORGANISM: Artificial sequence
<220> FEATURE:
<223> OTHER INFORMATION: Primer for amplification of Hordeum vulgare
      LOX-1 gDNA

<400> SEQUENCE: 11
ctcgcgcgtc tccttccat                                             19
```

<210> SEQ ID NO 12
<211> LENGTH: 4165
<212> TYPE: DNA
<213> ORGANISM: Hordeum vulgare cv. Barke

<400> SEQUENCE: 12

```
atgctgctgg agggctgat  cgacaccctc acggggggcga acaagagcgc ccggctcaag    60
ggcacggtgg tgctcatgcg caagaacgtg ctggacctca acgacttcgg cgccaccatc   120
atcgacggca tcggcgagtt cctcggcaag ggcgtcacct gccagcttat cagctccacc   180
gccgtcgacc aaggtaatca ctaccctcct ccggccttct cctctgttta caagatatag   240
tatttctttc gtgtgggccg gcggccatgg atggatggat gtgtctggat cggctaaaga   300
agataggata gctagccctg gccggtcgtc tttacctgag catgggcata tgccatcgaa   360
aaaagagaca acagcatgca tgcatggtgc gcgcaccaga ccacgcagag caccggatgc   420
tcgagacaaa gcaacacaac aagcaaggac gacacgtcaa agcaacacaa acaagcaagg   480
acggcacgtc aaaagcaaca caaacctaaa ctaaagcaca aagacgtaag agcaagcaca   540
caatcagcag gctataaaca gttgtcatca aaaacaacgc tggaagagag agagaaggaa   600
ggaagtagta gccatgaaaa attaaatcac cgggcgttgc tctttgccca acaattaatc   660
aagcaggata cgtggcatgt atagttcttg taagtaaact aagcatgtga tatgagaagg   720
tacgtggtgg tgcagacaac ggcggtcgcg ggaaggtggg cgcggaggcg agctggagc    780
agtgggtgac gagcctgccg tcgctgacga cgggggagtc caagttcggc ctcaccttcg   840
actgggaggt ggagaagctc ggggtgccgg gcgccatcgt cgtcaacaac taccacagct   900
ccgagttcct gcttaaaacc atcaccctcc acgacgtccc cggccgcagc ggcaacctca   960
ccttcgtcgc caactcatgg atctaccccg ccgccaacta ccgatacagc cgcgtcttct  1020
tcgccaacga cgtgcgtgga ttttcctcta ctttcctctc ctttcatttt caccgccttc  1080
gtcattcatg gtcgatcatt aagtcttgcc aggacaatag atgatgagct aggagtggtt  1140
accacttagc agtacgtaca ttatttattc cgtgttggta gaaaaggata tggtttggtg  1200
cagatcgaca caagattgaa tgaaagttgc accgtggcac cgtggcagcg tggtaggtga  1260
aaataactgt tgcacggatc cacccacatg attgttttca tgaataaact ttttaaggat  1320
gtgtctagcc acatctagat gcatgtcaca taattattgc ataccaaaac gattaaatta  1380
agcataaaaa gaaaggaaa  aaaatactca catatctcga cgtaagatca atgatatagt  1440
atttagatat gcaatattta tcttacatct aaacctttct tcattcctaa atataagaca  1500
tttgtaagat ttcactatgg acaacatacg aaacaaaatc agtggatctc tctatgcatt  1560
cattatgtag tctataataa aatctttaaa agatcgtata ttttgcaacg gagggagtaa  1620
aacataactt tttaatagta atgttgcacg gctccacact cgcagacgta cctgccgagc  1680
cagatgccgg cggcgctgaa gccgtaccgc gacgacgagc tccggaacct gcgtggcgac  1740
gaccagcagg gcccgtacca ggagcacgac cgcatctacc gctacgacgt ctacaacgac  1800
ctcggcgagg gccgccccat cctcggcggc aactccgacc acccttaccc gcgccgcggc  1860
cgcacggagc gcaagcccaa cgccagcgac ccgagcctgg agagccggct gtcgctgctg  1920
gagcagatct acgtgccgcg ggacgagaag ttcggccacc tcaagacgtc cgacttcctg  1980
ggctactcca tcaaggccat cacgcagggc atcctgccgg ccgtgcgcac ctacgtggac  2040
accaccccg  gcgagttcga ctccttccag gacatcatca acctctatga gggcggcatc  2100
aagctgccca aggtggccgc cctggaggag ctccgtaagc agttcccgct ccagctcatc  2160
```

```
aaggacctcc tccccgtcgg cggcgactcc ctgcttaagc tccccgtgcc ccacatcatc    2220
caggagaaca agcaggcgtg gaggaccgac gaggagttcg cacgggaggt gctcgccggc    2280
gtcaacccgg tcatgatcac gcgtctcacg gtgagtcagc gattatttgt tcattgtgtg    2340
tgtatggtgt ccatggtgag aaagtgcaga tcttgatttg cgttgggtcg catgcacgca    2400
tgctgcatgc atgcaggagt tcccgccaaa aagtagtctg gaccctagca gtttggtga     2460 ccacaccagc accatcacgg cggagcacat agagaagaac ctcgagggcc tcacggtgca    2520
gcaggtaatt ggtccaagcc atcgacatca actatgattt acctaggagt aattggtagc    2580
tgtagataat ttggcttcgt tgcaattaat ttgatgctgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg cgacggcag gctcacgccg ctcgccatcg agctgagcga    2820
gcccatcatc cagggcggcc ttaccacggc caagagcaag gtttacacgc cggtgcccag    2880
cggctccgtc gaaggctggg tgtgggagct cgccaaggcc tacgtcgccg tcaatgactc    2940
cgggtggcac cagctcgtca gccactggta cgttctccac ggtcgatgtg attcagtcag    3000
tcgatgcaca acaactgatc gaaatatgat tgattgaaac gcgcaggctg aacactcacg    3060
cggtgatgga gccgttcgtg atctcgacga accggcacct agcgtgacg cacccggtgc     3120 acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcagggactg ccggacgatc    3300
tcatcaagag gtacgtacct ggtaaatgtt atgaatgtgt aaaacaaatt gggcgtctcg    3360
ctcactgaca ggaacgtggt aaaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc cgaacgacgg    3540
cgtgctgcag ggcgatacgg aggtgcaggc gtggtggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca acttcgggca    3720 gtaccctac gcggggttcc tcccgaaccg gccgacggtg agccggcgcc gcatgccgga    3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacacct ccgaccacaa gggcgccgct gccgggctta ccgccaaggg    4140
catccccaac agcatctcca tctaa                                          4165
```

<210> SEQ ID NO 13
<211> LENGTH: 4165
<212> TYPE: DNA
<213> ORGANISM: Hordeum vulgare mutant D112

<400> SEQUENCE: 13

```
atgctgctgg agggctgat cgacaccctc acggggcga acaagagcgc ccggctcaag     60
```

```
ggcacggtgg tgctcatgcg caagaacgtg ctggacctca acgacttcgg cgccaccatc    120
atcgacggca tcggcgagtt cctcggcaag ggcgtcacct gccagcttat cagctccacc    180
gccgtcgacc aaggtaatca ctaccctcct ccggccttct cctctgttta caagatatag    240
tatttctttc gtgtgggccg gcggccatgg atggatggat gtgtctggat cggctaaaga    300
agataggata gctagccctg gccggtcgtc tttacctgag catgggcata tgccatcgaa    360
aaaagagaca acagcatgca tgcatggtgc gcgcaccaga ccacgcagag caccggatgc    420
tcgagacaaa gcaacacaac aagcaaggac gacacgtcaa agcaacacac acaagcaagg    480
acggcacgtc aaaagcaaca caaacctaaa ctaaagcaca aagacgtaag agcaagcaca    540
caatcagcag gctataaaca gttgtcatca aaaacaacgc tggaagagag agagaaggaa    600
ggaagtagta gccatgaaaa attaaatcac cgggcgttgc tctttgccca acaattaatc    660
aagcaggata cgtggcatgt atagttcttg taagtaaact aagcatgtga tatgagaagg    720
tacgtggtgg tgcagacaac ggcggtcgcg ggaaggtggg gcggaggcg gagctggagc    780 agtgggtgac gagcctgccg tcgctgacga cgggggagtc caagttcggc ctcaccttcg    840
actgggaggt ggagaagctc ggggtgccgg gcgccatcgt cgtcaacaac taccacagct    900
ccgagttcct gcttaaaacc atcaccctcc acgacgtccc cggccgcagc ggcaacctca    960
ccttcgtcgc caactcatgg atctacccc cgccaacta ccgatacagc cgcgtcttct   1020
tcgccaacga cgtgcgtgga ttttcctcta ctttcctctc ctttcatttt ccgccttc   1080 gtcattcatg gtcgatcatt aagtcttgcc aggacaatag atgatgagct aggagtggtt   1140
accacttagc agtacgtaca ttatttattc cgtgttggta gaaaaggata tggtttggtg   1200
cagatcgaca caagattgaa tgaaagttgc accgtggcac cgtggcagcg tggtaggtga   1260
aaataactgt tgcacggatc cacccacatg attgttttca tgaataaact ttttaaggat   1320
gtgtctagcc acatctagat gcatgtcaca taattattgc ataccaaaac gattaaatta   1380
agcataaaaa gaaaggaaa aaaatactca catatctcga cgtaagatca atgatatagt   1440
atttagatat gcaatattta tcttacatct aaacctttct tcattcctaa atataagaca   1500
tttgtaagat ttcactatgg acaacatacg aaacaaaatc agtggatctc tctatgcatt   1560
cattatgtag tctataataa aatctttaaa agatcgtata ttttgcaacg gagggagtaa   1620
aacataactt tttaatagta atgttgcacg gctccacact cgcagacgta cctgccgagc   1680
cagatgccgg cggcgctgaa gccgtaccgc gacgacgagc tccggaacct gcgtggcgac   1740
gaccagcagg gcccgtacca ggagcacgac cgcatctacc gctacgacgt ctacaacgac   1800
ctcggcgagg gccgcccat cctcggcggc aactccgacc acccttaccc gcgccgcggc   1860
cgcacggagc gcaagcccaa cgccagcgac ccgagcctgg agagccggct gtcgctgctg   1920
gagcagatct acgtgccgcg ggacgagaag ttcggccacc tcaagacgtc cgacttcctg   1980
ggctactcca tcaaggccat cacgcagggc atcctgccgg ccgtgcgcac ctacgtggac   2040
accacccccg gcgagttcga ctccttccag gacatcatca acctctatga gggcggcatc   2100
aagctgccca aggtggccgc cctggaggag ctccgtaagc agttcccgct ccagctcatc   2160
aaggacctcc tccccgtcgg cggcgactcc ctgcttaagc tccccgtgcc ccacatcatc   2220
caggagaaca agcaggcgtg gaggaccgac gaggagttcg cacgggaggt gctcgccggc   2280
gtcaacccgg tcatgatcac gcgtctcacg gtgagtcagc gattatttgt tcattgtgtg   2340
tgtatggtgt ccatggtgag aaagtgcaga tcttgatttg cgttgggtcg catgcacgca   2400
tgctgcatgc atgcaggagt tcccgccaaa aagtagtctg gaccctagca agtttggtga   2460
```

-continued

```
ccacaccagc accatcacgg cggagcacat agagaagaac ctcgagggcc tcacggtgca    2520
gcaggtaatt ggtccaagcc atcgacatca actatgattt acctaggagt aattggtagc    2580
tgtagataat ttggcttcgt tgcaattaat ttgatgctgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg gcgacggcag gctcacgccg ctcgccatcg agctgagcga    2820
gcccatcatc cagggcggcc ttaccacggc caagagcaag gtttacacgc cggtgcccag    2880
cggctccgtc gaaggctggg tgtgggagct cgccaaggcc tacgtcgccg tcaatgactc    2940
cgggtggcac cagctcgtca gccactggta cgttctccac ggtcgatgtg attcagtcag    3000
tcgatgcaca acaactgatc gaaatatgat tgattgaaac gcgcaggctg aacactcacg    3060
cggtgatgga gccgttcgtg atctcgacga accggcacct tagcgtgacg cacccggtgc    3120
acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcaggactg ccggacgatc    3300
tcatcaagag gtacgtacct ggtaaatgtt atgaatgtgt aaaacaaatt gggcgtctcg    3360
ctcactgaca ggaacgtggt aaaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc gaacgacgg    3540
cgtgctgcag ggcgatacgg aggtgcaggc gtgatggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca acttcgggca    3720
gtaccctac gcggggttcc tcccgaaccg gccgacggtg agccggcgcc gcatgccgga    3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggaccc tggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacacct ccgaccacaa gggcgccgct gccgggctta ccgccaaggg    4140
catccccaac agcatctcca tctaa                                          4165
```